(12) United States Patent
Liu et al.

(10) Patent No.: US 8,143,044 B2
(45) Date of Patent: Mar. 27, 2012

(54) CRYSTAL STRUCTURE OF THE INFLUENZA VIRUS POLYMERASE PAC-PB1$_N$ COMPLEX AND USES THEREOF

(75) Inventors: Yingfang Liu, Beijing (CN); Xiaojing He, Beijing (CN); Zonghao Zeng, Beijing (CN); Jie Zhou, Beijing (CN)

(73) Assignee: Institute of Biophysics Chinese Academy of Sciences, Beijing (CN)

( * ) Notice: Subject to any disclaimer, the term of this patent is extended or adjusted under 35 U.S.C. 154(b) by 0 days.

(21) Appl. No.: 12/918,603

(22) PCT Filed: Feb. 22, 2009

(86) PCT No.: PCT/CN2009/070498
§ 371 (c)(1),
(2), (4) Date: Nov. 4, 2010

(87) PCT Pub. No.: WO2009/103243
PCT Pub. Date: Aug. 27, 2009

(65) Prior Publication Data
US 2011/0131029 A1    Jun. 2, 2011

(30) Foreign Application Priority Data
Feb. 22, 2008 (CN) .................... 2008 1 0100840
May 2, 2008 (CN) .................... 2008 1 0083994

(51) Int. Cl.
*C12N 9/12* (2006.01)
(52) U.S. Cl. . 435/194; 536/23.2; 536/23.1; 435/252.33; 435/320.1

(58) Field of Classification Search .................... None
See application file for complete search history.

(56) References Cited

U.S. PATENT DOCUMENTS

| | | | |
|---|---|---|---|
| 4,235,871 A | 11/1980 | Papahadjopoulos et al. |
| 4,501,728 A | 2/1985 | Geho et al. |
| 4,837,028 A | 6/1989 | Allen |
| 4,902,505 A | 2/1990 | Pardridge et al. |
| 4,957,735 A | 9/1990 | Huang |
| 5,004,697 A | 4/1991 | Pardridge |
| 5,019,369 A | 5/1991 | Presant et al. |

(Continued)

FOREIGN PATENT DOCUMENTS
CN    1541335 A    10/2004

OTHER PUBLICATIONS

Wiencek et al. New Strategies for Protein Crystal Growth. Annu. Rev. Biomed. Eng. 1999 (1), pp. 505-534.*

(Continued)

*Primary Examiner* — Nashaat Nashed
(74) *Attorney, Agent, or Firm* — Scully, Scott, Murphy & Presser, P.C.

(57) ABSTRACT

Provided are the expression method of influenza virus polymerase PAc-PB1$_N$ complex, the co-crystallization method of the complex and the three-dimendional structure of the crystal of PAc-PB1$_N$ complex. Also provided are the compounds binding to the influenza virus polymerase PAc and the expression method of influenza virus polymerase PA$_N$. The three-dimensional structure of the crystal of PAc-PB1$_N$ complex can be used for screening and designing the drug for the treatment of influenza.

Figure 2:
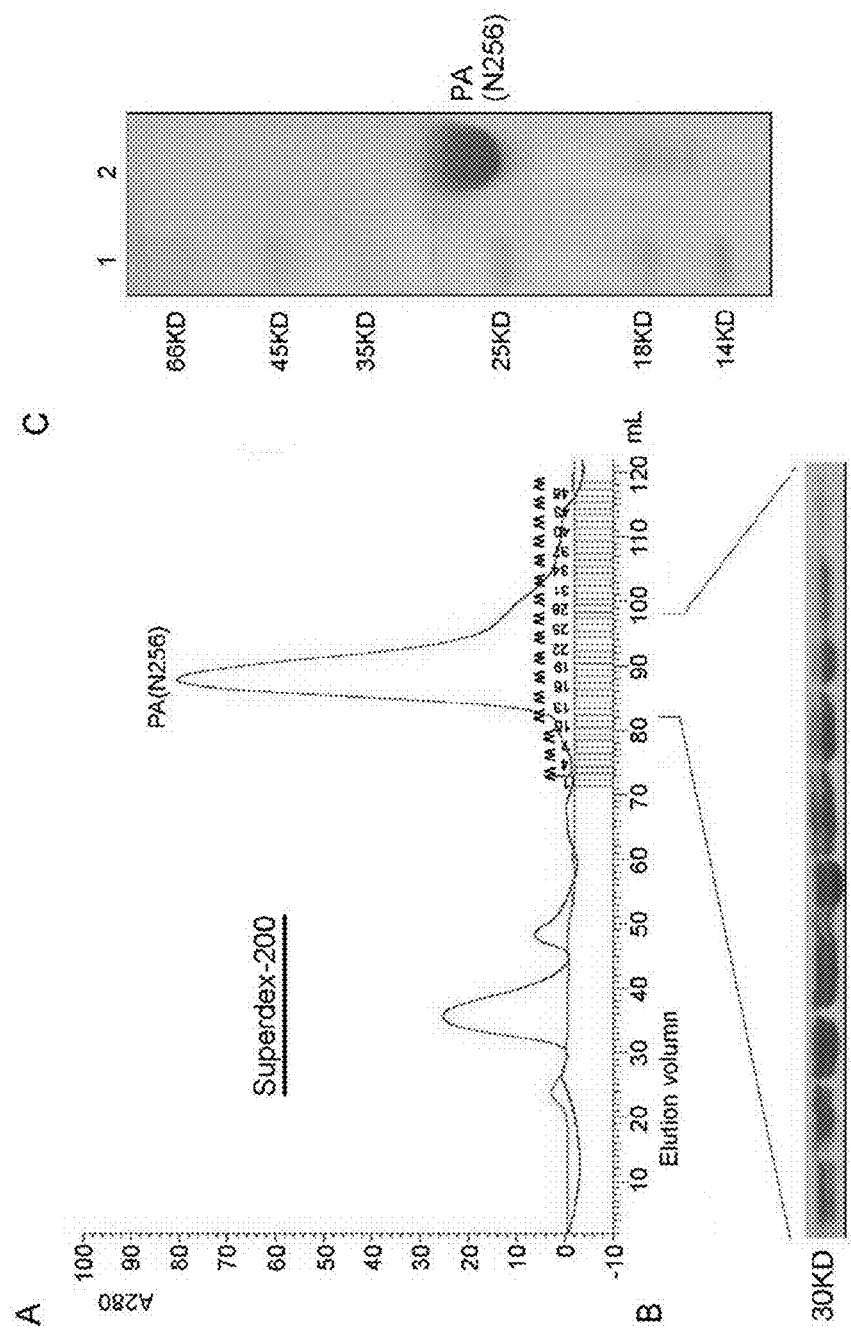
Figure 3:
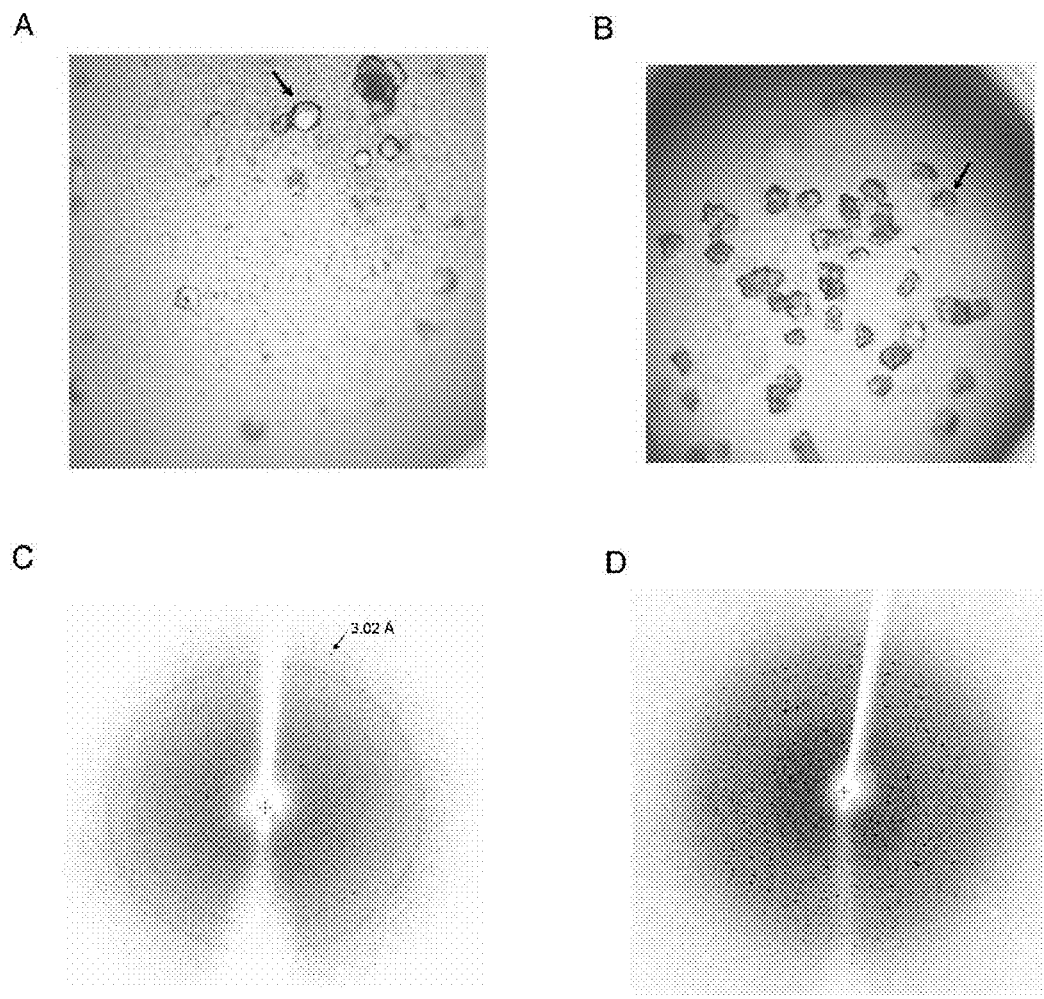
Figure 4:
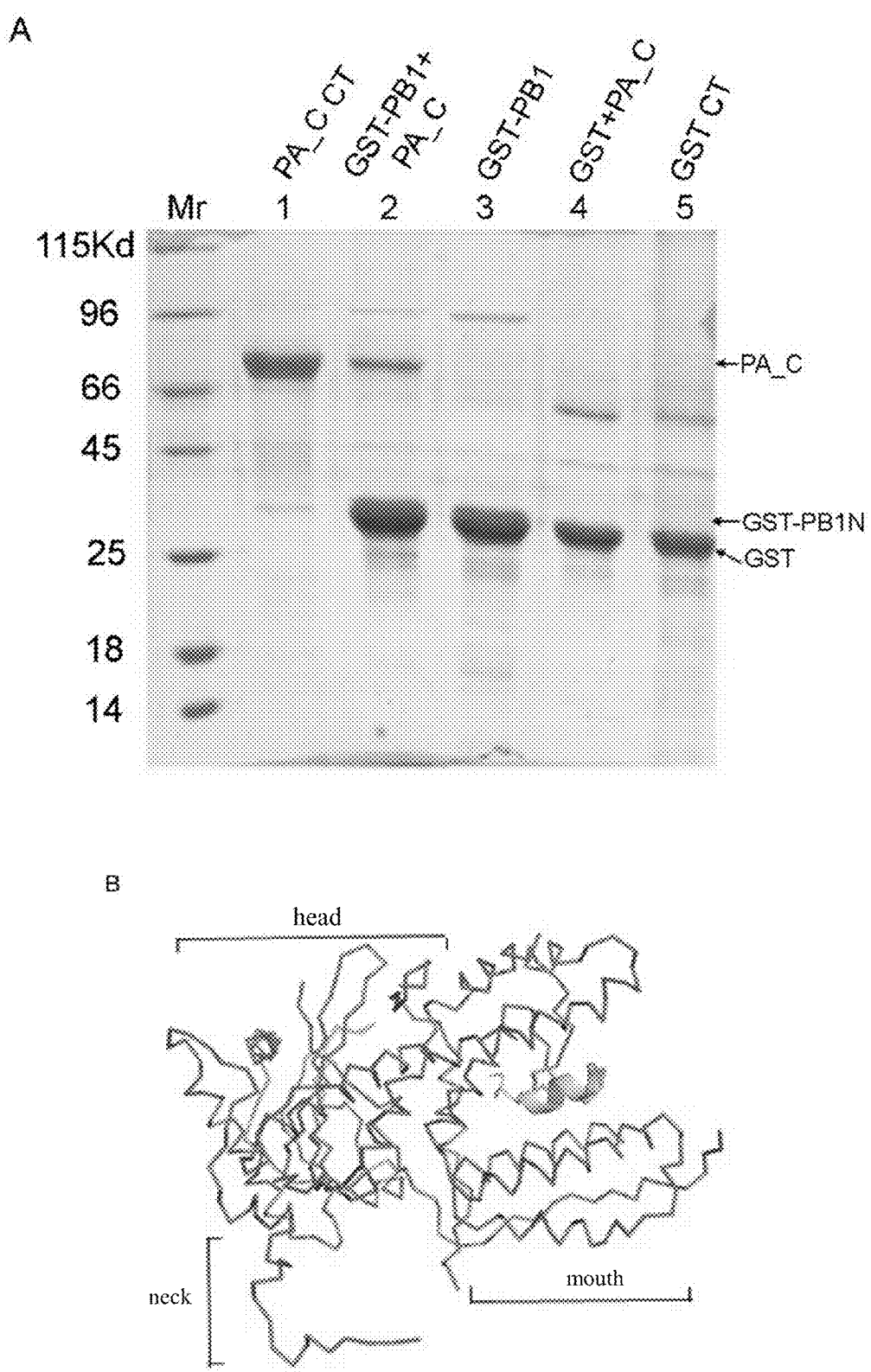
Figure 5:
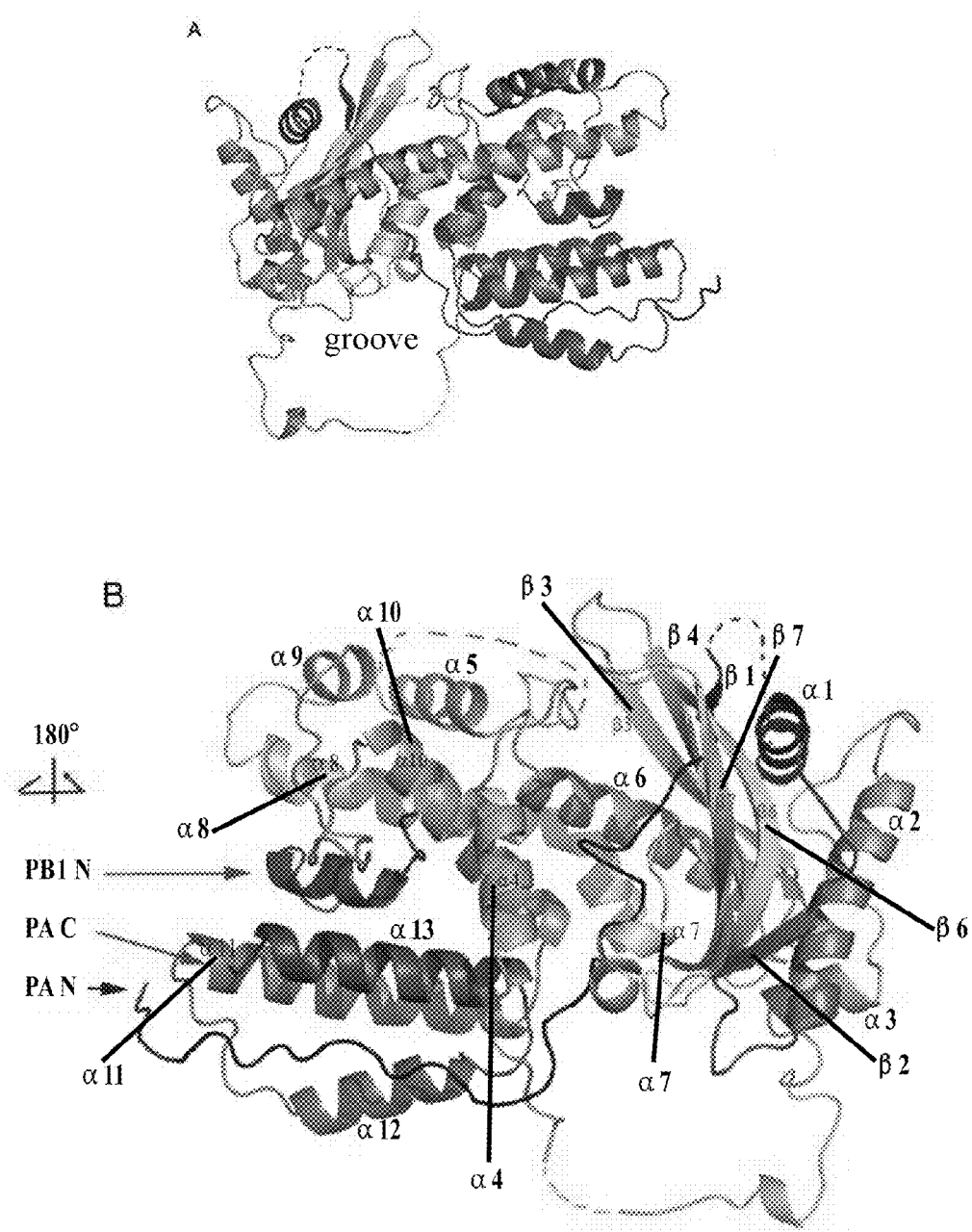
Figure 6:
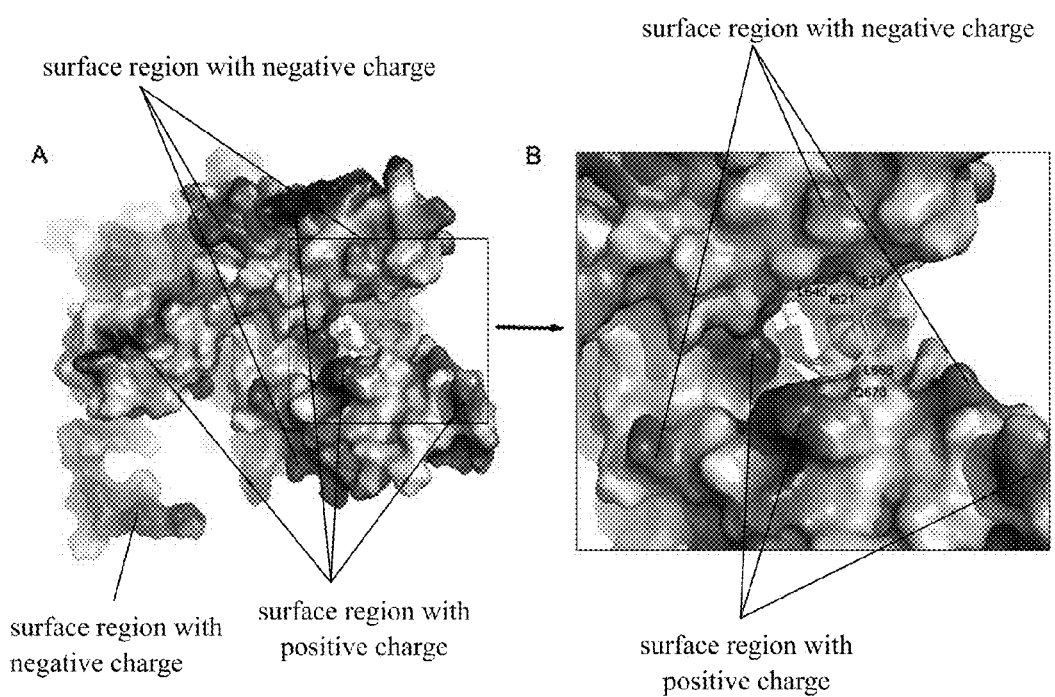
Figure 7:
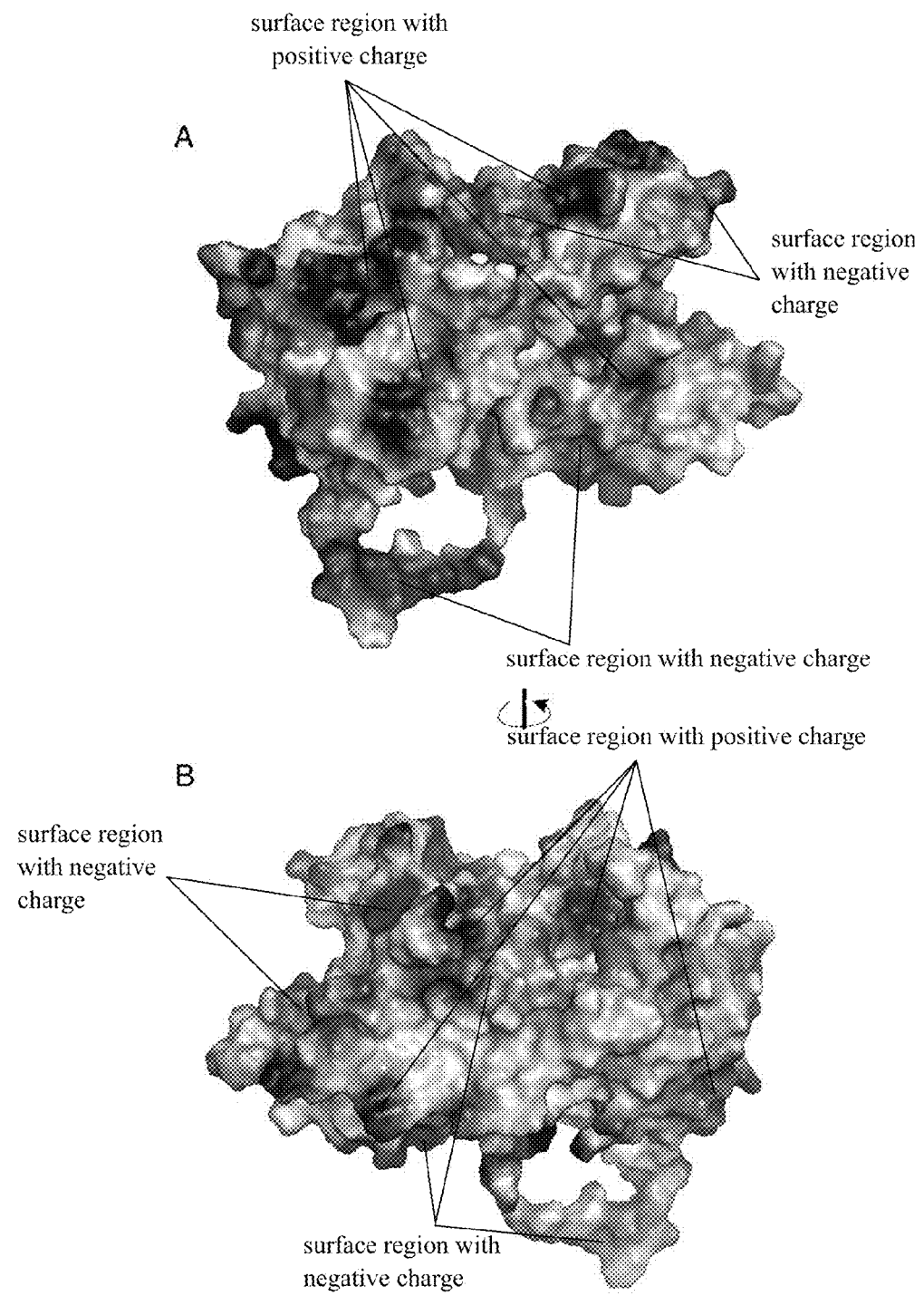

10 Claims, 21 Drawing Sheets
(21 of 21 Drawing Sheet(s) Filed in Color)

U.S. PATENT DOCUMENTS

| | | | |
|---|---|---|---|
| 5,055,303 | A | 10/1991 | Riley, Jr. |
| 5,188,837 | A | 2/1993 | Domb |
| 5,254,342 | A | 10/1993 | Shen et al. |
| 5,268,164 | A | 12/1993 | Kozarich et al. |
| 5,271,961 | A | 12/1993 | Mathiowitz et al. |
| 5,413,797 | A | 5/1995 | Khan et al. |
| 5,506,206 | A | 4/1996 | Kozarich et al. |
| 5,514,670 | A | 5/1996 | Friedman et al. |
| 5,534,496 | A | 7/1996 | Lee et al. |

OTHER PUBLICATIONS

He et al. Crystal Structure of the Polymerase PAc-PB1n Complex from an Avian Influenza H5N1 virus. Nature (Aug. 28, 2008) vol. 454, pp. 1123-1126 (on line version is 9 pages, published Jul. 9, 2008).*

Langer, R., "Polymer-Controlled Drug Delivery Systems" *Accounts Chem. Res.* (1993) pp. 537-542, vol. 26(10).

Johnston, T.P. et al., "Sustained Delivery of Interleukin-2 from a Poloxamer 407 Gel Matrix Following Intraperitoneal Injection in Mice" *Pharmaceutical Research* (1992) pp. 425-434, vol. 9(3).

Fults, K.A. et al., "Sustained-Release of Urease from a Poloxamer Gel Matrix" *Journal of Parenteral Science and Technology* (1990) pp. 58-65, vol. 44(2).

Ijntema, K. et al., "Hydroxyapatite Microcarriers for Bioctonrolled Release of Protein Drugs" *International Journal of Pharmaceuticals* (1994) pp. 215-224, vol. 112.

Schneider, G. et al., "Computer-Based De *Novo* Design of Drug-Like Molecules" *Nature Reviews: Drug Discovery* (2005) pp. 649-663, vol. 4.

Wang, R. et al., "LigBuilder: A Multi-Purpose Program for Structure-Based Drug Design" *Journal of Molecular Modeling* (2000) pp. 498-516, vol. 6.

Goldberg D.R. et al., "Discovery and Optimization of p38 Inhibitos via Computer-Assisted Drug Design" Journal of Medicinal Chemistry (2007) pp. 4016-4026, vol. 50(17).

Ghanem, A. et al., "Paptide-Mediated Interference with Influenza A Virus Polymerase" *Journal of Virology* (2007) pp. 7801-7804, vol. 81(14).

Ohtsu, Y et al. "Fine Mapping of the Subunit Binding Sites of Influenza Virus RNA polymerase" *Microbio. Immunol.* (2002) pp. 167-175, vol. 46(3).

Perez, D. R. et al., "Functional Analysis of PA Binding by Influenza A Virus PB1: Effects on Polymerase Activity and Viral Infectivity" *Journal of Virology* (2001) pp. 8127-8136, vol. 75(17).

Ochoa, M. et al. "Epitope Mapping of Cross-Reactive Monoclonal Antibodies Specific for the Influenza A Virus PA and PB2 Polypeptides" *Virus Research* (1995) pp. 305-315, vol. 37(3).

Torreira, E. et al., "Three-Dimensional Model for the Isolated Recombinant Influenza Virus Polymerase Heterotrimer" *Nucleic Acids Research* (2007) pp. 3374-3783, vol. 35(11).

He X.J. et al., "Crystal Structure of the Polymerase $PA_c$-$PB1_N$ Complex from an Avian Influenza H5N1 Virus" *Nature* (2008) pp. 1123-1126, vol. 454(7208).

Obayashi, E. et al., "The Structural Basis for an Essential Subunit Interaction in Influenza Virus RNA Polymerase" *Nature* (2008) pp. 1127-1131, vol. 454(7208).

International Search Report dated May 28, 2009.

* cited by examiner

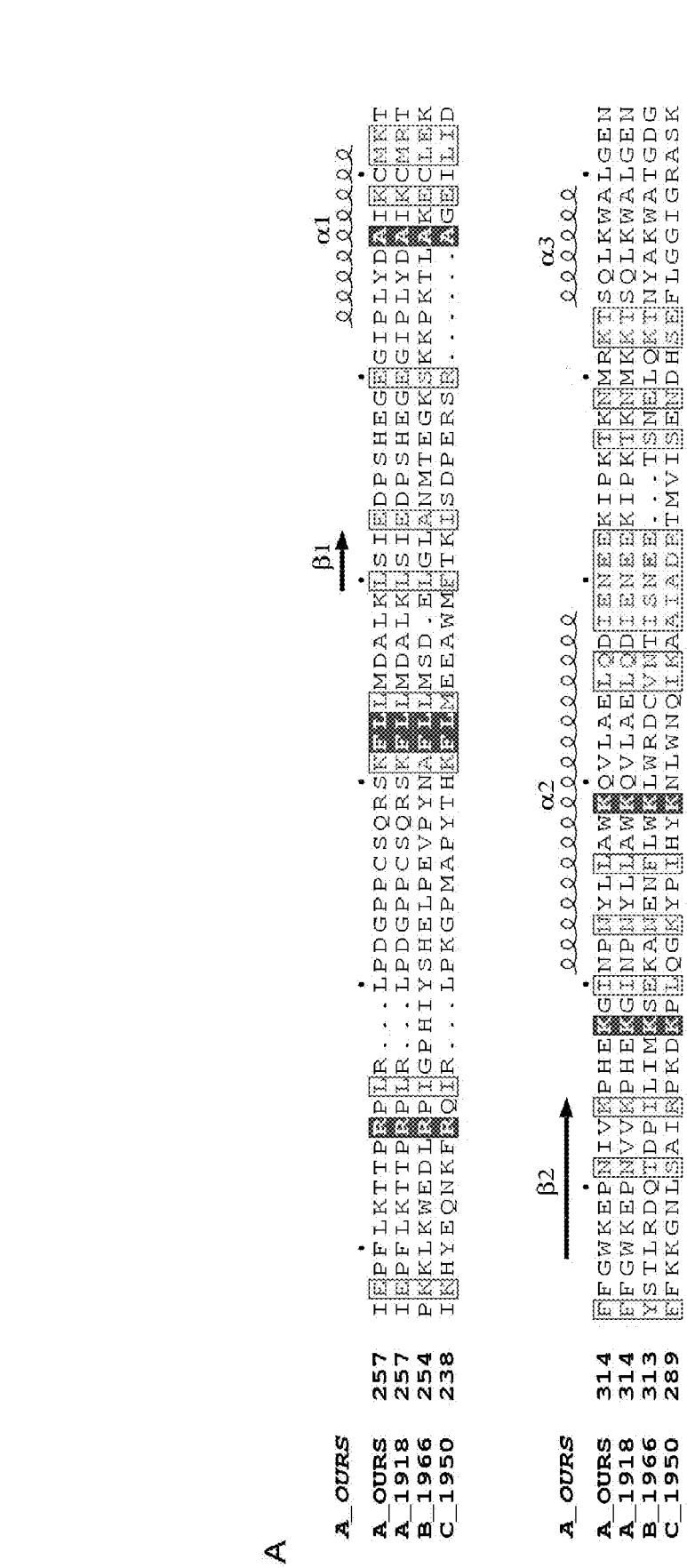
Figure 1A-a

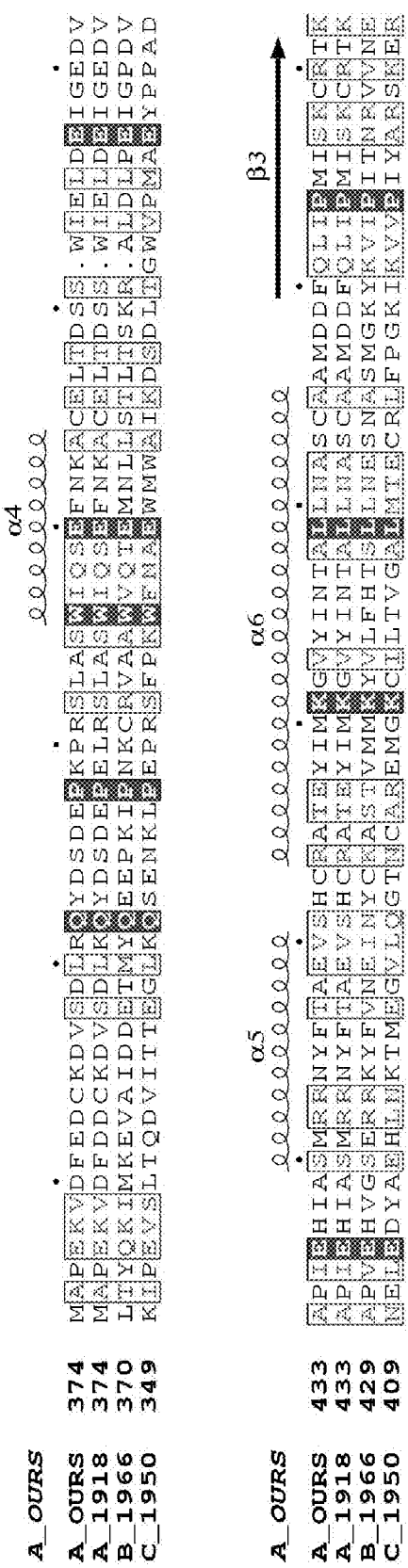
Figure 1A-b

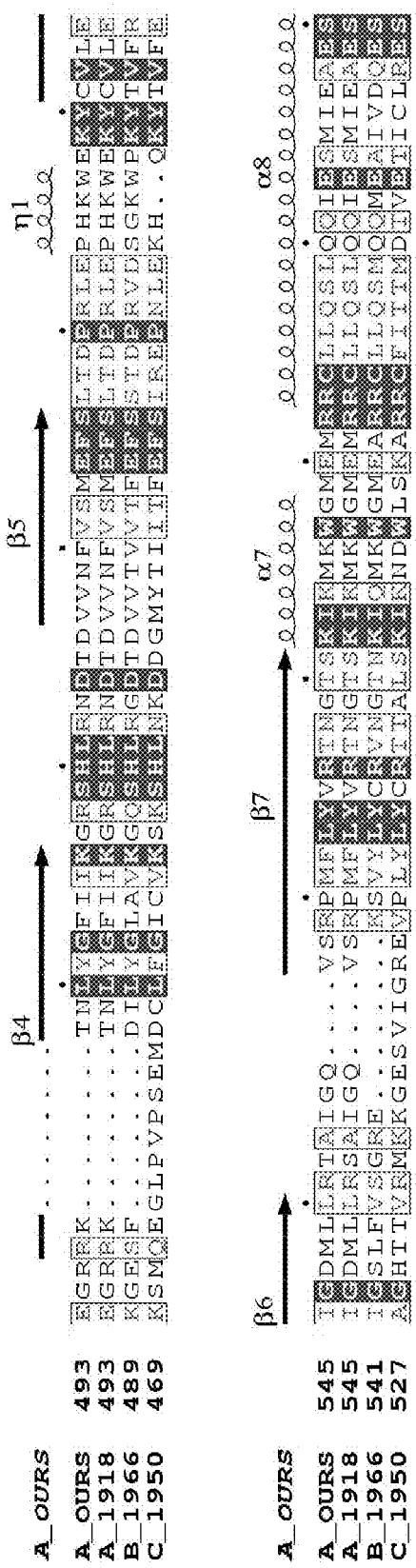
Figure 1A-c

Figure 1A-d

B

```
            η1
          eeeeee
A_OURS
A_OURS  2  D V N P T L L F L K V P A Q N
A_1918  2  D V N P T L L P L K V P A Q N      PB1N
B_1966  2  N I N P Y F L F I D V P I Q A
C_1950  2  E I N P Y L M D L N N D V T S
```

Figure 1B

Figure 1C-a

```
         1          10         20         30         40         50         60
A_OURS   .MEDFVRQCFNPMIVELAEKAMKEYGEDPKIETNKFAAICTHLEVCFMYSDFHFIDERGES
A_1918   .MEDFVRQCFNPMIVELAEKAMKEYGEDLKIETNKFAAICTHLEVCFMYSDFHFINERGES
B_1966   .MDTFITRNFQTTIIQKAKNTMAEFSEDPELQPAMLFNCVHLEVGYVISDMNFLDEGKI
C_1950   .SKTFAEIAETFLEPAVRIAKEAVEEYGDHERKIIQIHFQVGCMFCDEYLSTWGSDR 70         80         90        100        110
A_OURS   .TIIESGDPNALLKHRFEII

```
            120.        130.        140.        150.        160.        170.
A_OURS   ICVHREVHTYLEKANIKSEKTHIHIFSFTGEEMATKADYTLDEESRARIKTRLFTIR
A_1918   ICVHREVHIYYLEKANIKSEKTHIHIFSFTGEEMATKADYTLDEESRARIKTRLFTIR
B_1966   VCIFKGLADDHFWKK

```
          240         250
A_OURS  .GC IE G KLSQ M S KE VNA RI
A_1918  .GY IE G KLSQ M S KE VNA RI
B_1966  .GA IE R NLAR M S PL VSV TP
C_1950  PRE LA S KVSQ M Q SN IKL PI
```

Figure 1C-c

Figure 10-a

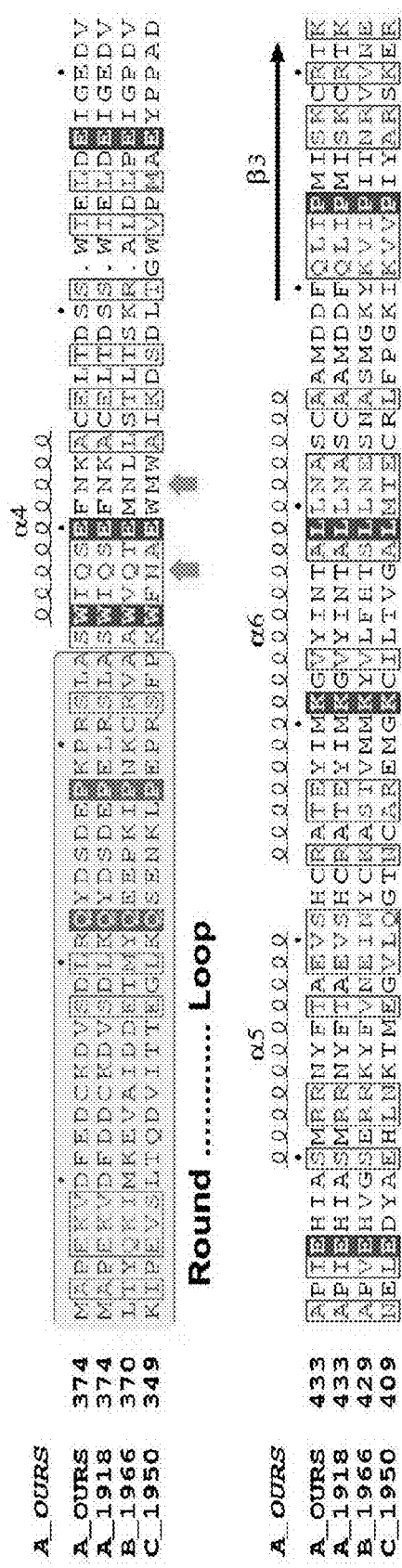
Figure 10-b

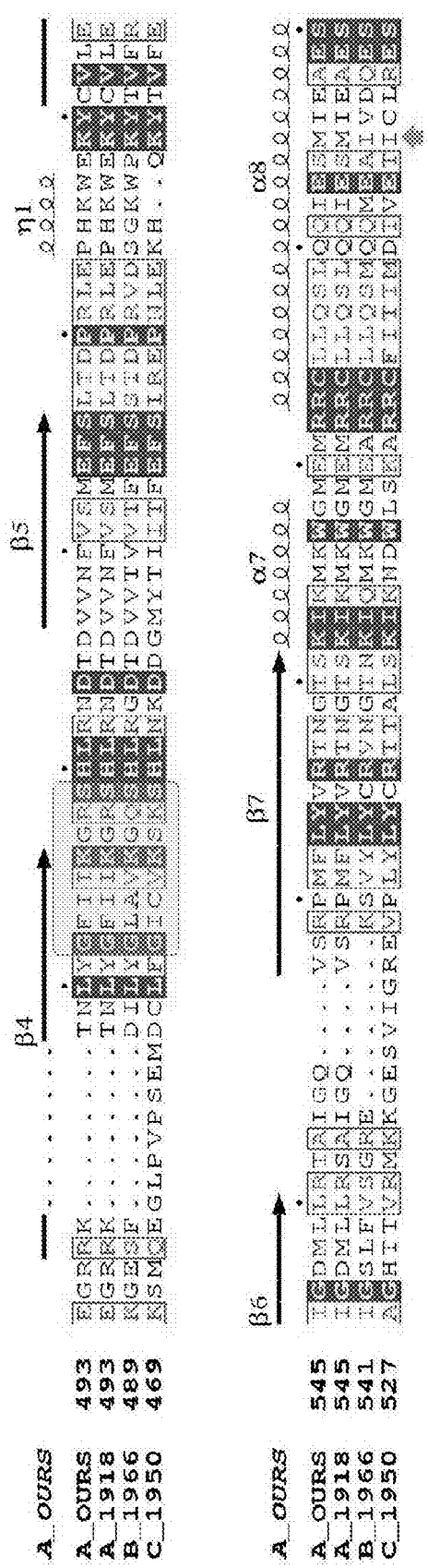
Figure 10-c

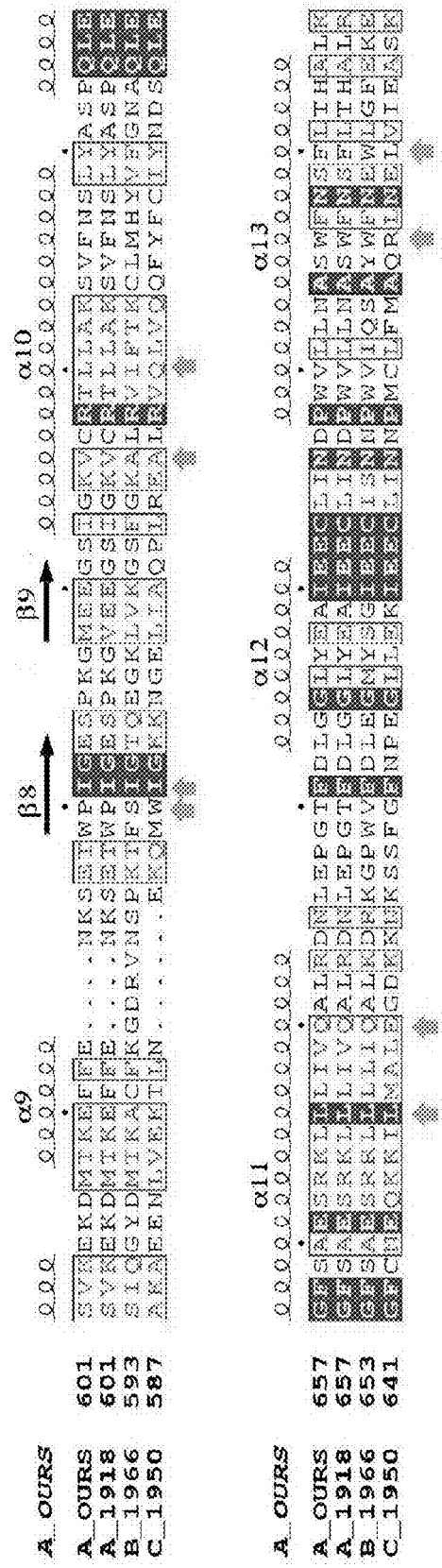
Figure 10-d

B

```
            η2
          ρρρρρρ
A_OURS  1  MDVNPTLLFLKVPAQNASTIFFYD
A_1918  1  MDVNPTLLFLKVPAQNASTIFFYT    PB1_N
B_1966  1  MNINPYFLPIDVPIQAASTIFFYT
C_1950  1  MEINPYLNFLNMDVTSLSTIYRYT
```

Figure 10-e

CRYSTAL STRUCTURE OF THE INFLUENZA VIRUS POLYMERASE PAC-PB1$_N$ COMPLEX AND USES THEREOF

TECHNICAL FIELD

The present invention relates to a method for expression of influenza virus PA (SEQ ID NO:1) and PB1 N-terminal polypeptide in bacteria, purification and crystallization. It also relates to the crystal three-dimensional structure of complex of C-terminal of PA and N-terminal polypeptide of PB1 and its application in drug design.

BACKGROUND ART

Influenza viruses has already caused great disasters for humanity (Taubenberger and Morens 2007). Due to the lack of sufficient treatments and frequent mutations of the virus itself, the virus remains a threat to humans. In recent years, frequent and severe avian influenza epidemics as well as transmission of avian influenza to humans has constituted a great threat to health and economics of humans, so investigations directed to this kind of virus is of great value to protect human health. Avian influenza virus belongs to influenza virus A type, which are all me the members of the Orthomyxoviridae family. The virus genome consists of 8 negative sense single-stranded RNA. Through comparison and analysis of genes of influenza virus of avian origin and other influenza A viruses, sporadic mutations in the primary structure have been found, and these mutations result in differential pathogenicity of different influenza viruses. Now, it is established that the influenza virus genome encodes 11 proteins, wherein the replication of influenza virus genome RNA and mRNA transcription are dependent on a viral RNA polymerase which has become a potentially important drug target. Recent research suggested that the high pathogenicity of some influenza viruses is directly correlated with the polymerase mutations (Hulse-Post, Franks et al. 2007; Munster, de Wit et 20 al. 2007), further illustrating the necessity of designing drugs aiming at this complex. Investigation into this complex is of great significance to reveal the molecular mechanism underlying virus replication and to design drugs aiming at this complex. The RNA polymerase is a complex composed of PB1 (SEQ ID NO:2), PB2 and PA (SEQ ID NO:1) subunits, wherein PB1 (SEQ ID NO:2) is a subunit with catalytic activity, PB2 is responsible for acquiring cellular mRNA cap (CAP structure) through a snatching mode as primers of virus mRNA transcription, but PB1 (SEQ ID NO:2) acts as an endonuclease in this process. A temperature sensitive mutant ts53 suggests that PA (SEQ ID NO:1) takes part in the replication process of virus genome, but its specific function is still unclear (Sugiura, Ueda et al. 1975; Kawaguchi, Naito et al. 2005). The polymerase has three kinds of RNA activity which are needed in virus synthesis, i.e. mRNA, cRNA and vRNA synthesis, respectively. The mRNA synthesis starts from a capped oligonucleotide primer and ends 15-17 nucleotides prior to the vRNA terminal, followed by addition of a polyA tail. Polymerase can synthesize a cRNA intermediate of the full-length virus de novo and further synthesize full-length vRNA. Respective subunits of the polymerase can be expressed by an insect cell expression system, thus forming three different complexes, wherein one is a ternary complex containing the three subunits PB1 (SEQ ID NO:2)/PB2/PA (SEQ ID NO:1) of polymerase, and the other two are binary complexes: PB1 (SEQ ID NO:2)/PB2 and PB1 (SEQ ID NO:2)/PA (SEQ ID NO:1) binary complexes respectively, PB2/PA (SEQ ID NO:1) complex is not formed (Honda, Mizumoto et al. 2002). 25 amino acids of PB1 N-terminal are sufficient to interact with PA (SEQ ID NO:1) C-terminal, while the PB1 C-terminal is responsible for the interaction with PB2 N-terminal. A synthetic competitive small peptide of the PB1 N-terminal can significantly inhibit the activity of virus polymerase. RNA synthesis experiments using dinucleotide ApG as primers indicated that PB1 (SEQ ID NO:2)/PA (SEQ ID NO:1) complex can effectively initiate the replication of virus genome RNA, and PB1 (SEQ ID NO:2)/PB2 can synthesize virus mRNA in vitro (Honda, Mizumoto et al. 2002), but further studies in which the recombinant polymerase was expressed and purified using 293 cell revealed that all three subuits are necessary for replication and transcription (Deng, Sharps et al. 2006). The idea that PA (SEQ ID NO:1) principally participates in the replication process of virus RNA is derived from a finding that a tempreture sensitive mutant (L226P) can result in replication disorder of virus genome under non-permissible temperatures without affecting transcription activity (Kawaguchi, Naito et al.2005); whereas PB2 is involved in virus mRNA transcription. Further studies found that PA (SEQ ID NO:1) can extensively take part in processes such as transcription, replication and virus stability (Hara, Schmidt et al. 2006). The PB1 (SEQ ID NO:2)/PA (SEQ ID NO:1) complex can bind the 5' terminal virus promoter, but PB1 (SEQ ID NO:2) by itself does not bind that promoter. Cross-linking experiments indicate that PA (SEQ ID NO:1) can bind vRNA and cRNA promoters (Fodor, Pritlove et al. 1994; Deng, Sharps et al. 2005; Hara, Schmidt et al. 2006) (Fodor 1994, Gonzalez 1999, Jung 2006, Hara 2006), but the specific binding sites are not clear. PA (SEQ ID NO:1) was found to have similar protease activity as chymotrypsins. Sanz-Ezquerro et al. (1996) found that about 250 amino acids at N-terminal are the active region of that protease—(Sanz-Ezquerro, Zurcher et al. 1996). But subsequently the studies by Hara et al. (2001) showed that the Serine at position 624 of C-terminal was the active site of PA (SEQ ID NO:1) protease, as mutation at that site resulted in loss of protease activity (Hara, Shiota et al. 2001). There is still controversy about the effect of PA (SEQ ID NO:1) protease activity on polymerase function. Hara et al. (2006) reported that purified recombinant PA (SEQ ID NO:1) protein can be degraded into two fragments with molecular weight of ~25 kDa and ~55 kDa through trypsin hydrolysis (Hara, Schmidt et al. 2006). It is known that understanding the three-dimensional structure of a protein is of great help to perform rational drug design, so identifying the three-dimensional structure of PA (SEQ ID NO:1) is of important value to perform drug design and function studies. In addition, previous studies have not reported the expression and purification of influenza virus protein PA (SEQ ID NO:1) in bacteria, so expression and purification of proteins in bacteria is of important benefit to further explore the function of PA (SEQ ID NO:1) and to perform drug screening, thus saving much time and greatly decreasing job cost and labour intensity.

SUMMARY OF THE INVENTION

The present invention provides a method of dividing the wild type or mutant protein of influenza virus polymerase complex subunit PA (SEQ ID NO:1) into N-terminal and C-terminal parts, and cloning and expressing said parts respectively; and a method of expressing, purifying and crystallizing an N-terminal part of PA (SEQ ID NO:1); and a method of expressing a short N-terminal peptide of wild type or mutant protein of influenza virus polymerase subunit PB1 (SEQ ID NO:2); and a method of co-purification of a PA C-terminal and a short N-terminal peptide of PB1. According to the invention, the method of expressing and co-purifying the complex of the first 256 N-terminal amino acids of PA (SEQ ID NO:1) as well of the C-terminal amino acids 257-716 of PA (SEQ ID NO:1) and the N-terminal 25 amino acids of of PB1, and a method of crystallizing a protein complex of the C-terminal part of PA (SEQ ID NO:1) and the N-terminal peptide of PB1 as well as the three-dimensional crystal structure of the resulting complex.

In one aspect, the present invention provides a method of dividing the wild type or mutant protein of influenza virus polymerase complex subunit PA (SEQ ID NO:1) into an N-terminal part and a C-terminal part as well as cloning and expressing these parts respectively; and a method of expressing, purifying and crystallizing an N-terminal part of PA (SEQ ID NO:1); and a method of expressing an N-terminal polypeptide of a wild type or a mutant protein of influenza virus polymerase subunit PB1 (SEQ ID NO:2) and co-purifying the complex of a C-terminal part of PA (SEQ ID NO:1) and an N-terminal short peptide of PB1 for crystallization. In the present invention, preferably a prokaryotic cell expression system of *E.coli* is used, but other expression systems are not excluded, for example, expression can also be performed in other bacteria or other eukaryotic cells. To express the above-mentioned polypeptides as GST (glutathione-S-transferase) fusion proteins, bacteria expressing the PA (SEQ ID NO:1) C-terminal part are combined with bacteria expressing the PB1 N-terminal peptide. This protein complex comprising the above-mentioned C-terminal part of PA (SEQ ID NO:1) and short N-terminal peptide of PB1 is purified from bacterial expression system, for use in protein crystallization. According to the invention, an expression method of obtaining the first 256 N-terminal amino acids of influenza virus polymerase subunit PA (SEQ ID NO:1) and the C-terminal 257-716 amino acids of influenza virus polymerase subunit PA (SEQ ID NO:1) by expression in *E.coli* and a method of obtaining a microbial population of *E.coli* which expresses the polypeptide within the 25 or 48 N-terminal amino acids of influenza virus protein PB1 are described, wherein the methods comprise expressing GST (glutathione-S-transferase)-fused fusion proteins by cloning corresponding genes into pGEX-6p vector.

In another aspect, the present invention provides a method of purifying the complex of a C-terminal part of PA (SEQ ID NO:1) (PAc) and $PB1_N$ peptides, comprising: a microbial population expressing the C-terminal amino acids 257-716 of influenza virus PA (SEQ ID NO:1) and a microbial population expressing a short peptide within the 25 to 48 N-terminal amino acids of the of influenza virus PB1 suspended in medium respectively; combining said peptide-expressing bacteria in in such proportion as to generate a desired molar ratio between the total protein content of GST-PAc and GST-$PB1_N$, thereby obtaining a mixture of these two proteins; purifying the protein mixture by affinity column and cleaving the GST fusion protein by PreScission protease; and obtaining a purified complex of C-terminal PA and N-terminal PB1 peptides by methods such as gel filtration and ion exchange chromatography; wherein the protein purity and concentration can be determined by gel electrophoresis.

In another aspect, the present invention provides a method of crystalizing the complex of PAc and $PB1_N$ peptide obtained as described above, comprising: concentrating the complex of PAc and $PB1_N$ peptide to a concentration of 5-30 mg/ml; screening crystal growth conditions by gas hanging drop at 4-30° C.; and obtaining a crystal of the protein complex.

In another aspect, the present invention provides the crystal of the complex of a PAc and a $PB1_N$ peptide.

In another aspect, the present invention provides the three-dimensional crystal structure of the complex of a Pac peptide and a $PB1_N$ peptide, wherein the structure describes the interaction mode between PAc and $PB1_N$ and corresponding interaction sites, and further describes the composition of secondary structure, peptide side chain orientation and the three-dimensional molecular structure of polypeptides in the complex, wherein X-ray crystal diffraction was performed with the the crystal of the complex of PAc and $PB1_N$ peptide in order to obtain the diffraction data from the protein crystal of the complex of PAc and PB1 N-terminal peptide, and wherein a three-dimensional structure model of the complex of PAc and $PB1_N$ peptide is constructed by further performing a structure analysis process with the diffraction data of the protein crystal.

In one embodiment, the present invention provides a three-dimensional crystal structure of a complex of a C-terminal part of influenza virus polymerase subunit PA-PAc and an N-terminal part of influenza virus polymerase subunit PB1-$PB1_N$, wherein the C-terminal part of the influenza virus polymerase subunit PA-PAc comprises amino acids from about amino acid position 201-301 to about 650-terminus, wherein the N-terminal part of of influenza virus polymerase subunit PB1-$PB1_N$ is a short peptide within the 48 N-terminal amino acids of the of influenza virus polymerase subunit PB1-$PB1_N$, wherein atoms of the three-dimensional crystal structure of the complex have at least partially the atomic coordinates listed in table 1, or any structure that has an average root mean square deviation (RMSD) smaller than or equal to 1.7 Angstrom with atomic coordinates of main chain backbone carbon atoms of at least 40% amino acids in the three-dimensional crystal structure of the complex.

Preferably, the crystal of a complex of a C-terminal part of influenza virus polymerase subunit PA-PAc and an N-terminal part of influenza virus polymerase subunit PB1-$PB1_N$ has a space group of P4(1)2(1)2, and the lattice parameters are about: a=b=122 Angstrom, c=133 Angstrom, $\alpha=\beta=\gamma=90°$.

In one embodiment, the influenza virus is selected from influenza virus A, B and C type, preferably influenza virus A type: A/goose/Guangdong/1/96, A/Brevig Mission/1/1918; influenza virus B type: B/Ann Arbor/1/1966 or influenza virus C type: C/JJ/1950.

In one embodiment, the C-terminal part of influenza virus A polymerase subunit PA-PAc consists of a first portion (i.e. constituting the "mouth" section of the crystal structure, as shown in FIG. 4) and a second portion (i.e. constituting the "head" section of the crystal structure, as shown in FIG. 4), wherein the first portion comprises α helix 4, i.e. a fragment of amino acid positions 406-414, α helix 5, i.e. a fragment of amino acid positions 440-450, α helix 8, i.e. a fragment of amino acid positions 583-603, α helix 9, i.e. a fragment of amino acid positions 608-613, α helix 10, i.e. a fragment of amino acid positions 663-649, α helix 11, i.e. a fragment of amino acid positions 653-673, α helix 12, i.e. a fragment of amino acid positions 683-691, α helix 13, i.e. a fragment of amino acid positions 698-714, β sheet 8, i.e. a fragment of amino acid positions 619-623 and β sheet 9, i.e. a fragment of amino acid positions 628-631; wherein the second portion comprises α helix 1, i.e. a fragment of amino acid positions 303-311, α helix 2, i.e. a fragment of amino acid positions 331-349, α helix 3, i.e. a fragment of amino acid positions 364-369, α helix 6, i.e. a fragment of amino acid positions 454-475 and α helix 7, i.e. a fragment of amino acid positions 572-578, β sheet 1, i.e. amino acids fragment of 290-292 positions, β sheet 2, i.e. a fragment of amino acid positions 317-324, β sheet 3, i.e. a fragment of amino acid positions 480-491, β sheet 4, i.e. a fragment of amino acid positions 496-506, β sheet 5, i.e. a fragment of amino acid positions 517-526, β sheet 6, i.e. a fragment of amino acid positions 541-550 and β sheet 7, i.e. a fragment of amino acid positions 557-571 positions; wherein the β sheets of the second portion of the C-terminal of PA-PAc are surrounded by α helix 1, i.e. a fragment of amino acid positions 303-311, α helix 2, i.e. a fragment of amino acid positions 331-349, α helix 3, i.e. a fragment of amino acid positions 364-369, α helix 6, i.e. a fragment of amino acid positions 454-475 and α helix 7, i.e. a fragment of amino acid positions 572-578, wherein fragments of influenza virus B and C type corresponding to α helixes and β sheets of influenza virus A type are shown in FIGS. 1A, 1B, 1C and FIGS. 10A, 10B, respectively.

In one embodiment, the C-terminal part of influenza virus type A polymerase subunit PA-PAc interacts with the N-terminal part of PB1-PB1$_N$ mainly through α helix 8, α helix 10, α helix 11 and α helix 13, preferably mediated by at least one amino acid selected from a group consisting of Leu666 of α helix 11, Phe710 of α helix 13, Val636 of α helix 10, Leu640 of α helix 10, Trp706 of α helix 13 and Gln670 of α helix 11, and wherein fragments of influenza virus B and C type corresponding to these α helixes of influenza virus A type are shown in FIGS. 1A, 1B, 1C and FIGS. 10A, FIGS. 10B, respectively.

In one embodiment, at least one amino acid selected from the group consisting of Ile621, Gly622, Glu623, Thr618 and Pro620 interacts with the influenza virus polymerase subunit PB1, where the Ile621, Gly622, Glu623, Thr618 and/or Pro620 is in the peptide loop between α helix 9 and α helix 10 of the C-terminal of the influenza virus A polymerase subunit PA-PAc, and wherein the fragments of influenza virus B and C type corresponding to the α helixes of influenza virus A type are shown in FIGS. 1A, 1B, and 1C and FIGS. 10A, and 10B respectively.

In one embodiment, a "pocket" structure comprising at least one amino acid selected from the group consisting of Asn647, Gln408, Cys584, Gln587, Gln591, Lys643, Asn647, Ser659, Lys663, Trp699 and Asn703 of the C-terminal of influenza virus A polymerase subunit PA-Pac is provided, where such "pocket" structure binds the influenza virus polymerase subunit PB1$_N$, and wherein the fragments of influenza virus B and C type corresponding to such influenza virus A type fragments are shown in FIGS. 1A, 1B, 1C and FIGS. 10A, 10B respectively.

In one embodiment, "groove" and "channel" structures comprising at least one amino acid selected from the group consisting of Trp406, Glu410, Lys461, Glu524, Phe525, Ser526, Lys536, Lys539, Tyr540, Leu563, Tyr564, Arg566 and Lys574 of the C-terminal of the influenza virus A polymerase subunit PA-Pac are provided, where such "groove" and "channel" structures bind nucleotides, RNA or other small molecules or proteins, and wherein the fragments of influenza virus B and C type corresponding to this influenza virus A type fragment are shown in FIGS. 1A, 1B, 1C and FIGS. 10A, 10B respectively.

In one embodiment, amino acid residues at positions 370-405 of the C-terminal part of PA-PAc constitutes a large loop, wherein the fragments of influenza virus B and C type corresponding to this influenza virus A type fragment are shown in FIGS. 1A, 1B, 1C and FIGS. 10A, 10B respectively.

In one embodiment, α helix 12 and α helix 13, preferably at least one amino acid selected from the group consisting of Ile690, Glu691, Glu692, Cys693 and Asn696 of the α helix 12 and α helix 13, interacts with other proteins.

In one embodiment, at least one amino acid selected from the group consisting of Lys506, Gly507, Arg508, Ser509, His510, Leu511, Arg512, Asn513 and Asp514 interacts with other proteins, wherein His510 constitutes a portion of the polymerase complex RNAse, and wherein the fragments of influenza virus B and C type corresponding to influenza virus A type are shown in FIGS. 1A, 1B, 1C and FIGS. 10A, 10B respectively.

In one embodiment, the present invention provides a polypeptide, protein, inorganic compound or organic compound, which binds to at least one member selected from the group consisting of α helix 8, α helix 10, α helix 11 and α helix 13 of a C-terminal part of influenza virus subunit PA-PAc, and which preferably binds to the member selected from the group consisting of Leu666 in α helix 11, Phe710 in α helix 13, Val636 and Leu640 in α helix 10, Trp706 in α helix 13, Gln670 in α helix 11 of N-terminal of influenza virus subunit PA-PAc, wherein fragments of influenza virus B and C type corresponding to influenza virus A are shown in FIGS. 1A, 1B, 1C and FIGS. 10A, 10B respectively.

In one embodiment, the present invention provides a polypeptide, protein, inorganic compound or organic compound, antibody or immunoconjugate binding to at least one member selected from the group consisting of Ile621, Gly622, Glu623, Thr618 and Pro620 located at the peptide loop between α helix 9 and α helix 10 of a C-terminal part of influenza virus polymerase subunit PA-PAc, wherein fragments of influenza virus B and C type corresponding to influenza virus A type are shown in FIGS. 1A, 1B, 1C and FIGS. 10A, 10B respectively.

In one embodiment, the present invention provides a polypeptide, protein, inorganic compound or organic compound, antibody or immunoconjugate binding to at least one amino acid selected from the group consisting of Asn647, Gln408, Cys584, Gln587, Gln591, Lys643, Asn647, Ser659, Lys663, Trp699 and Asn703 of a C-terminal part of influenza virus A polymerase subunit PA-PAc, wherein fragments of influenza virus B and C type corresponding to influenza virus A type are shown in FIGS. 1A, 1B, 1C and FIGS. 10A, 10B respectively.

In one embodiment, the present invention provides a polypeptide, protein, inorganic compound or organic compound, antibody or immunoconjugate binding to at least one amino acid selected from the group consisting of Trp406, Glu410, Lys461, Glu524, Phe525, Ser526, Lys536, Lys539, Tyr540, Leu563, Tyr564, Arg566 and Lys574 of a C-terminal part of influenza virus A polymerase subunit PA-PAc, wherein fragments of influenza virus B and C type corresponding to influenza virus A type are shown in FIGS. 1A, 1B, 1C and FIGS. 10A, 10B respectively.

In one embodiment, the present invention provides a polypeptide, protein, inorganic compound or organic compound, antibody or immunoconjugate binding to amino acid positions 370-405 of a C-terminal part of influenza virus A polymerase subunit PA-PAc, wherein fragments of influenza virus B and C type corresponding to influenza virus A type are shown in FIGS. 1A, 1B, 1C and FIGS. 10A, 10B respectively.

In one embodiment, the present invention provides a polypeptide, protein, inorganic compound or organic compound, antibody or immunoconjugate binding to helix 12 and α helix 13 of a C-terminal part of influenza virus A polymerase subunit PA-PAc, preferably to at least one amino acid selected from the group consisting of Ile690, Glu691, Glu692, Cys693 and Asn696 in α helix 12 and α helix 13, wherein corresponding fragments of influenza virus B and C type to influenza virus A type are shown in FIGS. 1A, 1B, 1C and FIGS. 10A, 10B respectively.

In one embodiment, the present invention provides a polypeptide, protein, inorganic compound or organic compound, antibody or immunoconjugate binding to at least one amino acid selected from the group consisting of Lys506, Gly507, Arg508, Ser509, His510, Leu511, Arg512, Asn513 and Asp514 located at loop region between sheet β 4 and sheet β 5 in the C-terminal of influenza virus A polymerase subunit PA-PAc, wherein fragments of influenza virus B and C type corresponding to influenza virus A type are shown in FIGS. 1A, 1B, 1C and FIGS. 10A, 10B respectively.

In one embodiment, the present invention provides a polypeptide, protein, inorganic compound or organic compound, antibody or immunoconjugate which competes with influenza virus polymerase subunit PB1 (SEQ ID NO:2) for binding PAc, wherein fragments of influenza virus B and C type corresponding to influenza virus A type are shown in FIGS. 1A, 1B, 1C and FIGS. 10A, 10B respectively.

In one embodiment, the present invention provides a PAc protein interaction domain comprising a hydrophobic core constituted by the α helix 8, α helix 11, α helix 13 and α helix 10, particularly the interaction domain comprises Met595 in α helix 8, Leu666 in α helix 11, Trp706 and Phe710 in α helix 13, Val636 and Val640 in α helix 10, wherein fragments of influenza virus B and C type corresponding to influenza virus A type are shown in FIGS. 1A, 1B, 1C and FIGS. 10A, 10B respectively.

In one embodiment, the present invention provides a polypeptide, protein, inorganic compound or organic compound, antibody or immunoconjugate which competes with influenza virus polymerase subunit PB1 (SEQ ID NO:2) for binding PAc, wherein the amino acid sequence of the polypeptide, protein, antibody or immunoconjugate comprises at least three amino acids which are identical to amino acids of corresponding position of a short PTLLFL motif of the short helix domain constituted by the 5th-10th residues Pro5, Thr6, Leu7, Leu8, Phe9 and Leu10 of the N-terminal part of wild influenza virus polymerase subunit PB1-PB1$_N$, when the polypeptide or protein is aligned with the PTLLFL motif.

In one embodiment, the present invention provides a composition comprising the above-mentioned polypeptide, protein, inorganic compound or organic compound, antibody or immunoconjugate.

In one embodiment, the present invention provides use of the above-mentioned composition in the manufacture of a medicament for the treatment of diseases caused by influenza virus.

In one embodiment, the present invention provides a method of expressing and purifying the complex of a C-terminal part of influenza virus polymerase subunit PA-PAc and an N-terminal part of influenza virus polymerase subunit PB1-PB1$_N$, comprising: (a) constructing a vector with a gene sequence encoding amino acid from about positions 201-301 to about 650 terminus of a C-terminal part of influenza virus polymerase subunit PA-PAc, where the vector may further comprise a protein tag tag fusion, wherein prokaryotic or eukaryotic cells transformed with said vector comprising the protein tag and the PA-PAc sequence can express PAc as a tagged fusion protein; (b) using a method analogous to the method of expressing PAc to express the PB1$_N$ with or without a protein tag; (c) Proportionally mixing the cell expressing influenza virus polymerase subunit PAc obtained from step (a) and the cell expressing amino acids within the 48 amino acids of the N-terminal of influenza virus polymerase subunit PB1 obtained from step (b), wherein the resulting protein is isolated by the specific recognition of the specific tag, the protein tag is removed from the protein by enzymolysis, the complex of PAc and PB1$_N$ is isolated, and the concentration of the complex is determined;

The atoms of the three-dimensional crystal structure of a complex of a C-terminal part of influenza virus polymerase subunit PA-PAc and an N-terminal part of influenza virus polymerase subunit PB1-PB1$_N$ have at least 40% of the atomic coordinates listed in table 1, or atomic coordinates of main chain backbone carbons of at least 40% amino acids in the crystal three-dimensional structure of complex of a C-terminal part of influenza virus polymerase subunit PA-PAc and an N-terminal part of influenza virus polymerase subunit PB1-PB1$_N$ have an average root mean square deviation smaller than or equal to 1.7 Angstrom with respect to the atomic coordinates listed in table 1.

In one embodiment, the present invention provides a method of expressing and purifying the complex of an C-terminal part of influenza virus polymerase subunit PA-PAc and a N-terminal part of influenza virus polymerase subunit PB1-PB1$_N$, wherein a protein tag is selected from GST, Flag-tag, Myc-tag, MBP-tag, specific antibodies?; the vector comprises a selection marker gene; the proportional mixing in step (c) above means that the molar ratio of protein-tagged PAc and protein-tagged PB1$_N$ is 0.1:1-1:0.1, preferably the molar ratio of protein-tagged PAc and protein-tagged PB1$_N$ is 0.5:1-1:0.5, more preferably the molar ratio of protein-tagged PAc and protein-tagged PB1$_N$ is nearly 1:1; wherein preferably the protein tag is GST, wherein the tag is specifically recognized using an affinity column, wherein the tag is removed by proteinases, wherein the complex of PAc and PB1$_N$ is separated by gel filtration or ion-exchange chromatography, and wherein the the protein concentration is determined by gel electrophoresis.

In one embodiment, the present invention provides a method of expressing and purifying the complex of a C-terminal part of influenza virus polymerase subunit PA-PAc and an N-terminal part of influenza virus polymerase subunit PB1-PB1$_N$, wherein the vector is pGEX-6p plasmid vector, and said selective marker gene is penicillin resistance gene, and the proteinase used in step (c) is PreScission proteinase; the restriction site in primers that is employed in the vector is a restriction site selected from a group consisting of SalI and NotI; the restriction site used to insert a gene fragment is a restriction site selected from a group consisting of SalI and NotI; said gene fragment of a C-terminal part of influenza virus polymerase subunit PA-PAc is obtained from the genome of influenza virus A type: A/goose/Guangdong/1/96 by polymerase chain reaction (PCR); said vector and said gene fragment to be inserted are treated by corresponding DNA restriction enzyme respectively, such as those selected from a group consisting of BamHI and XhoI, and ligating the gene to be inserted and the vector by T4 DNA ligase, before transforming prokaryotic cells such as E. coli to obtain cloned plasimds. The cloned plasmid as described above are transformed into E. coli BL21, the resulting transformed bacteria are cultured and induced by using IPTG, wherein the preferred concentration of IPTG is 0.1 mM to 1 mM, and the cultured bacteria are centrifuged to obtain the microbial population that express said fusion protein.

In one embodiment, the present invention provides a method of co-crystallizing the complex of a C-terminal part of influenza virus polymerase subunit PA-PAc and an N-terminal part of influenza virus polymerase subunit PB1-PB1$_N$, comprising: concentrating the protein concentration of the purified complex of PAc and PB1$_N$ to 5-30 mg/ml; screening crystal growth conditions by gas sitting drop or hanging drop method; and obtaining the crystal of a complex of a C-terminal part of influenza virus polymerase subunit PA-PAc and an N-terminal part of influenza virus polymerase subunit PB1-PB1$_N$.

In one embodiment, the present invention provides a method of expressing wild type or mutant protein of an N-terminal part of PA-PA$_N$, wherein PA$_N$ comprises amino acids from positions 1-50 to about 200-300, the method comprising: constructing an expression vector with a gene sequence encoding amino acids from positions 1-50 to about 200-300 of an N-terminal part of influenza virus polymerase subunit PA-PA$_N$, wherein the vector comprises a protein tag, and transforming cells with the expression vector in order to express tagged PA$_N$ fusion protein, wherein the N-terminal part of PA-PA$_N$ has at least 40% sequence identity with the amino acids listed in FIG. 1C.

In one embodiment, the present invention provides a method of expressing wild type or mutant protein of an N-terminal part of PA-PA$_N$, wherein gene sequence of the N-terminal part of polymerase subunit PA-PA$_N$ is cloned into plasmid vectors for example, a series of pGEX vectors such as pGEX-6p, pGEX-4 T (Amersham Pharmacia), a series of pET vectors (Novagen) and a series of pMAL-c2 (Invitrogen) to express a fusion protein GST-PA$_N$ wherein the N-terminus of PA$_N$ is fused to GST; wherein the plasmid vector comprises a penicillin resistance gene and a restriction site employed when cloning the vector with the gene of an N-terminal polypeptide of PA-PA$_N$, wherein the restriction site is selected from a group consisting of BamHI and XhoI from multiple cloning sites in pGEX-6p; the restriction site used for cloning a PA$_N$ gene fragment is BamHI and XhoI; amplifying a gene fragment of PA$_N$ protein from the genome of influenza virus A type: A/goose/Guangdong/1/96 by polymerase chain reaction (PCR) method; treating the vector and the inserted gene fragment with corresponding DNA restriction enzymes respectively, such as those selected from a group consisting of BamHI and XhoI, and ligating gene to be inserted and the vector by T4 DNA ligase, before transforming E. coli to obtain cloned plasmids. The cloned plasmid as described above is transformed into E. coli BL21, the resulting transformed bacteria are cultured and induced by using 0.1 mM to 1 mM IPTG, and the cultured bacteria are centrifuged to obtain the microbial population that express said fusion protein.

In one embodiment, the present invention provides a method of screening candidate compounds which compete with PB1$_N$ for binding PAc, the method comprising: (a) attaching PAc to the surface of a fixed support; (b) contacting an excess of tagged PB1$_N$ with the attached PAc; (c) eluting thoroughly with an eluent in order to remove un-bound PB1$_N$; (d) contacting a solution with the candidate compound to be detected with the attached PAc with bound PB1$_N$; (e) eluting thoroughly with an eluent in order to obtain a solution to be detected; (f) measuring the concentration of free tagged PB1$_N$ in the solution to be detected; (g) calculating the binding capability of the candidate compound to be detected with PAc according to the concentration of free tagged PB1$_N$ in the solution to be detected.

In one embodiment, the present invention provides a method of screening candidate compounds which compete with PB1$_N$ for binding PAc, wherein attaching PAc to surface of the fixed support in step (a) is achieved by covalently cross-linking or binding PAc with an affinity tag, and determining binding of PAc to the corresponding affinity group attached to the surface of the fixed support.

In one embodiment, the present invention provides a method of screening candidate compounds which compete with PB1$_N$ for binding PAc, utilizing an affinity tag such as GST, Flag-tag, Myc-tag, MPB-tag and specific antibody, and wherein the corresponding affinity group is attached to the surface of the fixed support.

In one embodiment, the present invention provides a method of screening candidate compounds which compete with PB1$_N$ for binding PAc, wherein the tagged PB1$_N$ polypeptide is selected from a protein tagged with an isotope or a protein tagged with other molecules, preferably wherein the other molecular tag is green fluorescent protein or various fusion polypeptides, e.g. binding peroxidase, phosphohydrolase, protein kinase, various group transferase.

In one embodiment, the present invention provides a method of screening candidate compounds which compete with PB1$_N$ for binding PAc, wherein the fixed surface is an affinity chromatography column.

In one embodiment, the present invention provides the use of the three-dimensional crystal structure of a complex of a C-terminal part of influenza virus polymerase subunit PA-PAc and N-terminal of influenza virus polymerase subunit PB1-PB1$_N$ in designing and screening a polypeptide, protein, inorganic compound or organic compound, antibody or immunoconjugate used in the treatment of diseases caused by the influenza virus infection.

Drug screening can be performed based on the above method of expressing and purifying PAc protein; the above method of expressing and purifying the complex of PAc and PB1$_N$ polypeptide and the above method of obtaining protein crystal, and drug design can be performed based on the three-dimensional structure of PAc and PB1$_N$.

In one embodiment, the present invention provides use of the three-dimensional crystal structure of a complex of C-terminal part of influenza virus polymerase subunit PA-PAc and N-terminal part of influenza virus polymerase subunit PB1-PB1$_N$ in designing and screening a polypeptide, protein, inorganic compound or organic compound, antibody or immunoconjugate used in the treatment of diseases caused by the influenza virus infection, comprising:

designing a polypeptide, protein, inorganic compound or organic compound, antibody or immunoconjugate binding to a specific portion of the polymerase subunit by computer simulation according to the coordinates of three-dimensional protein structure;

screening for a potential polypeptide, protein, inorganic compound or organic compound, antibody or immunoconjugate binding to specific portion of the polymerase subunit by computer simulation according to coordinates of three-dimensional protein structure;

analyzing binding characteristics of the designed or searched polypeptide, protein, inorganic compound or organic compound, antibody or immunoconjugate according to the atomic coordinates of the three-dimensional structure of the protein to bind to any subtype of influenza virus polymerase protein which have at least 50% sequence identity with the PAc and the PB1$_N$ sequence;

the designed or searched polypeptide, protein, inorganic compound or organic compound, antibody or immunoconjugate according to coordinates of three-dimensional protein structure bind to any subtype of influenza virus polymerase protein which has at least 50% sequence identity with the PAc and the PB1$_N$ sequence, and then crystallization is preformed, the binding characteristics of polypeptide or compound molecule to protein is analyzed through crystal diffraction method;

wherein a polypeptide, protein, inorganic compound or organic compound, antibody or immunoconjugate which binds to any subtype of influenza virus polymerase protein which has at least 50% sequence identity with the PAc and the PB1$_N$ sequence is a candidate compound.

To reveal the role of PA (SEQ ID NO:1) in polymerase and its fine three-dimensional structure, the inventors analyzed the crystal structure with a resolution of 2.9 Angstrom of the complex of a C-terminal fragment of residues 257-716 of PA (PA$_C$) and the N-terminal 25 residues of PB1 (PB1$_N$). This structure clearly indicates the interaction mode between the C-terminal part of PA (SEQ ID NO:1) and the N-terminal part of PB1 as well as the composition of amino acid residues that participate in the interaction and their relative spatial positions. The inventors also determined the three-dimensional structure of the complex of the C-terminal part of PA (SEQ ID NO:1) and the N-terminal part of PB1, the composition of secondary structure of the protein, the binding sites of nucleic acid in the PA (SEQ ID NO:1) protein, a small-molecule channel in the PA (SEQ ID NO:1) protein and the charge distribution on the surface of the PA (SEQ ID NO:1) protein, providing a structural basis for investigating the role of PA (SEQ ID NO:1) in the complex of virus RNA polymerase, and providing a protein crystallization? platform and a three-dimensional platform for designing drugs inhibiting interactions between PA (SEQ ID NO:1) and PB1, as well as interactions between PA (SEQ ID NO:1) and RNA or other proteins, to inhibit the activity of the influenza virus polymerase.

It should be noted that the amino acid sequences of the corresponding fragments in influenza virus B and C types relative to α helixes and β sheets of influenza virus A type are shown in FIGS. 1A, 1B, 1C and FIGS. 10A, 10B respectively, which is not listed in detail.

BRIEF DESCRIPTION OF THE DRAWINGS

This patent application file contains at least one drawing executed in color. Copies of this patent application publication with color drawings will be provided by the Office upon request and with payment of the necessary fee.

Figure 1A:
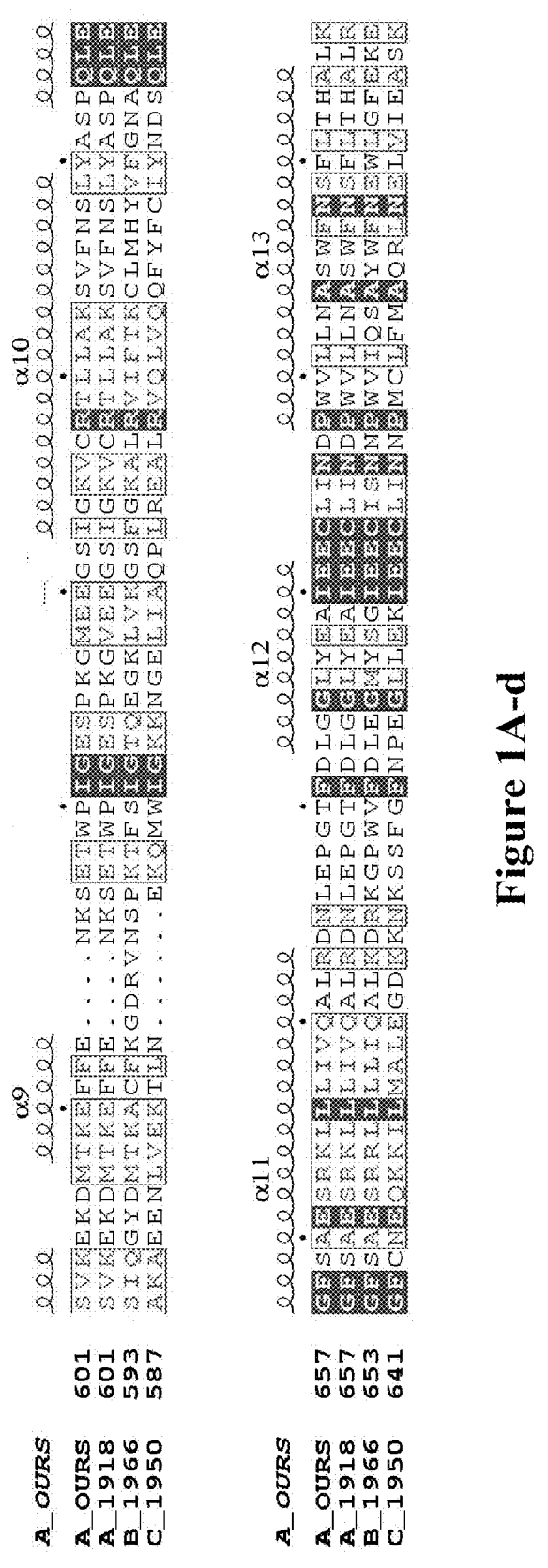

FIGS. 1A-*a* through 1A-*d*, 1B, and 1C-*a* through 1C-*c*: Sequence of the C-terminal of PA and the protein sequence of $PB1_N$ from three types of influenza virus. FIGS. 1A-*a* through 1A-*d*. Sequence alignment of PA protein from three types of influenza virus, wherein A_OURS is the sequence of the C-terminal of the PA protein from influenza virus A type: A/goose/Guangdong/1/96 (SEQ ID NO:1); A__1918 is the sequence of the PA protein from the influenza virus A type: A/Brevig Mission/1/1918 (SEQ ID NO:3), which is the cause of a widespread influenza outbreak and a great death event in Europe in 1918; B__1966 is the sequence of the PA protein from the influenza virus B type: B/Ann Arbor/1/1966 (SEQ ID NO:4); C__1950 is the sequence of the PA protein from the influenza virus C type: C/JJ/1950 (SEQ ID NO:5); this result indicates that the protein of influenza virus polymerase subunit PA has highly conservative amino acid residues. FIG. 1B. Sequence alignment of the $PB1_N$ protein from four type of influenza virus, wherein A_OURS (SEQ ID NO:2), A__1918 (SEQ ID NO:6), B__1966 (SEQ ID NO:7), C__1950 (SEQ ID NO:8) are as described above. In these figures, ". . . " is used to indicate amino acid deletion in corresponding fragments. Specific amino acid positions in the specification and claims are illustrated by the example of A_OURS (SEQ IDS NO:1 and 2).

FIGS. 1C-*a* through 1C-*d*: Sequence of the N-terminal of the PA protein from three types of influenza viruses, wherein A_OURS (SEQ ID NO:1), A__1918 (SEQ ID NO:3), B__1966 (SEQ ID NO:4), C__1950 (SEQ ID NO:5) are as described above. In these figures, ". . . " is used to indicate amino acid deletion in the corresponding fragments. Specific amino acid positions in the specification and claims are illustrated by the example of A_OURS (SEQ ID NO:1).

FIG. 2: Purification of a polypeptide fragment of the former 256 amino acid in PA N-terminal of influenza virus A type: A/goose/Guangdong/1/96, wherein A shows the peak of purified protein during gel filtration chromatography Superdex-200 (Amersham Pharmacia Inc.). B represents electrophoresis result from PA N-terminal of corresponding peak. C is the finally purified protein of PA N-terminal.

FIG. 3: Protein crystallization and diffraction obtained from purified protein of PA N-terminal (1-256 residues), wherein A and B are crystals obtained under different crystallization conditions; and C and D show X-ray diffraction pattern of two protein crystals from PA N-terminal.

FIG. 4: PAc and GST-$PB1_N$ protein expressed and purified in *E.coli*, and interaction experiment between PAc and PB1 N-terminal peptide, and ribbon image of structure of the complex between purified PAc and $PB1_N$ polypeptide. A. purified PAc protein, and in vitro interaction experiment between purified PAc and PB1 N-terminal peptide. B. Diagram of three-dimensional structure of the complex between PAc and $PB1_N$ polypeptide, which shows a overall structure of chewing wolf's head.

FIG. 5: Overall structure of the complex of C-terminal of PA and N-terminal of PB1, wherein: A. side view of overall structure of the complex of PAc and $PB1_N$, to clearly show the direction of protein chain; B. Image in FIG. 5(A) is rotated by 180°, wherein secondary structure is marked, and the two ends of PB1 N-terminal peptide and PAc is indicated by arrows.

FIG. 6: Interaction between PAc and $PB1_N$ polypeptide, wherein: A. surface image of PA (SEQ ID NO:1) protein molecule; N-terminal polypeptide of PB1 is illustrated by ribbon image, whereas PA (SEQ ID NO:1) molecule is illustrated by surface charge distribution. B. zoomed to observe that interaction between PA (SEQ ID NO:1) and PB1 is mainly through hydrophobic interaction.

FIG. 7: Surface charge pattern of PA (SEQ ID NO:1) protein molecule, wherein A and B are consistent with the direction of A and B in FIG. 5 respectively.

FIG. 8: Schematic diagrams of big groove and channel present in molecular structure of PAc/$PB1_N$ complex. A illustrates the big groove, and some alkaline amino acids residues are marked. B and C are drawings of channel observed from the two sides respectively (rotate 180° about X axis). Some reserved amino acids in or around the channel are marked.

FIG. 9: Illustration of interaction between PA-C and PB1-N: A. ribbon image of the three-dimensional structure of the complex between PA-C and PB1-N polypeptide; B. surface image of the PA (SEQ ID NO:1) protein molecule. The N-terminal polypeptide of PB1 is illustrated by a ribbon image, whereas the PA (SEQ ID NO:1) molecule is illustrated by a surface charge distribution. C. Expanded view of a part of the complex to observe that helices 8, 10, 11 and 13 of the PA (SEQ ID NO:1) molecule interact with the PB1 polypeptide. D. Expanded view of the interaction between PA (SEQ ID NO:1) and PB1. N-terminal polypeptide of PB1 is illustrated by ribbon image, whereas PA (SEQ ID NO:1) molecule is illustrated by surface charge distribution. The two polypeptides bind mainly through hydrophobic interaction.

Figure 10:
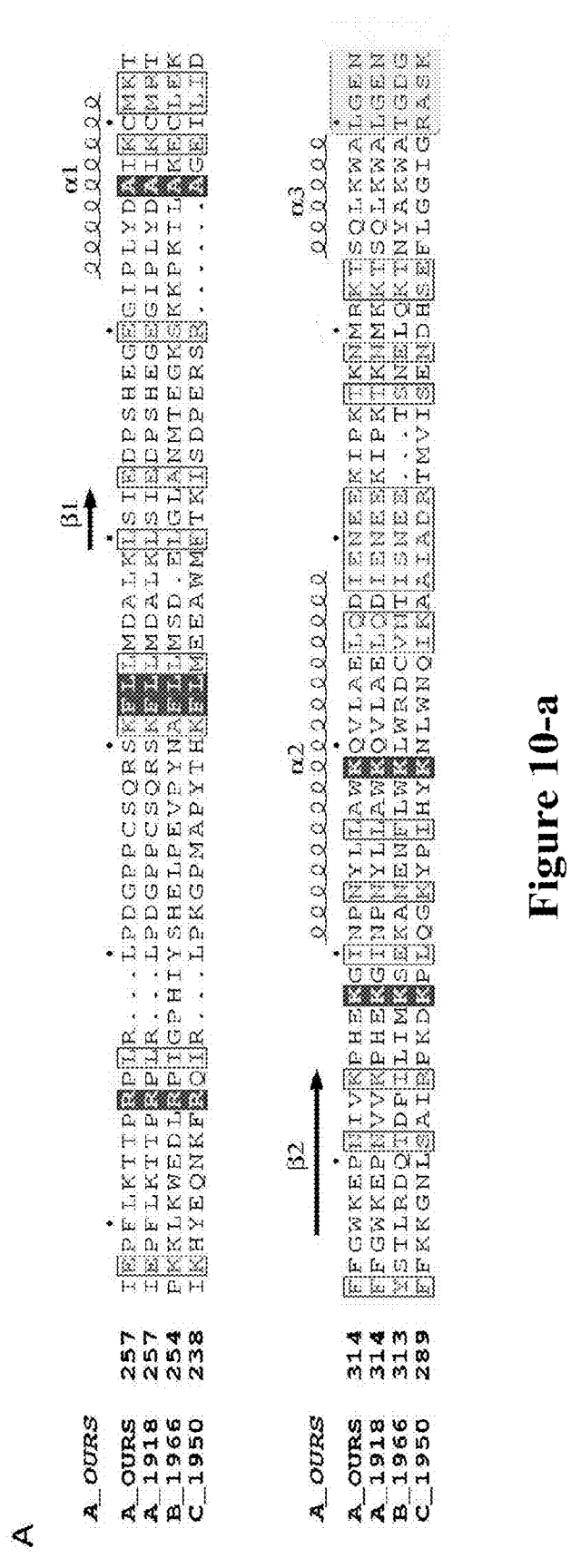

FIGS. 10-*a* through 10-*e*: As described in FIGS. 1A-*a* through 1A-*d* and 1B: Sequence of the C-terminal of PA and the protein sequence of $PB1_N$ from three types of influenza virus. FIGS. 10-*a* through 10-*d*. Sequence alignment of PA protein from three types of influenza virus, wherein A_OURS is the sequence of the C-terminal of the PA protein from influenza virus A type: A/goose/Guangdong/1/96 (SEQ ID NO:1); A__1918 is the sequence of the PA protein from the influenza virus A type: A/Brevig Mission/1/1918 (SEQ ID NO:3), which is the cause of a widespread influenza outbreak and a great death event in Europe in 1918; B_1966 is the sequence of the PA protein from the influenza virus B type: B/Ann Arbor/1/1966 (SEQ ID NO:4); C_1950 is the sequence of the PA protein from the influenza virus C type: C/JJ/1950 (SEQ ID NO:5); this result indicates that the protein of influenza virus polymerase subunit PA has highly conservative amino acid residues. FIG. 10-e. Sequence alignment of the PB1$_N$ protein from four type of influenza virus, wherein A_OURS (SEQ ID NO:2), A_1918 (SEQ ID NO:6), B_1966 (SEQ ID NO:7), C_1950 (SEQ ID NO:8) are as described above. In these figures, ". . . " is used to indicate amino acid deletion in corresponding fragments. Specific amino acid positions in the specification and claims are illustrated by the example of A_OURS (SEQ ID NO:2). The box noted with "Round Loop" indicates a big-ring region in the structure, and the other box (unmarked) is a possible nucleic acid binding region. Arrows indicate amino acid residues in PA that participate in binding with the PB1 short peptide. Specific amino acid positions in the specification and claims are illustrated by the example of A_OURS (SEQ IDS NO:1 and 2).

EMBODIMENTS

The present invention provides a method of expressing fragments of wild type or mutant protein of influenza virus polymerase subunit PA (SEQ ID NO:1), wherein an N-terminal part and a C-terminal part are expressed and purified in *E.coli* respectively, comprising: a method of only using an N-terminal part of PA for a crystallization experiment; a method of expressing and purifying a fragment comprising residues 257-716 in the C-terminal part of PA as well as the wild type and mutant protein of the N-terminal part of influenza virus subunit PB1 in *E. coli* respectively. Also provided is a method of crystallizating the complex of a C-terminal part of PA and an N-terminal peptide of PB1, and the crystal structure of complex of PAc/PB1$_N$ short peptide obtained therefrom, and a method of drug screening based on these crystallization methods as well as a method of drug design based on these crystal structures.

In one embodiment, the present invention provides a three-dimensional crystal structure of a complex of a C-terminal part of influenza virus polymerase subunit PA-PAc and an N-terminal part of influenza virus polymerase subunit PB1-PB1$_N$, wherein the C-terminal part of the influenza virus polymerase subunit PA-PAc comprises amino acids from about amino acid position 201-301 to about 650 terminus, wherein the N-terminal part of of influenza virus polymerase subunit PB1-PB1$_N$ is a short peptide within the 48 N-terminal amino acids of the of influenza virus polymerase subunit PB1-PB1$_N$, wherein the atoms of the three-dimensional crystal structure have at least 40% of the atomic coordinates listed in table 1, or the atomic coordinates of main chain backbone carbons of at least 40% of amino acids in the three-dimensional crystal structure of a complex of a C-terminal part of influenza virus polymerase subunit PA-PAc and an N-terminal part of influenza virus polymerase subunit PB1-PB1$_N$ have an average root mean square deviation smaller than or equal to 1.7 Angstrom with respect to the atomic coordinates listed in table 1.

In one embodiment, the present invention provides crystal three-dimensional structure of complex of a C-terminal part of influenza virus polymerase subunit PA-PAc and an N-terminal part of influenza virus polymerase subunit PB1-PB1$_N$, wherein the influenza virus is selected from influenza virus A, B and C type, preferably influenza virus A type: A/goose/ Guangdong/1/96, A/Brevig Mission/1/1918; influenza virus B type: B/Ann Arbor/1/1966 or influenza virus C type: C/JJ/1950.

In a preferred embodiment, the present invention provides a three-dimensional crystal structure of complex of a C-terminal part of influenza virus polymerase subunit PA-PAc and an N-terminal part of influenza virus polymerase subunit PB1-PB1$_N$, wherein the crystal of the complex has a P4(1)2(1)2 space group of and the lattice parameters are about: a=b=122 Angstrom, c=133 Angstrom, α=β=γ=90°.

In a preferred embodiment, the present invention provides a three-dimensional crystal structure of a complex of a C-terminal part of influenza virus polymerase subunit PA-PAc and an N-terminal part of influenza virus polymerase subunit PB1-PB1$_N$, wherein the C-terminal part of influenza virus A polymerase subunit PA-PAc consists of a first portion and a second portion, wherein the first portion comprises α helix 4, i.e. a fragment of amino acid positions 406-414, α helix 5, i.e. a fragment of amino acid positions 440-450, α helix 8, i.e. a fragment of amino acid positions 583-603, α helix 9, i.e. a fragment of amino acid positions 608-613, α helix 10, i.e. a fragment of amino acid positions 633-649, α helix 11, i.e. a fragment of amino acid positions 653-673, α helix 12, i.e. a fragment of amino acid positions 683-691, α helix 13, i.e. a fragment of amino acid positions 698-714, β sheet 8, i.e. a fragment of amino acid positions 619-623 and β sheet 9, i.e. a fragment of amino acid positions 628-631; wherein the second portion comprises α helix 1, i.e. a fragment of amino acid positions 303-311, α helix 2, i.e. a fragment of amino acid positions 331-349, α helix 3, i.e. a fragment of amino acid positions 364-369, α helix 6, i.e. a fragment of amino acid positions 454-475 and α helix 7, i.e. a fragment of amino acid positions 572-578, β sheet 1, i.e. amino acids fragment of 290-292 positions, β sheet 2, i.e. a fragment of amino acid positions 317-324, β sheet 3, i.e. a fragment of amino acid positions 480-491, β sheet 4, i.e. a fragment of amino acid positions 496-506, β sheet 5, i.e. a fragment of amino acid positions 517-526, β sheet 6, i.e. a fragment of amino acid positions 541-550 and β sheet 7, i.e. a fragment of amino acid positions 557-571 positions; wherein the β sheets of the second portion of the C-terminal of PA-PAc is surrounded by α helix 1, α helix 2, α helix 3, α helix 6, and α helix 7, wherein fragments of influenza virus B and C type corresponding to α helixes and β sheets of influenza virus A type are shown in FIGS. 1A, 1B, 1C and FIGS. 10A, 10B, respectively.

In a preferred embodiment, the present invention provides a three-dimensional crystal structure of a complex of a C-terminal part of influenza virus polymerase subunit PA-PAc and an N-terminal part of influenza virus polymerase subunit PB1-PB1$_N$, wherein the C-terminal part of influenza virus A polymerase subunit PA-PAc interacts with the N-terminal part of PB1-PB1$_N$ mainly through α helix 8, α helix 10, α helix 11 and α helix 13, preferably through at least one amino acid selected from a group consisting of Leu666 of α helix 11, Phe710 of α helix 13, Val636 of α helix 10, Leu640 of α helix 10, Trp706 of α helix 13 and Gln670 of α helix 11, wherein amino acids of fragments of influenza virus B and C type corresponding to influenza virus A type are shown in FIGS. 1A, 1B, 1C and FIGS. 10A, 10B respectively.

In a preferred embodiment, the present invention provides a three-dimensional crystal structure of a complex of a C-terminal part of influenza virus polymerase subunit PA-PAc and an N-terminal part of influenza virus polymerase subunit PB1-PB1$_N$, wherein at least one amino acid selected from the group consisting of Ile621, Gly622, Glu623, Thr618 and Pro620 interacts with the influenza virus polymerase subunit PB1, Ile621, Gly622, Glu623, Thr618 and Pro620 being in the peptide loop between α helix 9 and α helix 10 of the C-terminal part of influenza virus A polymerase subunit PA-PAc, wherein amino acids of fragments of influenza virus B and C type corresponding to influenza virus A type are shown in FIGS. 1A, 1B, 1C and FIGS. 10A, 10B respectively.

In a preferred embodiment, the present invention provides a three-dimensional crystal structure of a complex of a C-terminal part of influenza virus polymerase subunit PA-PAc and an N-terminal part of influenza virus polymerase subunit PB1-PB1$_N$, wherein at least one amino acid selected from the group consisting of Asn647, Gln408, Cys584, Gln587, Gln591, Lys643, Asn647, Ser659, Lys663, Trp699 and Asn703 of the C-terminal of influenza virus A polymerase subunit PA-PAc constitutes a "pocket" of amino acid residues which bind the influenza virus polymerase subunit PB1$_N$, wherein amino acids of fragments of influenza virus B and C type corresponding to influenza virus A type are shown in FIGS. 1A, 1B, 1C and FIGS. 10A, 10B respectively.

In a preferred embodiment, the present invention provides a three-dimensional crystal structure of a complex of a C-terminal part of influenza virus polymerase subunit PA-PAc and an N-terminal part of influenza virus polymerase subunit PB1-PB1$_N$, wherein at least one amino acid selected from the group consisting of Trp406, Glu410, Lys461, Glu524, Phe525, Ser526, Lys536, Lys539, Tyr540, Leu563, Tyr564, Arg566 and Lys574 of the C-terminal of influenza virus A polymerase subunit PA-PAc constitutes a large "groove" and a "channel" structure which bind nucleotide, RNA or other small molecules or proteins, wherein amino acids of fragments of influenza virus B and C type corresponding to the influenza virus A type are shown in FIGS. 1A, 1B, 1C and FIGS. 10A, 10B respectively.

In a preferred embodiment, the present invention provides a three-dimensional crystal structure of a complex of a C-terminal part of influenza virus polymerase subunit PA-PAc and an N-terminal part of influenza virus polymerase subunit PB1-PB1$_N$, wherein amino acid residues of positions 370405 of the C-terminal part of influenza virus A polymerase subunit PA-PAc constitutes a large loop, wherein amino acids of fragments of influenza virus B and C type corresponding to the influenza virus A type are shown in FIGS. 1A, 1B, 1C and FIGS. 10A, 10B respectively.

In a preferred embodiment, the present invention provides a three-dimensional crystal structure of a complex of a C-terminal part of influenza virus polymerase subunit PA-PAc and an N-terminal part of influenza virus polymerase subunit PB1-PB1$_N$, wherein α helix 12 and α helix 13 of C-terminal of influenza virus polymerase subunit PA-PAc interact with other proteins, preferably wherein at least one amino acid selected from the group consisting of Ile690, Glu691, Glu692, Cys693 and Asn696 of the α helix 12 and α helix 13 interacts with other proteins, and amino acids of fragments of influenza virus B and C type corresponding to the influenza virus A type are shown in FIGS. 1A, 1B, 1C and FIGS. 10A, 10B respectively.

In a preferred embodiment, the present invention provides a three-dimensional crystal structure of complex of a C-terminal part of influenza virus polymerase subunit PA-PAc and an N-terminal part of influenza virus polymerase subunit PB1-PB1$_N$, wherein at least one amino acid of the C-terminal part of influenza virus polymerase subunit PA-PAc that is selected from the group consisting of Lys506, Gly507, Arg508, Ser509, His510, Leu511, Arg512, Asn513 and Asp514 interacts with other proteins, wherein His510 constitutes a portion of the polymerase complex RNAse, and amino acids of fragments of influenza virus B and C type corresponding to the influenza virus A type are shown in FIGS. 1A, 1B, 1C and FIGS. 10A, 10B respectively.

In another embodiment, the present invention provides a polypeptide, protein, inorganic compound or organic compound binding to at least one member selected from the group consisting of α helix 8, α helix 10, α helix 11 and α helix 13 of C-terminal of influenza virus polymerase subunit PA-PAc, wherein the influenza virus is selected from influenza virus A, B and C type, preferably influenza virus A type: A/goose/Guangdong/1/96, A/Brevig Mission/1/1918; influenza virus B type: B/Ann Arbor/1/1966 or influenza virus C type: C/JJ/1950; wherein the polypeptide, protein, inorganic compound or organic compound, antibody or immunoconjugate preferably binds to a member selected from the group consisting of Leu666 in α helix 11, Phe710 in α helix 13, Val636 and Leu640 in α helix 10, Trp706 in α helix 13, Gln670 in α helix 11 of the C-terminal part of influenza virus polymerase subunit PA-PAc, wherein amino acids of fragments of influenza virus B and C type corresponding to the influenza virus A type are shown in FIGS. 1A, 1B, 1C and FIGS. 10A, 10B respectively.

In another embodiment, the present invention provides a polypeptide, protein, inorganic compound or organic compound, antibody or immunoconjugate binding to at least one member selected from the group consisting of Ile621, Gly622, Glu623, Thr618 and Pro620 located at the peptide loop between α helix 9 and α helix 10 of the C-terminal part of influenza virus polymerase subunit PA-PAc, wherein amino acids of fragments of influenza virus B and C type corresponding to the influenza virus A type are shown in FIGS. 1A, 1B, 1C and FIGS. 10A, 10B respectively.

In another embodiment, the present invention provides a polypeptide, protein, inorganic compound or organic compound, antibody or immunoconjugate binding to at least one amino acid selected from the group consisting of Asn647, Gln408, Cys584, Gln587, Gln591, Lys643, Asn647, Ser659, Lys663, Trp699 and Asn703 of the C-terminal part of influenza virus A polymerase subunit PA-PAc, wherein amino acids of fragments of influenza virus B and C type corresponding to influenza virus A type are shown in FIGS. 1A, 1B, 1C and FIGS. 10A, 10B respectively.

In another embodiment, the present invention provides a polypeptide, protein, inorganic compound or organic compound, antibody or immunoconjugate binding to at least one amino acid selected from the group consisting of Trp406, Glu410, Lys461, Glu524, Phe525, Ser526, Lys536, Lys539, Tyr540, Leu563, Tyr564, Arg566 and Lys574 of the C-terminal part of influenza virus A polymerase subunit PA-PAc, wherein amino acids of fragments of influenza virus B and C type corresponding to influenza virus A type are shown in FIGS. 1A, 1B, 1C and FIGS. 10A, 10B respectively.

In another embodiment, the present invention provides a polypeptide, protein, inorganic compound or organic compound, antibody or immunoconjugate binding to amino acids position 370-405 of the C-terminal part of influenza virus A polymerase subunit PA-PAc, wherein amino acids of fragments of influenza virus B and C type corresponding to influenza virus A type are shown in FIGS. 1A, 1B, 1C and FIGS. 10A, 10B respectively.

In another embodiment, the present invention provides a polypeptide, protein, inorganic compound or organic compound, antibody or immunoconjugate binding to helix 12 and α helix 13 of the C-terminal part of influenza virus A polymerase subunit PA-Pac, preferably to at least one amino acid selected from the group consisting of Ile690, Glu691, Glu692, Cys693 and Asn696 in α helix 12 and α helix 13, wherein amino acids of fragments of influenza virus B and C type corresponding to influenza virus A type are shown in FIGS. 1A, 1B, 1C and FIGS. 10A, 10B respectively.

In another embodiment, the present invention provides a polypeptide, protein, inorganic compound or organic compound, antibody or immunoconjugate binding to at least one amino acid selected from the group consisting of Lys506, Gly507, Arg508, Ser509, His510, Leu511, Arg512, Asn513 and Asp514 located at loop region between β sheet 4 and β sheet 5 in the C-terminal part of influenza virus A polymerase subunit PA-PAc, wherein amino acids of fragments of influenza virus B and C type corresponding to influenza virus A type are shown in FIGS. 1A, 1B, 1C and FIGS. 10A, 10B respectively.

In another embodiment, the present invention provides a polypeptide, protein, inorganic compound or organic compound, antibody or immunoconjugate which competes with influenza virus polymerase subunit PB1 (SEQ ID NO:2) for binding PAc.

In a preferred embodiment, the present invention provides the polypeptide, protein, inorganic compound or organic compound, antibody or immunoconjugate which competes with influenza virus polymerase subunit PB1 (SEQ ID NO:2) for binding PAc predominantly by an interaction with PAc through the hydrophobic core constituted by the α helix 8, α helix 11, α helix 13 and α helix 10, preferably interaction with PAc through Met595 in α helix 8, Leu666 in α helix 11, Trp706 and Phe710 in α helix 13, Val636 and Val640 in α helix 10, wherein amino acids of corresponding fragments of influenza virus B and C type to influenza virus A type are shown in FIGS. 1A, 1B, 1C and FIGS. 10A, 10B respectively.

In a preferred embodiment, the present invention provides a polypeptide, protein, inorganic compound or organic compound, antibody or immunoconjugate which competes with influenza virus polymerase subunit PB1 (SEQ ID NO:2) for binding PAc, wherein the amino acid sequence of the polypeptide or protein comprises at least three amino acids which are identical to amino acids of corresponding position of a short PTLLFL motif of the short helix domain constituted by the 5th-10th residues Pro5, Thr6, Leu7, Leu8, Phe9 and Leu10 of the N-terminal part of wild influenza virus polymerase subunit PB1-PB1$_N$, when the polypeptide or protein is aligned with the PTLLFL motif.

In another embodiment, the present invention provides a composition comprising above-mentioned polypeptide, protein, inorganic compound or organic compound, antibody or immunoconjugate, and optionally comprising a carrier and an excipient.

In another embodiment, the present invention provides use of the composition in the manufacture of a medicament used in the treatment of diseases caused by influenza virus.

In another embodiment, the present invention provides a method of expressing and purifying the complex of an C-terminal part of influenza virus polymerase subunit PA-PAc and an N-terminal part of influenza virus polymerase subunit PB1-PB1$_N$, comprising:

(a) constructing a vector with a gene sequence encoding amino acid from about positions 201-301 to about 650 terminus of a C-terminal part of influenza virus polymerase subunit PA-PAc, where the vector can further comprise a protein tag, wherein prokaryotic cells or eukaryotic cells are transformed with said vector in order to express a tagged PAc fusion protein;

(b) using a method analogous to the method of expressing PAc to express the PB1$_N$ with or without a protein tag;

(c) Proportionally mixing the cells expressing influenza virus polymerase subunit PAc obtained from step (a) and the cells expressing amino acids within the 48 amino acids of the N-terminal of influenza virus polymerase subunit PB1 obtained from step (b), wherein the resulting protein is isolated by the specific recognition of the specific tag, the protein tag is removed from the protein by enzymolysis, the complex of PAc and PB1$_N$ is isolate, and the concentration of the complex is determined;

wherein the atoms of the three-dimensional crystal structure of the complex of the C-terminal part of influenza virus polymerase subunit PA-PAc and the N-terminal part of influenza virus polymerase subunit PB1-PB1$_N$ have at least 40% of the atomic coordinates listed in table 1, or atomic coordinates of main chain backbone carbons of at least 40% amino acids in the three-dimensional crystal structure of the complex of the C-terminal part of influenza virus polymerase subunit PA-PAc and the N-terminal part of influenza virus polymerase subunit PB1-PB1$_N$ have an average root mean square deviation smaller than or equal to 1.7 Angstrom with respect to the atomic coordinates listed in table 1.

In a preferred embodiment, wherein the protein tag is selected from GST, Flag-tag, Myc-tag, MBP-tag, specific antibodies; the vector comprises a selection marker gene; the proportional mixing in step (c) above means that the molar ratio of protein-tagged PAc and protein-tagged PB1$_N$ is 0.1:1-1:0.1, preferably the molar ratio of protein-tagged PAc and protein-tagged PB1$_N$ is 0.5:1-1:0.5, more preferably the molar ratio of protein-tagged PAc and protein-tagged PB1$_N$ is nearly 1:1; wherein preferably the protein tag is GST, wherein the tag is specifically recognized using an affinity column, wherein the tag is removed by a proteinase, wherein the complex of PAc and PB1$_N$ is separated by gel filtration or ion-exchange chromatography, and wherein the the protein purity is determined by gel electrophoresis.

In a more preferable embodiment, the procaryotic cell is E coli.

In another embodiment, the present invention provides a method of co-crystallizing the complex of an C-terminal part of influenza virus polymerase subunit PA-PAc and an N-terminal part of influenza virus polymerase subunit PB1-PB1$_N$, comprising:

adjusting the protein concentration of the purified complex of PAc and PB1$_N$ to 5-30 mg/ml;

screening crystal growth conditions by gas sitting drop and hanging drop;

obtaining a crystal of the complex of the C-terminal part of influenza virus polymerase subunit PA-PAc and the N-terminal part of influenza virus polymerase subunit PB1-PB1$_N$.

In another embodiment, the present invention provides a method of expressing wild type or mutant protein of an N-terminal part of PA-PA$_N$, wherein PA$_N$ comprises amino acids from about position 1-50 to about position 200-300, the method comprising: constructing an expression vector with a gene sequence encoding amino acid from about position 1-50 to about 200-300 of the N-terminal part of influenza virus polymerase subunit PA-PA$_N$, the vector comprising a gene for protein tag fusion or no protein tag fusion, wherein eukaryotic cells or prokaryotic cells are transformed with said vector in order to express PA$_N$ with or without the protein tag, wherein the amino acid sequence of the N-terminal part of PA-PA$_N$ exhibits at least 40% sequence identity with the amino acids sequence listed in FIG. 1C.

In a preferred embodiment, the procaryotic cell is E coli.

In another embodiment, the present invention provides a method of screening candidate compounds which compete with PB1$_N$ for binding PAc, the method comprising:

(a) attaching PAc to the surface of a fixed support;

(b) contact the excess tagged PB1$_N$ with the attached PAc;

(c) eluting thoroughly with an eluent in order to remove un-bound $PB1_N$;

(d) contacting a solution with the candidate compound to be detected with the attached PAc with bound $PB1_N$;

(e) eluting thoroughly with an eluent in order to obtain a solution to be detected;

(f) measuring the concentration of free tagged $PB1_N$ in the solution to be detected;

(g) calculating the binding capability of the candidate compound to be detected with PAc according to the concentration of free tagged $PB1_N$ in the solution to be detected.

In a preferred embodiment, PAc is attached to the surface of the fixed support in step (a) by covalently cross-linking or binding PAc with an affinity tag, and attaching PAc to the fixed support by affinity binding.

Preferably, the affinity tag is selected from GST, Flag-tag, Myc-tag, MBP-tag and specific antibody and there is corresponding binding group of the affinity tag on the surface of the fixed support.

Preferably, the $PB1_N$ polypeptide is tagged with an isotope or another chemical molecule; preferably, the other chemical molecular tag is green fluorescent protein or various fusion polypeptides.

Preferably, the fixed surface can be affinity chromatography columns.

In one embodiment, the present invention provides use of the three-dimensional crystal structure of complex of a C-terminal part of influenza virus polymerase subunit PA-PAc and an N-terminal part of influenza virus polymerase subunit PB1-$PB1_N$ in designing and screening a polypeptide, protein, inorganic compound or organic compound, antibody or immunoconjugate used in the treatment of diseases caused by the influenza virus infection, comprising:

designing polypeptide, protein, inorganic compound or organic compound, antibody or immunoconjugate binding to a specific portion of the polymerase by computer simulation technology according to the coordinates of the three-dimensional protein structure;

screening for a polypeptide, protein, inorganic compound or organic compound, antibody or immunoconjugate potentially binding to a specific portion of the polymerase by computer simulation technology according to the coordinates of the three-dimensional protein structure;

analyzing the binding characteristics of the designed or screened polypeptide, protein, inorganic compound or organic compound, antibody or immunoconjugate according to the coordinates of three-dimensional protein structure in binding to any type of influenza virus polymerase protein which has at least 50% sequence identity with the PAc and the $PB1_N$ sequence;

crystallizing the designed or screened polypeptide, protein, inorganic compound or organic compound, antibody or immunoconjugate according to the coordinates of three-dimensional protein structure in binding to any type of influenza virus polymerase protein which has at least 50% sequence identity with the PAc and the $PB1_N$ sequence, and analyzing the binding characteristics of the polypeptide or compound molecule to the protein by crystal diffraction;

wherein the polypeptide, protein, inorganic compound or organic compound, antibody or immunoconjugate is a candidate compound in that it binds to any type of influenza virus polymerase protein which has at least 50% sequence identity with the PAc and the $PB1_N$ sequence.

In one embodiment, the present invention provides a structure of the three subunits i.e. PA, PB1, PB2 of any subtype of influenza virus polymerase or the complex of PA, PB1 and PB2, wherein a protein contained in it or a fragment thereof has 40% identical sequence with the PAc protein.

In one embodiment, the present invention provides a three-dimensional stereochemical structure of the three subunits i.e. PA, PB1, PB2 of any subtype of influenza virus polymerase or that of the complex of PA, PB1 and PB2, wherein the coordinates of the three-dimensional structure in main chain of a protein contained in it or a fragment thereof has an average root mean square deviation smaller than or equal to 1.7 Angstrom with respect to the three-dimensional atomic coordinates of main chain backbone carbons having at least 40% amino acid residues of the PAc protein sequence.

In one embodiment, the present invention provides structure of subunit PA, PB1, PB2 or that of the complex of subunit PA, PB1 and PB2 from any subtype of influenza virus, wherein a protein fragment contained in it has 20% sequence homology with the fragment of amino acids 1-11 of the $PB1_N$ polypeptide, preferably 40% sequence homology.

In one embodiment, the present invention provides a polypeptide or a small molecule, characterized in that it interacts with any amino acid of the influenza virus subunit PA.

In one embodiment, the present invention provides use of the crystal three-dimensional structure in drug screening and drug design.

In one embodiment, the present invention provides a method of screening a polypeptide, protein, inorganic compound or organic compound, antibody or immunoconjugate which binds to the protein based on a three-dimensional crystal structure of PAc and $PB1_N$ protein, comprising: obtaining a PAc-containing crystal by protein crystallization, or obtaining the coordinates of a three-dimensional crystal structure of the protein complex containing PAc and $PB1_N$; wherein the three-dimensional structure comprises any structure that has an average root mean square deviation smaller than or equal to 1.7 Angstrom with respect to the three-dimensional coordinates of a main chain backbone carbons having at least 40% amino acid residues of the atomic coordinates.

In one embodiment, the present invention provides a method of expressing and purifying the influenza virus subunit PA through expressing PA fragments in bacteria and eukaryotic cell expression systems.

In one embodiment, the present invention provides a polypeptide, protein, inorganic compound or organic compound, antibody or immunoconjugate that interacts with amino-acid residues on a protein, wherein the protein has at least 40% identical amino acids with any fragment of α helix 8, 10, 11 and 13 in complex of C-terminal of influenza virus polymerase subunit PA-PAc and N-terminal of influenza virus polymerase subunit PB1-$PB1_N$.

It should be noted that the fragments in influenza virus B and C type corresponding to α helix and β sheet of influenza virus A are shown in FIGS. 1A, 1B, 1C and FIG. 10A, FIG. 10B respectively, which will not be listed in detail. The alignment methods of protein or polypeptide sequence that can be used is for example: CLUSTALW (http://www.ebi.ac.uk/Tools/clustalw2/index.html).

Expression and Purification Methods of Influenza Virus PA (SEQ ID NO:1) and PB1 (SEQ ID NO:2) Protein The protein sequences encoded by virus gene derived from Avian influenza virus A/goose/Guangdong/1/96 are respectively as follows:

(1) Protein Sequence of PA:

MEDFVRQCFNPMIVELAEKAMKEYGEDPKIETNKFAAICTHLEVCFMYS

DNIFIDERGESTIIESGDPNALLKHRFEIIEGRDRTMAWTVVNSICNTT

GVEKPKFLPDLYDYKENRFIEIGVTRREVHTYYLEKANKIKSEKTHIHI

FSFTGEEMATKADYTLDEESRARIKTRLFTIRQEMASRGLWDSFRQSER

GEETIEERFEITGTMCRLADQSLPPNFSSLEKFRAYVDGEEPNGCIEGK

LSQMSKEVNARIEPFLKTTPRPLRLPDGPPCSQRSKFLLMDALKLSIED

-continued

PSHEGEGIPLYDAIKCMKTFFGWKEPNIVKPHEKGINPNYLLAWKQVLA
ELQDIENEEKIPKTKNMRKTSQLKWALGENMAPEKVDFEDCKDVSDLRQ
YDSDEPKPRSLASWIQSEFNKACELTDSSWIELDEIGEDVAPIEHIASM
RRNYFTAEVSHCRATEYIMKGVYINTALLNASCAAMDDFQLIPMISKCR
TKEGRRKTNLYGFIIKGRSHLRNDTDVVNFVSNIEFSLTDPRLEPHKWE
KYCVLEIGDMLLRTAIGQVSRPMFLYVRTNGTSKIKMKWGMEMRRCLLQ
SLQQIESMIEAESSVKEKDMTKEFFENKSETWPIGESPKGMEEGSIGKV
CRTLLAKSVFNSLYASPQLEGFSAESRKLLLIVQALRDNLEPGTFDLGG
LYEAIEECLINDPWVLLNASWFNSFLTHALK; i.e., (SEQ ID NO: 1)
Met Glu Asp Phe Val Arg Gln Cys Phe Asn Pro Met
Ile Val Glu Leu Ala Glu Lys Ala Met Lys Glu Tyr
Gly Glu Asp Pro Lys Ile Glu Thr Asn Lys Phe Ala
Ala Ile Cys Thr His Leu Glu Val Cys Phe Met Tyr
Ser Asp Phe His Phe Ile Asp Glu Arg Gly Glu Ser
Thr Ile Ile Glu Ser Gly Asp Pro Asn Ala Leu Leu
Lys His Arg Phe Glu Ile Ile Glu Gly Arg Asp Arg
Thr Met Ala Trp Thr Val Val Asn Ser Ile Cys Asn
Thr Thr Gly Val Glu Lys Pro Lys Phe Leu Pro Asp
Leu Tyr Asp Tyr Lys Glu Asn Arg Phe Ile Glu Ile
Gly Val Thr Arg Arg Glu Val His Thr Tyr Tyr Leu
Glu Lys Ala Asn Lys Ile Lys Ser Glu Lys Thr His
Ile His Ile Phe Ser Phe Thr Gly Glu Glu Met Ala
Thr Lys Ala Asp Tyr Thr Leu Asp Glu Glu Ser Arg
Ala Arg Ile Lys Thr Arg Leu Phe Thr Ile Arg Gln
Glu Met Ala Ser Arg Gly Leu Trp Asp Ser Phe Arg
Gln Ser Glu Arg Gly Glu Glu Thr Ile Glu Glu Arg
Phe Glu Ile Thr Gly Thr Met Cys Arg Leu Ala Asp
Gln Ser Leu Pro Pro Asn Phe Ser Ser Leu Glu Lys
Phe Arg Ala Tyr Val Asp Gly Phe Glu Pro Asn Gly
Cys Ile Glu Gly Lys Leu Ser Gln Met Ser Lys Glu
Val Asn Ala Arg Ile Glu Pro Phe Leu Lys Thr Thr
Pro Arg Pro Leu Arg Leu Pro Asp Gly Pro Pro Cys
Ser Gln Arg Ser Lys Phe Leu Leu Met Asp Ala Leu
Lys Leu Ser Ile Glu Asp Pro Ser His Glu Gly Glu
Gly Ile Pro Leu Tyr Asp Ala Ile Lys Cys Met Lys
Thr Phe Phe Gly Trp Lys Glu Pro Asn Ile Val Lys
Pro His Glu Lys Gly Ile Asn Pro Asn Tyr Leu Leu
Ala Trp Lys Gln Val Leu Ala Glu Leu Gln Asp Ile
Glu Asn Glu Glu Lys Ile Pro Lys Thr Lys Asn Met
Arg Lys Thr Ser Gln Leu Lys Trp Ala Leu Gly Glu

Asn Met Ala Pro Glu Lys Val Asp Phe Glu Asp Cys
Lys Asp Val Ser Asp Leu Arg Gln Tyr Asp Ser Asp
Glu Pro Lys Pro Arg Ser Leu Ala Ser Trp Ile Gln
Ser Glu Phe Asn Lys Ala Cys Glu Leu Thr Asp Ser
Ser Trp Ile Glu Leu Asp Glu Ile Gly Glu Asp Val
Ala Pro Ile Glu His Ile Ala Ser Met Arg Arg Asn
Tyr Phe Thr Ala Glu Val Ser His Cys Arg Ala Thr
Glu Tyr Ile Met Lys Gly Val Tyr Ile Asn Thr Ala
Leu Leu Asn Ala Ser Cys Ala Ala Met Asp Asp Phe
Gln Leu Ile Pro Met Ile Ser Lys Cys Arg Thr Lys
Glu Gly Arg Arg Lys Thr Asn Leu Tyr Gly Phe Ile
Ile Lys Gly Arg Ser His Leu Arg Asn Asp Thr Asp
Val Val Asn Phe Val Ser Met Glu Phe Ser Leu Thr
Asp Pro Arg Leu Glu Pro His Lys Trp Glu Lys Tyr
Cys Val Leu Glu Ile Gly Asp Met Leu Leu Arg Thr
Ala Ile Gly Gln Val Ser Arg Pro Met Phe Leu Tyr
Val Arg Thr Asn Gly Thr Ser Lys Ile Lys Met Lys
Trp Gly Met Glu Met Arg Arg Cys Leu Leu Gln Ser
Leu Gln Gln Ile Glu Ser Met Ile Glu Ala Glu Ser
Ser Val Lys Glu Lys Asp Met Thr Lys Glu Phe Phe
Glu Asn Lys Ser Glu Thr Trp Pro Ile Gly Glu Ser
Pro Lys Gly Met Glu Glu Gly Ser Ile Gly Lys Val
Cys Arg Thr Leu Leu Ala Lys Ser Val Phe Asn Ser
Leu Tyr Ala Ser Pro Gln Leu Glu Gly Phe Ser Ala
Glu Ser Arg Lys Leu Leu Leu Ile Val Gln Ala Leu
Arg Asp Asn Leu Glu Pro Gly Thr Phe Asp Leu Gly
Gly Leu Tyr Glu Ala Ile Glu Glu Cys Leu Ile Asn
Asp Pro Trp Val Leu Leu Asn Ala Ser Trp Phe Asn
Ser Phe Leu Thr His Ala Leu Lys.

(2) Protein Sequence of PB1:

MDVNPTLLFLKVPAQNAISTTFPYTGDPPYSHGTGTGYTMDTVNRTHQY
SEKGKWTTNTETGAPQLNPIDGPLPEDNEPSGYAQTDCVLEAMAFLEKS
HPGIFENSCLETMEIVQQTRVDKLTQGRQTYDWTLNRNQPAATALANTI
EVFRSNGLTANESGRLIDFLKDVMESMDKGEMEIITHFQRKRRVRDNMT
KKMVTQRTIGKKKQRLNKRSYLIRALTLNTMTKDAERGKLKRRAIATPG
MQIRGFVYFVETLARSICEKLEQSGLPVGGNEKKAKLANVVRKMMTNSQ
DTELSFTITGDNTKWNENQNPRMFLAMITYITRNQPEWFRNVLSIAPIM
FSNKMARLGKGYMFESKSMKLRTQIPAEMLASIDLKYFNESTRKKIEKI
RPLLIDGTASLSPGNIMMGMFNMLSTVLGVSILNLGQKRYTKTTYWWDG

-continued
LQSSDDFALIVNAPNHEGIQAGVDRFYRTCKLVGINMSKKKSYINRTGT

EEFTSFFYRYGFVANFSMELPSFGVSGINESADMSIGVTVIKNNMINND

LGPATAQMALQLFIKDYRYTYRCHRGDTQIQTRRSEELKKLWEQTRSKA

GLLVSDGGPNLYNIRNLHIPEVCLKWELMDEDYQGRLCNPLNPFVSHKE

IESVNNAVVMPAHGPAKSMEYDAVATTHSWIPKRNRSILNTSQRGILED

EQMYQKCCNLFEKFFPSSSYRRPVGISSMVEAMVSRARIDARIDFESGR

IKKEEFAEIMKICSTIEELRRQK; i.e., (SEQ ID NO: 2)
Met Asp Val Asn Pro Thr Leu Leu Phe Leu Lys Val

Pro Ala Gln Asn Ala Ile Ser Thr Thr Phe Pro Tyr

Thr Gly Asp Pro Pro Tyr Ser His Gly Thr Gly Thr

Gly Tyr Thr Met Asp Thr Val Asn Arg Thr His Gln

Tyr Ser Glu Lys Gly Lys Trp Thr Thr Asn Thr Glu

Thr Gly Ala Pro Gln Leu Asn Pro Ile Asp Gly Pro

Leu Pro Glu Asp Asn Glu Pro Ser Gly Tyr Ala Gln

Thr Asp Cys Val Leu Glu Ala Met Ala Phe Leu Glu

Lys Ser His Pro Gly Ile Phe Glu Asn Ser Cys Leu

Glu Thr Met Glu Ile Val Gln Gln Thr Arg Val Asp

Lys Leu Thr Gln Gly Arg Gln Thr Tyr Asp Trp Thr

Leu Asn Arg Asn Gln Pro Ala Ala Thr Ala Leu Ala

Asn Thr Ile Glu Val Phe Arg Ser Asn Gly Leu Thr

Ala Asn Glu Ser Gly Arg Leu Ile Asp Phe Leu Lys

Asp Val Met Glu Ser Met Asp Lys Gly Glu Met Glu

Ile Ile Thr His Phe Gln Arg Lys Arg Arg Val Arg

Asp Asn Met Thr Lys Lys Met Val Thr Gln Arg Thr

Ile Gly Lys Lys Lys Gln Arg Leu Asn Lys Arg Ser

Tyr Leu Ile Arg Ala Leu Thr Leu Asn Thr Met Thr

Lys Asp Ala Glu Arg Gly Lys Leu Lys Arg Arg Ala

Ile Ala Thr Pro Gly Met Gln Ile Arg Gly Phe Val

Tyr Phe Val Glu Thr Leu Ala Arg Ser Ile Cys Glu

Lys Leu Glu Gln Ser Gly Leu Pro Val Gly Gly Asn

Glu Lys Lys Ala Lys Leu Ala Asn Val Val Arg Lys

Met Met Thr Asn Ser Gln Asp Thr Glu Leu Ser Phe

Thr Ile Thr Gly Asp Asn Thr Lys Trp Asn Glu Asn

Gln Asn Pro Arg Met Phe Leu Ala Met Ile Thr Tyr

Ile Thr Arg Asn Gln Pro Glu Trp Phe Arg Asn Val

Leu Ser Ile Ala Pro Ile Met Phe Ser Asn Lys Met

Ala Arg Leu Gly Lys Gly Tyr Met Phe Glu Ser Lys

Ser Met Lys Leu Arg Thr Gln Ile Pro Ala Glu Met

Leu Ala Ser Ile Asp Leu Lys Tyr Phe Asn Glu Ser

Thr Arg Lys Lys Ile Glu Lys Ile Arg Pro Leu Leu

Ile Asp Gly Thr Ala Ser Leu Ser Pro Gly Met Met

Met Gly Met Phe Asn Met Leu Ser Thr Val Leu Gly

Val Ser Ile Leu Asn Leu Gly Gln Lys Arg Tyr Thr

Lys Thr Thr Tyr Trp Trp Asp Gly Leu Gln Ser Ser

Asp Asp Phe Ala Leu Ile Val Asn Ala Pro Asn His

Glu Gly Ile Gln Ala Gly Val Asp Arg Phe Tyr Arg

Thr Cys Lys Leu Val Gly Ile Asn Met Ser Lys Lys

Lys Ser Tyr Ile Asn Arg Thr Gly Thr Phe Glu Phe

Thr Ser Phe Phe Tyr Arg Tyr Gly Phe Val Ala Asn

Phe Ser Met Glu Leu Pro Ser Phe Gly Val Ser Gly

Ile Asn Glu Ser Ala Asp Met Ser Ile Gly Val Thr

Val Ile Lys Asn Asn Met Ile Asn Asn Asp Leu Gly

Pro Ala Thr Ala Gln Met Ala Leu Gln Leu Phe Ile

Lys Asp Tyr Arg Tyr Thr Tyr Arg Cys His Arg Gly

Asp Thr Gln Ile Gln Thr Arg Arg Ser Phe Glu Leu

Lys Lys Leu Trp Glu Gln Thr Arg Ser Lys Ala Gly

Leu Leu Val Ser Asp Gly Gly Pro Asn Leu Tyr Asn

Ile Arg Asn Leu His Ile Pro Glu Val Cys Leu Lys

Trp Glu Leu Met Asp Glu Asp Tyr Gln Gly Arg Leu

Cys Asn Pro Leu Asn Pro Phe Val Ser His Lys Glu

Ile Glu Ser Val Asn Asn Ala Val Val Met Pro Ala

His Gly Pro Ala Lys Ser Met Glu Tyr Asp Ala Val

Ala Thr Thr His Ser Trp Ile Pro Lys Arg Asn Arg

Ser Ile Leu Asn Thr Ser Gln Arg Gly Ile Leu Glu

Asp Glu Gln Met Tyr Gln Lys Cys Cys Asn Leu Phe

Glu Lys Phe Phe Pro Ser Ser Ser Tyr Arg Arg Pro

Val Gly Ile Ser Ser Met Val Glu Ala Met Val Ser

Arg Ala Arg Ile Asp Ala Arg Ile Asp Phe Glu Ser

Gly Arg Ile Lys Lys Glu Glu Phe Ala Glu Ile Met

Lys Ile Cys Ser Thr Ile Glu Glu Leu Arg Arg Gln

Lys

The gene of influenza virus subunit PA (SEQ ID NO:1) was divided into a C-terminal part and an N-terminal part, and then the C-terminal part and the N-terminal part were cloned by molecular cloning techniques, wherein the N-terminal part contains the first 256 amino acids and the C-terminal part contains amino acids 257-716. The two parts were cloned into pGEX-6p vector (from Amersham Pharmacia Inc.) respectively so as to express fusion proteins of N-terminal fused with GST (GST-PAN and GST-PAc). The cloned plasmids were transformed into *E. coli* BL21 respectively, and *E.coli* were induced by using 0.1 to 1 mM IPTG (isopropyl-β-thiogalactoside) in BL21 to express these two proteins respectively, thus obtaining respectively expressing bacteria of these two protein, for details see Example 1.

The gene encoding N-terminal 48 amino acids of PB1 (including the peptide of the first 25 amino acids) was also cloned into pGEX-6p vector, in order to express a fusion protein of fused GST-PB1 peptide.

Likewise, the short peptide of GST fused the former 25 amino acids or former 48 amino acids of PB1$_N$ was expressed respectively. The vectors were transformed into *E. coli* BL21 in the same way. *E.coli* were induced by using 0.1 to 1 mM IPTG in BL21 to express proteins, thus obtaining bacteria expressing the protein.

The bacteria that express GST-PA-N were suspended in buffer, lysed and centrifuged to obtain supernatant. Then affinity chromatographic column was used to purify GST-PA-N fusion protein from the supernatant.

The GST-PAc expressing bacteria and the GST-PB1 expressing bacteria were suspended with a buffer (which contains about 20 mM Tris-HCl (pH 8.0) and 250 mM NaCl) respectively and mixed with a molar ratio between the protein content of GST-PAc and GST-PB1$_N$ is 0.1:1-1:0.1, preferably the molar ratio between the protein content of GST-PAc and GST-PB1$_N$ is 0.5:1-1:0.5, more preferably the molar ratio between the protein content of GST-PAc and GST-PB1$_N$ is near 1:1.

Subsequently, Glutathione-Sepharose affinity column (from Amersham Pharmacia Inc.) was used to purify the GST fusion protein. After enzymolysis with PreScission protease (from Amersham Pharmacia Inc.), the complex of PAc/PB1 short peptide was separated and purified through such methods as gel filtration Superdex-200 and ion exchange chromatography (Q sepharose), wherein complex can be used for further crystallization experiment after determining the protein concentration by SDS-PAGE gel electrophoresis.

Crystallization and Optimization of Protein

The complex that has been expressed and purified through above methods was condensed to a concentration of 5-30 mg/ml, and crystal growth condition is screened with crystallization reagents (from Hampton Research) by gas hanging drop so as to obtain original crystals under conditions of multiple crystallization reagents.

Through further optimization, crystals with good appearance were obtained in solution containing about 1M sodium acetate with different buffer conditions under pH 4-9, wherein larger triangle-cone crystal was obtained in solution containing about 1-1.3M sodium acetate (Sigma) with different buffers under pH 4-9, and the resolution of said crystal is about 4 Angstrom.

When collecting X-ray diffraction data, the crystal required by diffraction was transferred from hanging drops to about 10 µl corresponding crystallization buffer containing 1.4M sodium acetate and 10% glycerol (Sigma). After the fluid drops are left open for air dehydration for more than one hour, parent crystal and selenium-containing crystal with a resolution of about 3 Angstrom as well as corresponding X-ray diffraction data were obtained.

Collection of Crystal Data and Structure Analysis

A set data of parent crystal with a resolution of 2.9 Angstrom from the complex crystal of PA-PB1 N-terminal (this PB1 N-terminal contains 25 amino acids) was first collected by using FR-E X-ray diffractometer (Rigaku) under a wave length 1.5418 Angstrom. Then under wave length of 0.9783 and 0.9785 Angstrom, two sets of data from derivative crystal of selenium atom were collected, i.e. peak and edge, using synchrotron radiometer located at APS, Chicago, USA (station number: SBC 191D; detection screen: ADSC Q315), the resolution of said crystal is about 3.3 Angstrom. The three sets of data were treated by HKL2000 (Otwinowski 1997) and found to have spacegroup of P4(1)2(1)2. Phase was calculated by multi-wavelength anomalous scattering (Hendrickson 1991), and sas file resulted from treatment was searched for selenium atoms by SHELXD (Sheldrick 1998). The protein itself has 14 methionines, and the inventors found 14 selenium atoms in all. Coordinates of selenium atoms and two sets of data (i.e. Peak and Edge) were input into Program autoSHARP (Vonrhein, Blanc et al. 2007) to calculate phase and to modify the electron density map, and several secondary structures (including α helixes and β sheets) can be clearly found from the calculated electron density map. Then phase can be expanded by Program CAD, and the phase was expanded to 2.9 Angstrom by collected parent data so as to construct a structure model, wherein the Programs used to construt model are ARP/wARP (Perrakis, Morris et al. 1999) and Phenix (Adams, Grosse-Kunstleve et al. 2002). Automatic model construction performed by these two programs can amount to 60% of the whole structure, and the rest is manually constructed through Program COOT (Emsley and Cowtan 2004).

Finally, the resulting model was modified by Program CNS (Brunger, Adams et al. 1998) and REFMAC5 (Murshudov, Vagin et al. 1997) to achieve the protein structure analysis, and the final factor R and factor R-free for modify structure are 0.22 and 0.26 respectively.

Atomic coordinates in crystal structure of protein complex of PAc/PB1$_N$ short peptide, see Table 1.

EXAMPLE

Method for Expressing Influenza Virus PA and PB1 Polypeptides

In one embodiment of the present invention, PA (SEQ ID NO:1) was divided into two fragments so as to express former 256 amino acid residues fragments and 257-716 amino acid residues fragments of the PA, respectively, and two gene fragments encoding these two protein polypeptides were cloned into an *Escherichia coli* expression vector, respectively so as to expressing proteins in a bacteria. The PA N-terminal polypeptides were purified from a PA N-terminal (1-256 amino acids) expressing bacteria and used for protein crystallization. C-terminal of PA expressing bacteria was centrifugally collected for later use so as to be co-purified with the N-terminal of PB1 polypeptides.

Polypeptide containing former 25 or no more than 48 amino acids of the N-terminal of PB1 (not containing first-position methionine) was expressed in the form of GST fusion protein in a bacteria. The influenza virus polymerase protein subunit PA was expressed by fragments in a bacteria or other eukaryotic cells such that at least 50% fragments were part of amino acid fragments of positions 257-716 of the PA protein.

Expression and Purification of N-terminal of Influenza Virus PA in *Escherichia Coli*

The N-terminal of the influenza virus PA (amino acids 1-256) was cloned into a pGEX-6p vector (from Amersham Pharmacia Inc.) via a molecular cloning technique, the cloning sites thereof being BamHI and XhoI. Expression plasmids with a PA N-terminal gene, obtained by cloning, were transformed into *Escherichia coli* BL21 for protein expression, such that the bacteria could express the N-terminal (amino terminal) of the PA protein which was connected with the GST fusion protein and has protease cleavage sites cleaved by ProScission protease to further separate a GST protein tag from the target protein-PA polypeptide. IPTG with a final concentration of about 0.1-1 mM was used in the cultured *Escherichia coli* BL21 cells to induce *Escherichia coli* in order to obtain the expressing bacteria of said protein. The used vector contained an ampicillin-resistance gene. After the cloning-constructed expression plasmids of the fusion protein were transformed into *Escherichia coli* such as BL21 (Novagen), bacterium were cultured overnight using bacteria culture media such as LB and so on at 37° C., and after about 12 hours transferred to a mass culture medium in a proportion of about 1:100, and cultured in a shake flask at 37° C. until OD is approximately 1.0, and then added 0.1-1 mM IPTG for inducing expression. After about 3 to 6 hours, the bacterium were collected centrifugally, and the collected precipitated bacterium could be stored at −20° C. to −80° C. in a refrigerator for later use or be used directly for purification of the PA N-terminal protein.

Expression and Purification of Complex of C-terminal of Influenza Virus PA and PB1 Polypeptide The C-terminal (amino acids 257-716) of the influenza virus PA was cloned into a pGEX-6p vector (from Amersham Pharmacia Inc.) via a molecular cloning technique, the cloning sites thereof being BamHI and NhoI. Expression plasmids with a PA C-terminal gene, obtained by cloning, were transformed into *Escherichia coli* BL21 for protein expression, such that the bacteria could express the N-terminal (amino terminal) of the protein which was connected with the GST fusion protein and has protease cleavage sites cleaved by ProScission protease to further separate a GST protein tag from the target protein-PA polypeptide. IPTG with a final concentration of about 0.1-1 mM was used in the cultured *Escherichia coli* BL21 cells to induce *Escherichia coli* in order to obtain the expressing bacteria of said protein. The used vector contained an ampicillin-resistance gene. After the cloning-constructed expression plasmids of the fusion protein were transformed into *Escherichia coli* such as BL21 (Novagen), bacterium were cultured overnight using bacteria culture media such as LB and so on at 37° C., and after about 12 hours transferred to a mass culture medium in a proportion of about 1:100, and cultured in a shake flask at 37° C. until OD is approximately 1.0, and then added 0.1-1 mM IPTG for inducing expression after the culture temperature is lowered to 16° C. After about 12 to 24 hours, the bacteria were collected centrifugally, and the collected precipitated bacterium could be stored at −20° C. to −80° C. in a refrigerator for later use or be used directly for purification.

The gene of the N-terminal of PB1 with no more than 48 amino acids (the inventor had expressed the former 48-amino acid polypeptide and the former 25-amino acid polypeptide of the N-terminal of PB1) was likewise cloned into multiple cloning sites of the pGEX-6p vector, wherein the used cloning sites were BamHI and XhoI, such that the bacteria could express a fusion protein containing GST, there is protease cleavage sites cleaved by ProScission protease in the fusion protein in order to further separate a GST protein tag from the target protein of PB1 polypeptide. The fusion protein of a GST-PB1$_N$ peptide was expressed in *Escherichia coli* BL21 in the same way as the PA fusion protein was expressed above. The resistance gene was ampicillin-resistance gene. The protein expression was carried out at 37° C., and the used inducer was IPTG. Finally, the expressing bacterium were collected centrifugally, used directly for protein purification and could be stored temporarily at −20° C. to −80° C. in a refrigerator.

The centrifugally collected expressing bacteria expressing the GST-PA N-terminal polypeptide was suspended using a buffer solution containing 20 mM Tris-HCl (pH 8.0) and 250 mM NaCl or a buffer solution of 1×PBS (pH 7.4) phosphoric acid. An ultrasonic breaker was used to break cells. The insoluble precipitation was centrifugally separated and removed in order to collect soluble supernatant. A Glutathione affinity chromatographic column was used to purify the GST-PA-N-terminal polypeptide, and the ProScission protease was further used to enzymolyze the fusion protein into two fragments of GST (glutathione S-transferase) and PA-N. Ion exchange chromatography and gel exclusion chromatography were then used to purify the PA-N protein polypeptide. The protein was concentrated to 5-30 mg/mL for crystal growth.

The expressing bacteria expressing the GST-PA$_C$ C-terminal polypeptide and the expressing bacteria expressing the GST-PB1$_N$ short peptide were suspended using a buffer solution containing 20 mM Tris-HCl (pH 8.0) and 250 mM NaCl or a buffer solution of 1×PBS (pH 7.4) phosphoric acid, and then mixed in proportion, such that the molar ratio of the total protein of GST-PA to GST-PB1 was 0.1:1 to 1:0.1, preferably 0.5:1 to 1:0.5, most preferably close to 1:1.

The cell in the mixed bacterial suspension was lysed using ultrasonic wave or other cell lysing methods. An insoluble portion and a soluble portion of the bacterial lysates were centrifugally separated. The supernatant obtained by high speed centrifugation (about 20,000 g) was preliminarily separated using a Glutathione-Sepharose affinity column (from Amersham Pharmacia Inc.) to purify such mixed protein. The protein containing a GST tag could bind to the Glutathione-Sepharose affinity column, while other proteins could not bind to said affinity column. The above mentioned bacterial suspension buffer solution was used to rinse impurity after the protein bound to the affinity column. A suitable amount of ProScission protease (from Amersham Pharmacia Inc.) was used to enzymolyze the mixed GST fusion protein of the affinity column. This process generally needs about 24 hours. Then, the enzymatically cleaved PA$_C$ and PB1$_N$ proteins were further separated using methods of gel filtration superdex-200 (from Amersham Pharmacia Inc.), Q sepharose ion exchange chromatography (from Amersham Pharmacia Inc.) and so on to purify the PAC/PB1$_N$ short peptide complex (the chromatography column comes from Amersham Pharmacia Inc.). The protein purity was determined via SDS-PAGE gel electrophoresis, and the purity generally reached more than 90%. The protein purified by the above steps was concentrated to about 5-30 mg/mL using an evaporating pipe (coming from Millipore Inc.) for a further crystallization experiment.

The person skilled in the art would know that, the N-terminal of influenza virus PA-PAN and the C-terminal of influenza virus PA-PAC as well as the N-terminal of PB1-PBN could be expressed not only in the prokaryotic cell such as *Escherichia coli* described hereinabove but also in an eukaryotic cell such as insect cells; any other endonuclease, protease cleavage site, and ligase could be used; the target polypeptide to be purified may be fused with other tags such as GST, and the corresponding separating and purifying method was then selected for purification, and finally the tag fused into the target polypeptide was removed. Various change and modification of the present invention as described above fall within the scope of protection of the present invention.

It shall be noted that, the fragments of an α helix and a β sheet of type B or type C influenza corresponding to type A influenza virus are as shown in FIGS. 1A, 1B and 1C as well as FIGS. 10A and 10B, respectively. Herein, the description thereof is omitted.

EXAMPLE 2

Crystallization of PAC/PB$1_N$ Short Peptide Complex

The complex of the PA and PB1 polypeptides expressed and purified with the above method was concentrated to about 5 to 30 mg/mL. A crystallization reagent (from reagent kits such as Screen Kit I/II, Index, and so on from Hampton Research incorporation, etc.) was used in gas sitting drop to screen crystal growth conditions. Upon preliminary screening, the inventor could obtain an original crystal with multiple different crystallization reagents.

Upon further optimization, a crystal with a fairly good appearance was obtained using a solution containing about 1M of sodium acetate in cases of using buffer solutions with different PH values (PH 4-9). A relatively larger triangle-cone crystal was obtained in a sodium acetate buffer solution (PH4-9) with a concentration of 1 to 1.3 M (from Sigma Inc.), the resolution being about 4 Angstrom.

When X-ray diffraction was performed to collect data, crystal needed for the diffraction was transferred from suspension drops to a 10 microliter corresponding crystal buffer solution containing 1.4M sodium acetate and 10% glycerol (from Sigma). The liquid drops were placed in the air for dehydration for more than one hour to obtain a protein crystal with a high resolution, and the resolution of parental and selenium-containing (selenium substituted) protein crystal could reach more than 2.9 Angstrom.

It shall be noted that, the fragments of an α helix and a β sheet of type B or type C influenza corresponding to type A influenza virus are as shown in FIGS. 1A, 1B and 1C as well as FIGS. 10A and 10B, respectively. Herein, the description thereof is omitted.

EXAMPLE 3

Crystal Structure of $PA_C$/PB$1_N$ Short Peptide Complex

A set data of parent crystal with a resolution of 2.9 Angstrom from the complex crystal of PA-PB1 N-terminal (this PB1 N-terminal contains 25 amino acids) was first collected by using FR-E X-ray diffractometer (Rigaku) under a wave length 1.5418 Angstrom. Then under wave length of 0.9783 and 0.9785 Angstrom, two sets of data from derivative crystal of selenium atom were collected, i.e. peak and edge, using synchrotron radiometer located at APS, Chicago, USA (station number: SBC 191D; detection screen: ADSC Q315), the resolution of said crystal is about 3.3 Angstrom. The three sets of data were treated by HKL2000 (Otwinowski 1997) and found to have spacegroup of P4(1)2(1)2. Phase was calculated by multi-wavelength anomalous scattering (Hendrickson 1991), and sas file resulted from treatment was searched for selenium atoms by SHELXD (Sheldrick 1998). The protein itself has 14 methionines, and the inventors found 14 selenium atoms in all. Coordinates of selenium atoms and two sets of data (i.e. Peak and Edge) were input into Program autoSHARP (Vonrhein, Blanc et al. 2007) to calculate phase and to modify the electron density map, and several secondary structures (including α helixes and β sheets) can be clearly found from the calculated electron density map. Then phase can be expanded by Program CAD, and the phase was expanded to 2.9 Angstrom by collected parent data so as to construct a structure model, wherein the Programs used to construt model are ARP/wARP (Perrakis, Morris et al. 1999) and Phenix (Adams, Grosse-Kunstleve et al. 2002). Automatic model construction performed by these two programs can amount to 60% of the whole structure, and the rest is manually constructed through Program COOT (Emsley and Cowtan 2004).

Finally, the resulting model was modified by Program CNS (Brunger, Adams et al. 1998) and REFMAC5 (Murshudov, Vagin et al. 1997) to achieve the protein structure analysis, and the final factor R and factor R-free for modify structure are 0.23 and 0.26 respectively.

EXAMPLE 4

Crystallization of N-terminal of PA

The PA N-terminal polypeptide complex expressed and purified by the above method was concentrated to about 5 to 30 mg/mL. A crystal agent (kits such as Screen Kit I/II, Index, and so on from Hampton Research Incorporation, etc.) was used in gas sitting drop to screen crystal growth conditions. Upon preliminary screening, the inventor obtained an original crystal with different crystal agents.

For further optimization, a crystal well diffracted by an X-ray was obtained from a solution containing about 20% PEG 8000 or 20% PEG 3350 and 0.1 M magnesium chloride or 0.1 M magnesium acetate in a case of using a MES buffer solution with –PH 6.5 (all the used regents came from Sigma Inc.) (see A and B crystal pictures and C and D diffraction pictures in FIG. 3). The X-ray diffracting resolution of the obtained crystal is about 2 to 4 Angstrom.

EXAMPLE 5

Method for Screening Small Molecules Competing with PB$1_N$ for Binding to $PA_C$ During a process of screening a small molecular medicament capable of disintegrating the $PA_C$/PB$1_N$ short peptide complex, the PB$1_N$ short peptide gene was fused with a gene expressing GFP (green fluorescent protein). The PB$1_N$ short peptide protein fused with GFP was expressed as an indicator molecule during a small molecular compound disintegrating a protein complex. The PB1 short peptide gene fragment was connected to the GFP gene fragment using a molecular cloning method so as to express PB1 small peptide fusion protein of which one N-terminal or C-terminal was connected with GFP.

Method 1: a complex of PA C-terminal fusion protein with the N-terminal fused GST, viz. GST-$PA_C$ fusion protein, and GFP-PB$1_N$ short peptide fusion protein was expressed with the above method of expressing and purifying the C-terminal of PA and the PB1 short peptide. The complex of the GST-$PA_C$ fusion protein and the GFP-PB$1_N$ short peptide fusion protein flew through and bound to the Glutathione affinity column. Since said complex contained the GFP protein, the GFP-PB$1_N$ fusion protein binding to GST-$PA_C$ enabled the affinity column to show a green color after GST-$PA_C$ bound to the affinity column. The affinity column binding with the complex protein of GST-$PA_C$ and GFP-PB$1_N$ was rinsed sufficiently with a buffer solution to thoroughly elute and remove unbound proteins. Then, a mixture of small molecular compounds to be screened flew through the affinity column (said mixture should not contain Glutathione or other eluted compounds for detaching GST from the affinity column). If the mixture contained small molecules substituted for the PB$1_N$ polypeptide to bind to the $PA_C$, part of the GFP-PB$1_N$ polypeptide fusion protein binding to PAc was replaced and eluted. The eluted solution flowing out showed a green color due to containing said GFP fusion protein when observed under a fixed wavelength fluorescent microscope. The small molecules were further sequentially separated and purified from the mixture, and the components substituted for the $PB1_N$ polypeptide were traced by the above green GFP protein tracing method to finally determine a small molecular compound interfering with the binding of PA to the PB1 small peptide. In the above method, besides using GST as an affinity matrix, other polypeptides such as Flag-tag, Myc-tag, MBP (Maltose binding protein)-tag, specific antibody, etc. could be used as combining groups of affinity matrix. Correspondingly, the affinity chromatographic column needs a corresponding affinity matrix, for example, if the Flag-tag was used, an antibody against the Flag-tag (e.g. an anti-flag monoclonal antibody from Sigma Inc.) was used to be fixed to the affinity chromatographic column as a gel medium binding to the Flag. The compound molecules binding to PA and replacing a PB1 small peptide (specific structure) could be determined via methods such as mass spectrometry, etc.

Method 2: $PA_C$ was purified separately (fusion protein or non-fusion protein) and covalently crosslinked to a gel medium by chemical crosslinking, but protein was not denatured. $GFP-PB1_N$ flew through the covalently binding gel column. $GFP-PB1_N$ bound to the $PA_C$ protein such that the gel column presents a green fluorescent light of GFP. The solution of the small molecular mixture flew through the gel column, if a compound substituted for $GFP-PB1_N$ to bind to $PA_C$ was present, the $GFP-PB1_N$ fusion protein was eluted. The eluent showed a green color by stimulation of a specific-wavelength light, and the compound molecules substituted for $GFP-PB1_N$ bound to the $PA_C$ molecules of the gel column. A buffer solution was used to elute the gel column to remove impurities, and urea and the like was then used to denature $PA_C$ in order that the small molecules binding thereto were eluted. Methods of mass spectrometry and the like were used to analyze small molecules binding to PA to obtain structural information of the small molecules. The compound may be a small molecular medicament capable of disintegrating the $PA_C/PB1_N$ short peptide complex.

EXAMPLE 6

Method of Using Crystal Three-Dimensional Structure of $PAC/PB1_N$ Complex to Design and Screen Various Polypeptides, Proteins, or Inorganic or Organic Compounds for Treating Diseases Caused by Influenza Virus Infection A crystal three-dimensional structure of a complex of the C-terminal of influenza virus polymerase subunit $PA-PA_C$ and the N-terminal of influenza virus polymerase subunit $PB1-PB1_N$ was used to design and screen various polypeptides, proteins, or inorganic or organic compounds for treating diseases caused by influenza virus infection. The specific steps are as follows: polypeptides and compound molecules binding to specific portion were designed through computer stimulation technology according to coordinates of three-dimensional structure of protein; potential polypeptides and compound molecules binding to specific portion were searched for through computer stimulation technology according to coordinates of three-dimensional structure of protein; the polypeptides and compound molecules designed or searched according to the coordinates of three-dimensional structure of protein bound to any type of influenza virus polymerase protein which has at least 50% sequence identity with the $PA_C$ and $PB1_N$ sequences, and binding information was then analysed; the polypeptides and compound molecules designed or searched according to the coordinates of three-dimensional structure of protein bound to any type of influenza virus polymerase protein which has at least 50% sequence identity with the $PA_C$ and the $PB1_N$ sequences, and then crystallized; and the binding information of the polypeptides or compound molecules to protein is analyzed through a crystal diffraction method.

EXAMPLE 7

Designing and Screening Small Peptides Using Crystal Three-Dimensional Structure of $PAC/PB1_N$ for Treating Diseases Caused by Influenza Virus Infection Upon verification by experiment, a short peptide containing M1, D2, V3, N4, P5, T6, L7, L8, F9, L10, and K11 bound to the C-terminal of PA. The inventors cloned gene encoding $PB1_N$ polypeptide containing the first-position M1 to the eleventh-position K11 into a pFEX-6p vector, purified said $GST-PB1_N$ fusion protein, and used the fusion protein fixed to the affinity chromatographic gel column to bind to PA-C in a solution through an in vitro binding experiment. The inventors found that said fusion protein maintained the $PB1_N$'s capability of binding to PA-C.

Using the same experimental method, the inventors found that a fusion protein containing M1, D2, V3, N4, P5, T6, L7, L8, F9, L10, K11, V12 and p13 also maintained the $PB1_N$'s capability of binding to PA-C. Thus, these two short peptides had a capacity of binding to PA-C to make themselves potential polypeptide medicaments interfering with influenza virus polymerase activity or models for further medicament design.

Likewise, the selected polypeptide having at least three amino acid sequence alignment identical with the above polypeptide might be a potential polypeptide medicament interfering with influenza virus polymerase activity.

The structure of subunits PA, PB1, PB2 or the complex of PA, PB1 and PB2 of any type of influenza virus polymerase contains one protein or one fragment thereof having at least 40% sequences identical with those of the $PA_C$ protein.

In the structure of subunits PA, PB1, PB2 or the complex of PA, PB1 and PB2 of any type of influenza virus polymerase, at least 40% coordinates of main chain carbon backbone of three-dimensional structure of one protein or one fragment thereof has average root mean square deviation smaller than or equal to 1.7 Angstrom with respect to the atomic coordinates of $PA_C$.

In the structure of subunit PA, PB1, PB2 or the complex of PA, PB1 and PB2 of any type of influenza virus polymerase, the protein fragment has 40% sequence identity of 2-12 amino acid fragments of the $PB1_N$ polypeptide.

Any polypeptide or small molecule that interacts with key amino acids of the influenza virus subunit PA is included in the invention.

The structure is used in medicament screening and medicament designing.

A method for screening a compound or polypeptide binding to a protein based on the three-dimensional structure of the $PA_C$ and $PB1_N$ comprises: obtaining a crystal of the complex of $PA_C$ and $PB1_N$ proteins by protein crystallization, wherein the crystal of the complex protein has a spacegroup of P4(1)2(1)2, and the crystal cell parameters are: a=b32 122 Angstrom, c=133 Angstrom, and α=β=γ=90°; obtaining the coordinate of the three-dimensional structure of the complex of the $PA_C$ and $PB1_N$ proteins by an X-ray diffracting crystal technique, wherein any structure containing at least 40% amino acid residues of which coordinates of main chain carbon backbone have average root mean square deviation smaller than or equal to 1.7 Angstrom with respect to said coordinate is included.

A method of expressing and purifying influenza virus subunit PA comprises expressing PA in segments in a bacteria or a eukaryotic expressing system, and the method is used to express and purify any protein fragments which has 40% sequence identity with PA.

In a preferred embodiment, the $PA_C/PB1_N$ complex is used in designing and screening polypeptides, proteins, compounds, or medicaments in the treatment of diseases caused by influenza virus infection.

In a preferred embodiment, polypeptides for treating diseases caused by the influenza virus infection comprises polypeptides interacting with the above complex, at least one of the α helix or β sheet, and at least one amino acid site.

In a preferred embodiment, proteins for treating diseases caused by the influenza virus infection comprises proteins interacting with the above complex, at least one of the α helix or β sheet, and at least one amino acid site.

In a preferred embodiment, compounds for treating diseases caused by the influenza virus infection comprises compounds interacting with the above complex, at least one of the α helix or β sheet, and at least one amino acid site.

In a preferred embodiment, a pharmaceutical composition comprises the above polypeptides, proteins, or compounds.

The pharmaceutical composition of the present invention generally includes one carrier or excipient. An antibody and/or immunoconjugate are dissolved in a pharmaceutically acceptable carrier, wherein an aqueous carrier is preferred. Many types of aqueous carriers can be applied, e.g. buffer saline, etc. These solutions are sterilized and generally free from undesired substances. These components can be disinfected through a conventional, well-known disinfecting technique. These components may include auxiliary substances required by physiological conditions, such as a buffering agent adjusting PH, toxicity regulator, sodium acetate, sodium chloride, potassium chloride, calcium chloride, sodium lactate, etc. The fusion proteins of these components vary greatly in concentration mainly depending on the selected administration manner, the liquid amount and viscosity required by a patient, body weight, etc.

Therefore, about 1.2 to 1200 μg of one typical pharmaceutical immunotoxin component in the present invention shall be applied daily for brain administration. One typical component for treating neoplasms of breast, ovary and lung via intravenous administration shall be applied to one patient 0.1 to 10 mg per day. The dosage of 0.1 to 100 mg per day for one person may be allowed, especially in a case that the medicament is administrated to a closed position without entering blood circulation or a lymphatic system, for example, it is administrated to a body cavity or an organ lacuna. The actual procedures for preparing applicable medical components are understood or acquired by the person skilled in the art and are described in detail in some publications, e.g. Remington's PHARMACETUTICAL SCIENCE, $19^{th}$ ed., Mack Publishing Company, Easton, Pa. (1995).

The components of the present invention can be used for a treatment. In treatment application, the components are applied to a patient suffering from a certain disease (for example, glioblastoma, breast cancer, ovarian cancer, and lung cancer), the dosage of which shall be enough to at least alleviate or partially control said disease and the complications thereof. The dosage enough to complete these tasks is called as "therapeutically effective dosage". The applied effective dosage depends on illness severity and patient's general health conditions. The effective dosage of the component can achieve subjectively-recognized alleviation of a certain symptom or objective improvement recorded by a clinician or other qualified observer.

Whether to be administrate once only or for several times depends on desired and tolerated dose and frequency by a patient. Nevertheless, an adequate amount of the immunotoxin shall be provided to treat a patient effectively. Preferably, the medical dosage might be administrated only once or administrated periodically until a certain therapy efficacy or an adverse reaction inhibits continuation of the treatment. Generally, these dosages are enough to treat or improve disease conditions without incurring unbearable toxicity for a patient.

The immunoconjugate of the present invention can be prepared into gastrointestinal sustained release formulations (e.g. an implant, an oil injection, or a microparticle system). A protein delivery system can be fully understood by referring to Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995). The microparticle system includes microspheres, particles, microcapsules, nano-microcapsules, nano-microspheres, and nano-particles. The microcapsule uses therapeutic protein as a core. In globules, therapeutic substances are dispersed in the particles. Particles, microspheres, and microcapsues which are smaller than about 1 μm are generally called as nano-microparticles, nano-spheres, and nano-microcapsules. Capillary vessels are about 5 μm in diameter. Therefore, only nano-particles are intravenously administrated. The microparticles are about 100 μm in diameter and are intravenously and intramuscularly administrated. Examples are Kreuter, J., COLLOIDAL DRUG DELIVERY SYSTEMS, J. Kreuter, ed., Marcel Dekker, Inc., New York, N.Y., pp. 219-342 (1994); and Tice&Tabibi, TREATISE ON CONTROLLED DRUG DELIVERY, A. Kydonieus, ed., Marcel Dekker, Inc. New York, N.Y., pp. 315-339, (1992), both of which are cited herein.

Polymers can be used for ion controlled release of immunoconjugate components in the present invention. Multiple degradable and nondegradable polymers for drug controlled release are well-known in the art (Langer, R., *Accounts Chem. Res.* 26:537-542 (1993)), for example, a retarding polymer polaxamer 407 is viscous and flowable at low temperature, but is formed as a semisolid gel at body temperature, and is proved to be an effective carrier for forming and delivering continuously recombinant interleukin-2 and urease (Johnston etc., *Pharm. Res.* 9:425-434 (1992)) and Pec etc., *J. Parent. Sci. Tech.* 44(2):58-65(1990)). Likewise, hydroxyapatite can be used as a microcarrier for protein controlled release (Ijntema etc., Int. J. Pharm. 112:215-224 (1994)), while liposome is used for controlled release and targeting transport processes of a liplid-coated medicament (Betageri, etc., LIPOSOME DRUG DELIVERY SYSTEMS, Technomic Publishing Co., Inc., Lancaster, Pa. (1993)). Many other therapeutic protein controlled release systems have been known, for example, U.S. Pat. Nos. 5,055,303, 5,188,837, 4,235,871, 4,501,728, 4,837,028, 4,957,735, 5,019,369, 5,055,303, 5,514,670, 5,413,797, 5,268,164, 5,004,697, 4,902,505, 5,506,206, 5,271,961, 5,254,342, and 5,534,496, any of which is cited herein.

Experimental Results

The atomic coordinate of the structure of the complex of $PA_C$ and $PB1_N$ is shown in the following Table 1.

Polymerase subunit PA protein derived from avian H5N1 influenza virus strains A/goose/Guangdong/1/96 is compared with PA protein sequences of type A influenza virus strains A/BrevigMission/1/1918 that outbreaks on a large scale in Europe, 1998, and two types of type B influenza virus strains B/Ann Arbor/1/1966 and type C influenza virus strains C/JJ/1950, the results of which are as shown in FIG. 1.

PA (SEQ ID NO:1) is divided by the inventor into two parts, and multiple fragments of varying lengths of two parts of a PA gene are cloned and expressed in *Escherichia coli*, wherein residues 1-256 (see FIG. 1 and FIG. 2) and residues 257-716 (see FIG. 4A) of the N-terminal of PA are well expressed and purified by being fused with GST (Glutathione S-Transferase) and a well-diffracted parental crystal of purified PA amino-terminal (PA_N) is obtained (see FIG. 3).

A preliminary crystallization experiment shows that the C-terminal of PA fails to obtain a crystal despite a lot of efforts has been made. Therefore, the inventor also uses a GST fusion method to express PB1 N-terminal peptides of 25 amino acids and 48 amino acids (see FIG. 4A, which is an electrophoretogram before and after the C-terminal of PA is fused with the GST or the N-terminal of PB1 is fused with the GST, wherein strand 1 PA_C CT is a control sample for the C-terminal of PA, strand 2 GST-PB1+$PA_C$ is a sample in which the complex of the C-terminal of PA and the N-terminal of PB1 is fused with GST, strand 3 GST-PB1 is a sample in which the $PB1_N$ terminal is fused with GST, strand 4 GST+PA_C is a sample in which the C-terminal of PA is fused with GST, and strand 5 GST CT is a GST control sample; wherein PA_C denotes an electrophoretic band of PA_C, GST-PB1 is an electrophoretic band in which the $PB1_N$ terminal is fused with GST, and GST is a control electrophoretic band for GST). The results show that: GST-PB1 can bind to purified PA_C protein.

The in vitro binding experiment shows that the expressing bacterium of the corresponding polypeptides of PA and PB1 are mixed in proportion, and then these two proteins are co-purified through the Glutathione affinity column and gel exclusion chromatograph, and so on. It is determined therefrom that the co-purification of the two can be realized, indicating the purified 460 amino acids of the C-terminal of PA may form a stable complex with the GST-PB1 polypeptide.

Further, the $PA_C/PB1_N$ polypeptide complex is separated and purified after using protease to cleave the GST fusion peptide and then used in a crystallization experiment to obtain a crystal under multiple conditions, wherein a well-diffracted crystal is obtained under one condition. However, the separately purified PA C-terminal protein fails to obtain a crystal, implying that the addition of PB1 polypeptide helps to stabilize the PA protein.

Three-Dimensional Structure of $PA_C/PB1_N$ Polypeptide Complex

A method of MAD is used to analyze a crystal structure of a complex of PA C-terminal 460 amino acids and PB1 N-terminal 25 amino acids, wherein the resolution is 2.9 Angstrom, the finally corrected R factor is 23%, and the $R_{free}$ factor is 26%. In general, if the structure is indicated by lines, the PA part is, vividly speaking, like a wolf's head viewed from the side, which has an extruding mouth, a skull thereafter and a ringed neck (FIG. 4B). PB1 is like a bone bite by the mouth of PA. The PA part mainly comprises 13 α helixes, one small $3_{10}$ helix, 7 β sheets and loops connected the preceding structures (FIGS. 1, 4B, and FIG. 5). In terms of structure, the PA protein part can be deemed to have two domains. One domain is an area binding to the PB1 polypeptide (domain I, viz. the first part of the PA C-terminal structure) and is composed of helixes and loops, wherein helixes 4, 5, 8, 9, 10, 11, 12, and 13 constitute the mouth and cheek parts of the wolf's head. Such a domain is relative narrow viewed from the top part of the wolf's head. The other domain (domain II, viz. the second part of the PA C-terminal structure) is a latter half part of the wolf's head composed of the remaining helixes and β sheets, which is relatively large viewed from the top, with a large loop connected below, and resembles the neck part of the wolf' head. The N-terminal of the PB1 polypeptide is located on the side surface of the wolf's head, and the C-terminal is located at the other side surface, which are equivalent to two check sides of the wolf's head. PA of the crystal in the present invention is a polypeptide with the PA N-terminal 256 residues removed. It is reported that the N-terminal is a main active area of PA protease, while the other relative far active site Ser624 is located on the other check side. It is thought that Ser624 is an amino acid of the PA protease active centre which constitutes a protease active area together with the removed part of PA. Therefore, the PA N-terminal removed part is located on the other side surface of the cheek. The second domain of the latter half part of the wolf's head is composed of the remaining helixes and β sheets. Seven differently oriented β sheets of varying lengths constitute a slight twisted plane and located in the center position of the domain, while α helixes are distributed at the periphery of the helix and constitute a Rossmann fold structure. There is a large groove at the junction of two domains to form a large loop about 25 Angstrom in diameter with the lower cervical ring (FIG. 5).

Interaction Between PA and PB1 Polypeptide

Helixes binding to the PB1 polypeptide in domain I are helix 4 (406-415), 8 (582-604*aa*), 10 (633-650*aa*), 11 (653-674*aa*), and 13 (698-714*aa*), wherein three helixes (8, 11, 13) extend outwards nearly in parallel to form a nearly right-angled triangle viewed from a helix axis direction, the fourth helix (10) extends obliquely, the PB1 polypeptide is interposed therebetween (FIG. 5 and FIG. 6), and helix 4 interacts with the $PB1_N$ peptide residue on the side surface. Four helixes forms a hydrophobic core in a region binding to the PB1 polypeptide, and the side chains thereof and the hydrophobic amino acid residues of PB1 are combined together by means of hydrophobic interaction and hydrogen bonds. The second-position aspartic acid to the fifteenth-position glutamine of the PB1 polypeptide can be observed in an electron density map. Such a result coincides with the previous 12 amino acids of the $PB1_N$ terminal are key amino acids for PA binding to PB1 reported by Perez, etc. (Perez and Donis 2001). Further, the inventors analyze interaction between these amino acid residues and PA. The conserved LLFL peptide fragment of PB1 reported by the articles of Perez, etc. (Perez and Donis 2001) is present in a short helix and suspended in the middle of the hydrophobic core formed by PA. The amino acid residues of PA involved in forming the hydrophobic core are Leu666 of helix 11, Phe710 of helix 13, and Ile 633, Val636, and Leu640 of helix 10, etc. The amino acids of PA involved in binding to the PB1 polypeptide include Trp706 of helix 13, Gln670 of helix 11, etc., wherein Trp706 interacts with amino acids of Val3, N4, etc. of the PB1 short peptide by means of hydrophobic bonds, van der Waals forces, etc. Gln670 interacts with F9, V12, P13 and A14 of PB1 by means of hydrogen bonds, hydrophobic bonds, van der Waals forces, etc. T639 of helix 10 is involved in the interaction with Val3 (van der Waals forces). Q408 and N412 of helix 4 are involved in the reaction with Val3 and D2 of PB1. In addition, a loose loop interposed between helix 9 and helix 10 is also involved in the interaction with PB1, wherein I621, G622, and E623 interact with D2 and N5, respectively, and T618 and P620 interact with L8 and K11, respectively. Helix 8 is distant from the PB1 polypeptide, mainly due to van der Waals forces. Such a result is substantially consistent with the function of the residues of the PB1 polypeptide being involved in binding reported by the documents. These amino acids involved in binding to PA are conserved across type A, B and C influenza viruses, and the PA residues involved in binding to the PB1 polypeptide are mostly conserved (FIG. 1). The analysis of a fine three-dimensional structure of a mode of binding PA to PB1 provides a powerful three-dimensional information platform for designing corresponding medicaments to inhibit the function of the influenza virus polymerase.

Figure 8:
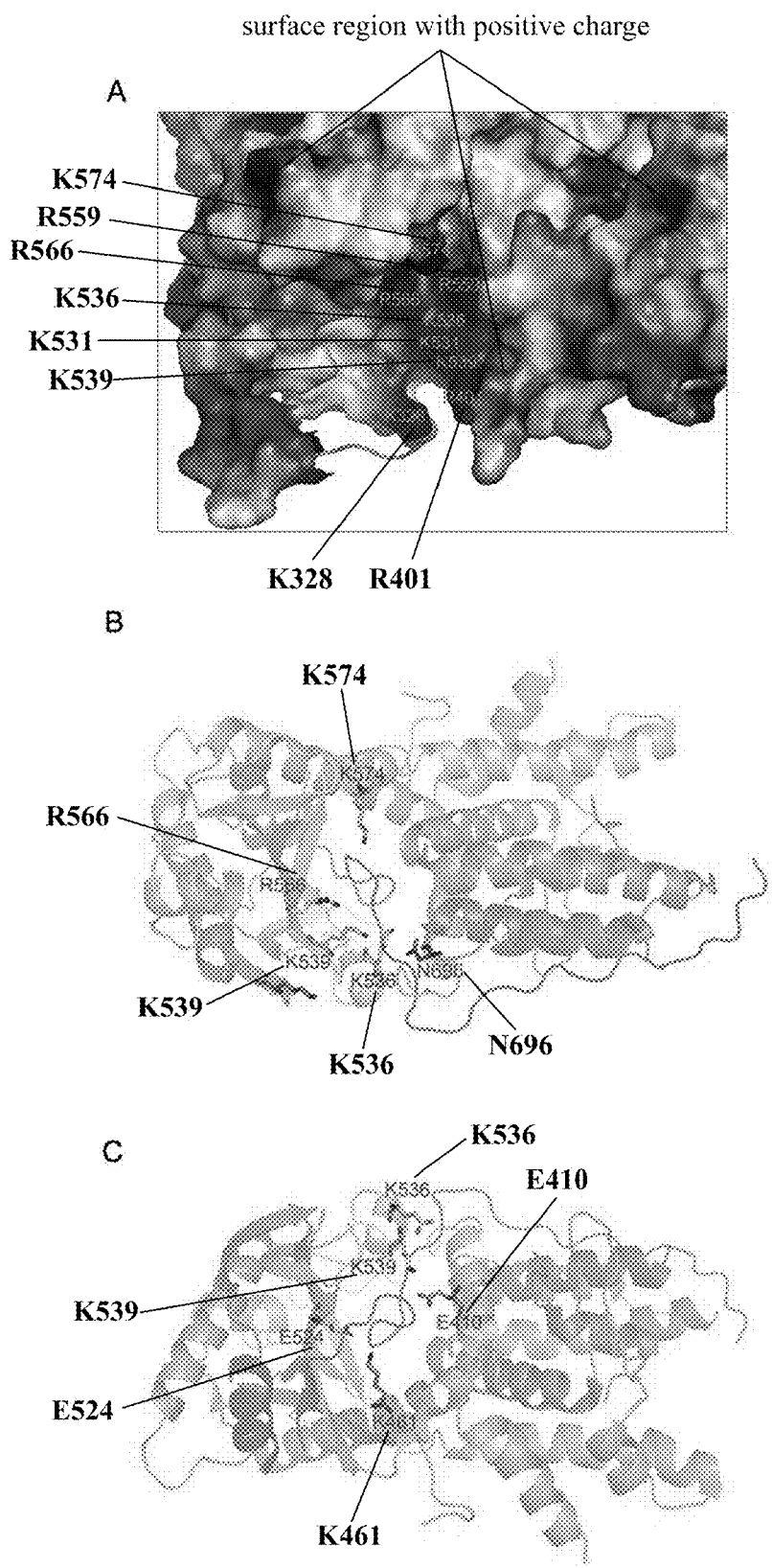
Figure 9:
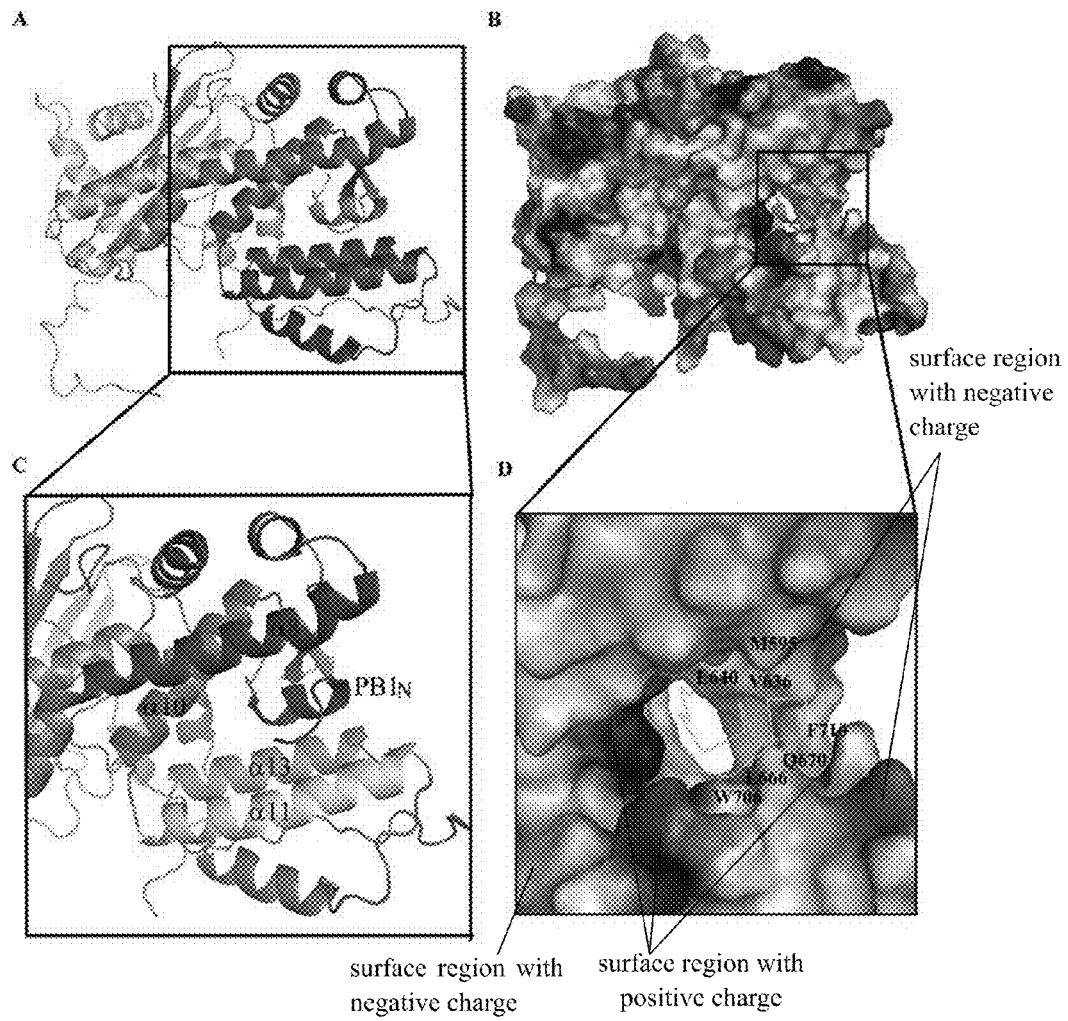

It is found from the results of analyzing the PA structure that a large groove (domain III) is provided at the conjunction of two domains below domain I (FIG. 8A). The surface of the large groove is enriched with basic amino acids, wherein some amino acids, such as K536, K328, R566, and so on, are highly conserved in the three types of influenza viruses. In addition, the 399th-position Lys and 401st-position Arg are also conserved (FIG. 1). Mutants at the sites of K536 and so on prove the importance of these sites, indicating that the large groove part is associated with the binding of nucleotide or RNA. In addition, a large annular chain part is provided below the groove. This fragment of polypeptide is formed by being pulled apart via interaction between the annular polypeptide fragment with another neighboring molecular surface in crystal packing. The electron density of part of amino acids can not be observed clearly. The large groove and the neck ring constitute a large loop about 25 Angstrom in diameter, and such a space is enough to accommodate a double RNA helix. As described above, on the surface of the groove inside the ring, there are mainly distributed conserved basic amino acids. Although the amino acids of the chain fragment are not highly conserved, the three types of influenza viruses are mainly composed of acidic amino acids. The conservativeness and structure specificity of the groove and the annular structure in the PA molecule imply their critical roles in the polymerase to make them become second drug targets besides the area in which PA binds to PB1.

RNA promoter binding capacity. In terms of the structure analyzed by the inventors, the inventors find that the large groove is a binding site for nucleotide or RNA, wherein the sites of K539, E538, and K328 are highly conserved across the three types of influenza viruses. The inventors deem that these amino acids are involved in binding to RNA nucleotide, especially in binding to RNA, indicating that the PA subunit plays an important role in binding to a promoter, RNA, and a process of RNA synthesis.

Between domain I and domain II, the helixes of domain I and the β sheets of domain II form a channel with a diameter of about 8 Angstrom to 15 Angstrom (FIGS. 8B and 8C). In such a structure analyzed by the inventors, one loose fragment of the N-terminal of PA resembles a rope lying in the channel. Since the N-terminal fragment is relatively far from the two ends of the channel, the inventors think that the N-terminal fragment is absent from the channel when the polymerase complex interacts with other host proteins to exhibit the polymerase's function. Thus, a channel is present in the middle of the domain, extending through the channel from the PA groove to the other side of the cheek of the wolf's head. On the surface of the channel, there exist some amino acids which are highly conserved in the three types of influenza viruses, e.g. R566, K539, and K574 located on the surface of the large groove, conserved E410, K460, E524, and K536 in the middle of the channel, and the like. It is found that some residues thereof have an influence on the polymerase activity. The researches of Fodor, etc. indicate that mutation of E524A abolishes the virus's capacity of RNA synthesis to inhibit virus production. Mutation of E410 decreases the polymerase activity (Fodor, Crow et al. 2002). Mutation of K539A is found not to influence mRNA synthesis but significantly influence gene replication of cRNA and vRNA, indicating that such an area is critical for replication of viral genome. It is known that the nucleotide has a size close to that of the channel (e.g. ATP has a length of about 14 Angstrom and a width of about 8 Angstrom, and other three nucleotides UCG have a size similar thereto). The inventors, thus, deem that such a channel allows the passage of nucleotide or other small molecules or interaction with other proteins in some cases. Therefore, the mutation of the surface residues will cause significant change of the polymerase activity. The unique structure and the functional importance of the channel make it become a third drug designing site for binding target.

In a specific embodiment, there is provided in the present invention a polypeptide, a protein, an inorganic compound, or an organic compound competing with the influenza virus polymerase PB1 to bind to $PA_C$, wherein the amino acid sequences of the polypeptide or protein contain a short LLFL motif of the short helix region formed by the $PB1_N$ residues 5 to 11 of wild type influenza virus polymerase PB1.

Herein, part of atoms between Met595 and Val12, between Leu666 and Phe9, between Leu640 and Leu8, between Leu636 and Leu8, between Met628 and Leu7, between Phe710 and Thr6, between Trp706 and Thr6, between Trp706 and Pro5, between Phe411 and Pro5, and between Trp706 and Asn4 are involved in interaction within the scope of 4 Angstrom. Therefore, it can be seen that they bind to one another by means of hydrophobic interaction. Thus, polypeptides or compounds involved in hydrophobic interaction with the corresponding amino acids of the C-terminal of PA can be used as medicaments for inhibiting influenza virus.

There are many successful examples for designing a medicament based on a structure of target protein (Schneider, G. and Fechner, U., Nature Reviews Drug Discovery 2005, 4, 649). The LigBuilder program developed by the research group set up by Professor Lu Hua from Peking University has more than 700 worldwide registration users (Wang, R. X.; Gao, Y.; Lai, L. H., LigBuilder: A multi-purpose program for structure-based drug design. J. Mol. Mod. 2000, 6, 498). Many examples has been reported of designing a highly active inhibitor successfully using the LigBuilder program, for example, the Boehringer Ingelheim pharmaceutical company uses LigBuilder 1.2 to access and implement aided design for optimizing a highly active kinase inhibitor (Goldberg D R, Hao, M-H., et al., J. Med. Chem. 2007, 50, 4016).

Novel medicament design and calculation is conducted using the LigBuilder 2.0 program according to the crystal structure of the $PAC-PB1_N$ complex of the H5N1 virus RNA polymerase. First, directed at the PAC protein, an analysis of binding sites is made, wherein two binding sites wining highest scores are located in the "mouth" region and the "channel" region of the structure. Novel medicament design and calculation for these two sites are conducted using the LigBuilder 2.0 program to obtain some easily-synthesized compounds with high prediction activity.

Molecules binding to the "channel" region of the PA molecules are exemplified as follows:

Compound 1

R$_1$ = —CH$_3$, —CH$_2$CH$_3$
R$_2$ = —CH$_3$, —CH$_2$NH$_2$, —CH(OH)CH$_3$, —CH(CH$_3$)$_2$
Predicted Kd: 8.64 to 9.60

Compound 2

R$_1$ = —NH$_2$
R$_2$ = —COCH$_3$, —CH$_2$COCH$_3$, —CO, —OCH$_2$CH$_3$
R$_3$ = —CH$_2$NH$_2$, —CH$_2$(NH$_2$)CH$_2$CH$_3$, —CH$_2$(NH$_2$)CH$_2$CH$_2$CH$_3$
Predicted Kd: 8.51 to 9.65

Molecules binding to the "mouth" region of the PA molecule are exemplified as follows:

Compound 3

R$_1$ = —OH
R$_2$ = —OH, —CO, —CONH$_2$, —CONHCH$_3$, COOH
R$_3$ = —COOH, —NH$_2$, —C(NH$_2$)$^{2+}$
R$_4$ = —CH(OH)CH$_3$, CONH$_2$, CH(NH$_2$)CH$_2$OH
Predicted Kd: 8.52 to 8.96

Compound 4

R$_1$ = —OH, —NHCO
R$_2$ = —CH$_2$(OH)CH$_3$, —NHCH$_3$, —CH$_2$OH, —CH$_2$NH$_2$, —NH$_2$, —C(NH$_2$)$^{2+}$
R$_3$ = —NH$_2$, —C(NH$_2$)$^{2+}$, —CH$_2$OH, —CO, —CH$_2$CO, —NHCO
R$_4$ = —OH, —OCH$_3$

REFERENCE

Adams, P. D., R. W. Grosse-Kunstleve, et al. (2002). "PHENIX: building new software for automated crystallographic structure determination." Acta Crystallogr D Biol Crystallogr 58(Pt 11): 1948-54.

Brunger, A. T., P. D. Adams, et al. (1998). "Crystallography & NMR system: A new software suite for macromolecular structure determination." Acta Crystallogr D Biol Crystallogr 54(Pt 5): 905-21.

Deng, T., J. Sharps, et al. (2005). "In vitro assembly of PB2 with a PB1-PA dimer supports a new model of assembly of influenza A virus polymerase subunits into a functional trimeric complex." J Virol 79(13): 8669-74.

Deng, T., J. L. Sharps, et al. (2006). "Role of the influenza virus heterotrimeric RNA polymerase complex in the initiation of replication." J Gen Virol 87(Pt 11): 3373-7.

Emsley, P. and K. Cowtan (2004). "Coot: model-building tools for molecular graphics." Acta Crystallogr D Biol Crystallogr 60(Pt 12 Pt 1): 2126-32.

Fodor, E., M. Crow, et al. (2002). "A single amino acid mutation in the PA subunit of the influenza virus RNA polymerase inhibits endonucleolytic cleavage of capped RNAs." J Virol 76(18): 8989-9001.

Fodor, E., D. C. Pritlove, et al. (1994). "The influenza virus panhandle is involved in the initiation of transcription." J Virol 68(6): 4092-6.

Hara, K., F. I. Schmidt, et al. (2006). "Amino acid residues in the N-terminal region of the PA subunit of influenza A virus RNA polymerase play a critical role in protein stability, endonuclease activity, cap binding, and virion RNA promoter binding." J Virol 80(16): 7789-98.

Hara, K., M. Shiota, et al. (2001). "Influenza virus RNA polymerase PA subunit is a novel serine protease with Ser624 at the active site." Genes Cells 6(2): 87-97.

Hendrickson, W. A. (1991). "Determination of macromolecular structures from anomalous diffraction of synchrotron radiation." Science 254(5028): 51-8.

Honda, A., K. Mizumoto, et al. (2002). "Minimum molecular architectures for transcription and replication of the influenza virus." Proc Natl Acad Sci U S A 99(20): 13166-71.

Hulse-Post, D. J., J. Franks, et al. (2007). "Molecular changes in the polymerase genes (PA and PB1) associated with high pathogenicity of H5N1 influenza virus in mallard ducks." J Virol 81(16): 8515-24.

Kawaguchi, A., T. Naito, et al. (2005). "Involvement of influenza virus PA subunit in assembly of functional RNA polymerase complexes." J Virol 79(2): 732-44.

Munster, V. J., E. de Wit, et al. (2007). "The molecular basis of the pathogenicity of the Dutch highly pathogenic human influenza A H7N7 viruses." J Infect Dis 196(2): 258-65.

Murshudov, G. N., A. A. Vagin, et al. (1997). "Refinement of macromolecular structures by the maximum-likelihood method." Acta Crystallogr D Biol Crystallogr 53(Pt 3): 240-55.

Otwinowski, Z. M., Wladek (1997). "Processing of x-ray diffraction data collected in oscillation mode" Methods in Enzymology 276 (Macromolecular Crystallography, Part A): 307-326

Perez, D. R. and R. O. Donis (2001). "Functional analysis of PA binding by influenza a virus PB1: effects on polymerase activity and viral infectivity." J Virol 75(17): 8127-36.

Perrakis, A., R. Morris, et al. (1999). "Automated protein model building combined with iterative structure refinement." Nat Struct Biol 6(5): 458-63.

Sanz-Ezquerro, J. J., T. Zurcher, et al. (1996). "The amino-terminal one-third of the influenza virus PA protein is responsible for the induction of proteolysis." J Virol 70(3): 1905-11.

Sheldrick, G. M., Ed. (1998). Direct Methods for Solving Macromolecular Structures. Dordrecht, The Netherlands, Kluwer Academic Publishers.

Sugiura, A., M. Ueda, et al. (1975). "Further isolation and characterization of temperature-sensitive mutants of influenza virus." Virology 65(2): 363-73.

Taubenberger, J. K. and D. M. Morens (2007). "The Pathology of Influenza Virus Infections." Annu Rev Pathol.

Vonrhein, C., E. Blanc, et al. (2007). "Automated structure solution with autoSHARP." Methods Mol Biol 364:215-30.

What we claim:

1. A crystal complex of the influenza A virus polymerase PA-PAc subunit C-terminus and the influenza A virus polymerase PB1-PB1$_N$ subunit, wherein the PA-PAc subunit C-terminus consists of amino acids 257-716 of SEQ ID NO:1, and the influenza A virus polymerase PB1-PB1$_N$ subunit consists of amino acids 2-26 of of SEQ ID NO:2, and wherein said crystal complex is in space group P4$_1$2$_1$2 having unit cell dimension of a=b=122 Angstrom, c=133 Angstrom, $\alpha=\beta=\gamma=90°$.

2. The crystal complex of claim 1, wherein said crystal diffracts X-ray, and the X-ray diffraction pattern is solved to produce the three dimensional structure of the complex defined by the atomic coordinates listed in Table 1, or atomic coordinates having an average root mean square deviation smaller than or equal to 1.7 Angstrom with respect to the atomic coordinates listed in Table 1.

3. The crystal complex of claim 2, wherein the PA-PAc subunit C-terminus interacts with the PB1-PB1$_N$ N-terminus through at least one amino acid of the PA-PAc subunit selected from group consisting of Leu666, Phe710, Val636, Leu640, Trp706 and Gln670 of SEQ ID NO:1.

4. The crystal complex of claim 2, wherein at least one amino acid selected from the group consisting of Ile621, Gly622, Glu623, Thr618 and Pro620 of the PA-PAc subunit of SEQ ID NO:1 interacts with the PB1 subunit.

5. The crystal complex of claim 2, wherein the PA-PAc subunit comprises a pocket structure which interacts with the PB1$_N$ subunit, said pocket structure comprising at least one amino acid selected from the group consisting of Asn647, Gln408, Cys584, Gln587, Gln591, Lys643, Asn647, Ser659, Lys663, Trp699 and Asn703 of SEQ ID NO:1.

6. The crystal complex of claim 2, wherein the PA-PAc subunit comprises groove and channel structures which bind to nucleotides, RNA, or other small molecules or proteins, said groove and channel structures comprising at least one amino acid selected from the group consisting of Trp406, Glu410, Lys461, Glu524, Phe525, Ser526, Lys536, Lys539, Tyr540, Leu563, Tyr564, Arg566 and Lys574 of SEQ ID NO:1.

7. A method of expression and purification of a complex of the influenza A virus polymerase PA-PAc subunit C-terminus, said C-terminus consisting of amino acids 257-716 of SEQ ID NO:1, and the influenza A virus polymerase PB1-PB1$_N$ subunit N-terminus polymerase consisting of residues 2-26 of SEQ ID NO:2 according to claim 3, said method comprising:
(a) Expressing said PA-PAc subunit C-terminus consisting of residues 257-716 of SEQ ID NO:1 and said PB1-PB1$_N$ subunit N-terminus consisting of residues 2-26 of SEQ ID NO:2 in a suitable expression system, where either the PA-PAc subunit C-terminus or the PB1-PB1$_N$ subunit N-terminus is expressed as a fusion protein comprising an affinity tag;
(b) Combining said expressed PA-PAc subunit C-terminus and said PB1-PB1$_N$ subunit N-terminus proteins for a time sufficient for the subunits to complex; and
(c) Isolating and purifying said complex.

8. The method of claim 7, wherein the affinity tag is selected from the group consisting of GST, Flag-tag, Myc-tag, and MBP-tag.

9. The method of claim 8, wherein the expression system is an *Escherichia coli* expression system.

10. A method to obtain a crystal complex of the influenza A virus polymerase PA-PAc subunit C-terminus, said C-terminus consists of amino acids 257-716 of SEQ ID NO:1, and the influenza A virus polymerase PB1-PB1$_N$ subunit consisting of residues 2-26 of SEQ ID NO:2 according to claim 1, said method comprising:
(a) Concentrating a purified complex of the PA-PAc subunit C-terminus and the PB1-PB1$_N$ subunit N-terminus to 5-30 mg/ml; and
(b) Obtaining the crystal from 1-1.3 M sodium acteate, pH 4.9, using the sitting or hanging drop method.

* * * * *

SEQUENCE LISTING

```
<160> NUMBER OF SEQ ID NOS: 8

<210> SEQ ID NO 1
<211> LENGTH: 716
<212> TYPE: PRT
<213> ORGANISM: Influenza virus
<220> FEATURE:
<223> OTHER INFORMATION: polymerase subunit PA protein

<400> SEQUENCE: 1

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asp Glu Arg Gly Glu Ser Thr Ile Ile Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Thr Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Cys Arg Leu Ala Asp Gln Ser Leu Pro Pro Asn Phe Ser
    210                 215                 220

Ser Leu Glu Lys Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asp
            260                 265                 270

Gly Pro Pro Cys Ser Gln Arg Ser Lys Phe Leu Leu Met Asp Ala Leu
        275                 280                 285
```

```
Lys Leu Ser Ile Glu Asp Pro Ser His Glu Gly Glu Gly Ile Pro Leu
    290                 295                 300
Tyr Asp Ala Ile Lys Cys Met Lys Thr Phe Phe Gly Trp Lys Glu Pro
305                 310                 315                 320
Asn Ile Val Lys Pro His Glu Lys Gly Ile Asn Pro Asn Tyr Leu Leu
                325                 330                 335
Ala Trp Lys Gln Val Leu Ala Glu Leu Gln Asp Ile Glu Asn Glu Glu
            340                 345                 350
Lys Ile Pro Lys Thr Lys Asn Met Arg Lys Thr Ser Gln Leu Lys Trp
        355                 360                 365
Ala Leu Gly Glu Asn Met Ala Pro Glu Lys Val Asp Phe Glu Asp Cys
    370                 375                 380
Lys Asp Val Ser Asp Leu Arg Gln Tyr Asp Ser Asp Glu Pro Lys Pro
385                 390                 395                 400
Arg Ser Leu Ala Ser Trp Ile Gln Ser Glu Phe Asn Lys Ala Cys Glu
                405                 410                 415
Leu Thr Asp Ser Ser Trp Ile Glu Leu Asp Glu Ile Gly Glu Asp Val
            420                 425                 430
Ala Pro Ile Glu His Ile Ala Ser Met Arg Arg Asn Tyr Phe Thr Ala
        435                 440                 445
Glu Val Ser His Cys Arg Ala Thr Glu Tyr Ile Met Lys Gly Val Tyr
    450                 455                 460
Ile Asn Thr Ala Leu Leu Asn Ala Ser Cys Ala Ala Met Asp Asp Phe
465                 470                 475                 480
Gln Leu Ile Pro Met Ile Ser Lys Cys Arg Thr Lys Glu Gly Arg Arg
                485                 490                 495
Lys Thr Asn Leu Tyr Gly Phe Ile Ile Lys Gly Arg Ser His Leu Arg
            500                 505                 510
Asn Asp Thr Asp Val Val Asn Phe Val Ser Met Glu Phe Ser Leu Thr
        515                 520                 525
Asp Pro Arg Leu Glu Pro His Lys Trp Glu Lys Tyr Cys Val Leu Glu
    530                 535                 540
Ile Gly Asp Met Leu Leu Arg Thr Ala Ile Gly Gln Val Ser Arg Pro
545                 550                 555                 560
Met Phe Leu Tyr Val Arg Thr Asn Gly Thr Ser Lys Ile Lys Met Lys
                565                 570                 575
Trp Gly Met Glu Met Arg Arg Cys Leu Leu Gln Ser Leu Gln Gln Ile
            580                 585                 590
Glu Ser Met Ile Glu Ala Glu Ser Ser Val Lys Glu Lys Asp Met Thr
        595                 600                 605
Lys Glu Phe Phe Glu Asn Lys Ser Glu Thr Trp Pro Ile Gly Glu Ser
    610                 615                 620
Pro Lys Gly Met Glu Glu Gly Ser Ile Gly Lys Val Cys Arg Thr Leu
625                 630                 635                 640
Leu Ala Lys Ser Val Phe Asn Ser Leu Tyr Ala Ser Pro Gln Leu Glu
                645                 650                 655
Gly Phe Ser Ala Glu Ser Arg Lys Leu Leu Leu Ile Val Gln Ala Leu
            660                 665                 670
Arg Asp Asn Leu Glu Pro Gly Thr Phe Asp Leu Gly Gly Leu Tyr Glu
        675                 680                 685
Ala Ile Glu Glu Cys Leu Ile Asn Asp Pro Trp Val Leu Leu Asn Ala
    690                 695                 700
Ser Trp Phe Asn Ser Phe Leu Thr His Ala Leu Lys
```

```
                                 705                 710                 715
```

<210> SEQ ID NO 2
<211> LENGTH: 757
<212> TYPE: PRT
<213> ORGANISM: Influenza virus
<220> FEATURE:
<223> OTHER INFORMATION: polymerase subunit PB1 protein

<400> SEQUENCE: 2

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Lys Ser His Pro Gly Ile Phe Glu Asn Ser Cys Leu Glu Thr Met Glu
            100                 105                 110

Ile Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Gly Glu Met Glu Ile Ile Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365
```

Pro Ala Glu Met Leu Ala Ser Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ala Glu Ile Met Lys Ile Cys Ser Thr Ile Glu Glu
            740                 745                 750

Leu Arg Arg Gln Lys
        755

<210> SEQ ID NO 3
<211> LENGTH: 716
<212> TYPE: PRT

<213> ORGANISM: Influenza A virus type: A/Brevig Mission/1/1918

<400> SEQUENCE: 3

```
Met Glu Asp Phe Val Arg Gln Cys Phe Asn Pro Met Ile Val Glu Leu
1               5                   10                  15

Ala Glu Lys Ala Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Arg Gly Glu Ser Ile Ile Val Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Arg Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asp
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ala Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Ser Asp Leu Lys Gln Tyr Asp Ser Asp Glu Pro Glu Leu
385                 390                 395                 400

Arg Ser Leu Ala Ser Trp Ile Gln Ser Glu Phe Asn Lys Ala Cys Glu
```

```
                405                 410                 415
Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Arg
705                 710                 715

<210> SEQ ID NO 4
<211> LENGTH: 726
<212> TYPE: PRT
<213> ORGANISM: Influenza B virus type: B/Ann Arbor/1/1966

<400> SEQUENCE: 4

Met Asp Thr Phe Ile Thr Arg Asn Phe Gln Thr Thr Ile Ile Gln Lys
1               5                   10                  15

Ala Lys Asn Thr Met Ala Glu Phe Ser Glu Asp Pro Glu Leu Gln Pro
            20                  25                  30

Ala Met Leu Phe Asn Ile Cys Val His Leu Glu Val Cys Tyr Val Ile
        35                  40                  45

Ser Asp Met Asn Phe Leu Asp Glu Glu Gly Lys Thr Tyr Thr Ala Leu
    50                  55                  60

Glu Gly Gln Gly Lys Glu Gln Asn Leu Arg Pro Gln Tyr Glu Val Ile
```

```
                65                  70                  75                  80
            Glu Gly Met Pro Arg Asn Ile Ala Trp Met Val Gln Arg Ser Leu Ala
                            85                  90                  95
            Gln Glu His Gly Ile Glu Thr Pro Arg Tyr Leu Ala Asp Leu Phe Asp
                           100                 105                 110
            Tyr Lys Thr Lys Arg Phe Ile Glu Val Gly Ile Thr Lys Gly Leu Ala
                           115                 120                 125
            Asp Asp Tyr Phe Trp Lys Lys Glu Lys Leu Gly Asn Ser Met Glu
                130                 135                 140
            Leu Met Ile Phe Ser Tyr Asn Gln Asp Tyr Ser Leu Ser Asn Glu His
            145                 150                 155                 160
            Ser Leu Asp Glu Glu Gly Lys Gly Arg Val Leu Ser Arg Leu Thr Glu
                           165                 170                 175
            Leu Gln Ala Glu Leu Ser Leu Lys Asn Leu Trp Gln Val Leu Ile Gly
                           180                 185                 190
            Glu Glu Asp Ile Glu Lys Gly Ile Asp Phe Lys Leu Gly Gln Thr Ile
                           195                 200                 205
            Ser Lys Leu Arg Asp Ile Ser Val Pro Ala Gly Phe Ser Asn Phe Glu
                210                 215                 220
            Gly Met Arg Ser Tyr Ile Asp Asn Ile Asp Pro Lys Gly Ala Ile Glu
            225                 230                 235                 240
            Arg Asn Leu Ala Arg Met Ser Pro Leu Val Ser Val Thr Pro Lys Lys
                           245                 250                 255
            Leu Lys Trp Glu Asp Leu Arg Pro Ile Gly Pro His Ile Tyr Ser His
                           260                 265                 270
            Glu Leu Pro Glu Val Pro Tyr Asn Ala Phe Leu Leu Met Ser Asp Glu
                           275                 280                 285
            Leu Gly Leu Ala Asn Met Thr Glu Gly Lys Ser Lys Lys Pro Lys Thr
                290                 295                 300
            Leu Ala Lys Glu Cys Leu Glu Lys Tyr Ser Thr Leu Arg Asp Gln Thr
            305                 310                 315                 320
            Asp Pro Ile Leu Ile Met Lys Ser Glu Lys Ala Asn Glu Asn Phe Leu
                           325                 330                 335
            Trp Lys Leu Trp Arg Asp Cys Val Asn Thr Ile Ser Asn Glu Glu Thr
                           340                 345                 350
            Ser Asn Glu Leu Gln Lys Thr Asn Tyr Ala Lys Trp Ala Thr Gly Asp
                           355                 360                 365
            Gly Leu Thr Tyr Gln Lys Ile Met Lys Glu Val Ala Ile Asp Asp Glu
                370                 375                 380
            Thr Met Tyr Gln Glu Glu Pro Lys Ile Pro Asn Lys Cys Arg Val Ala
            385                 390                 395                 400
            Ala Trp Val Gln Thr Glu Met Asn Leu Leu Ser Thr Leu Thr Ser Lys
                           405                 410                 415
            Arg Ala Leu Asp Leu Pro Glu Ile Gly Pro Asp Val Ala Pro Val Glu
                           420                 425                 430
            His Val Gly Ser Glu Arg Arg Lys Tyr Phe Val Asn Glu Ile Asn Tyr
                           435                 440                 445
            Cys Lys Ala Ser Thr Val Met Met Lys Tyr Val Leu Phe His Thr Ser
                450                 455                 460
            Leu Leu Asn Glu Ser Asn Ala Ser Met Gly Lys Tyr Lys Val Ile Pro
            465                 470                 475                 480
            Ile Thr Asn Arg Val Val Asn Glu Lys Gly Glu Ser Phe Asp Ile Leu
                           485                 490                 495
```

```
Tyr Gly Leu Ala Val Lys Gly Gln Ser His Leu Arg Gly Asp Thr Asp
            500                 505                 510

Val Val Thr Val Thr Phe Glu Phe Ser Ser Thr Asp Pro Arg Val
            515                 520                 525

Asp Ser Gly Lys Trp Pro Lys Tyr Thr Val Phe Arg Ile Gly Ser Leu
    530                 535                 540

Phe Val Ser Gly Arg Glu Lys Ser Val Tyr Leu Tyr Cys Arg Val Asn
545                 550                 555                 560

Gly Thr Asn Lys Ile Gln Met Lys Trp Gly Met Glu Ala Arg Cys
            565                 570                 575

Leu Leu Gln Ser Met Gln Met Glu Ala Ile Val Asp Gln Glu Ser
            580                 585                 590

Ser Ile Gln Gly Tyr Asp Met Thr Lys Ala Cys Phe Lys Gly Asp Arg
            595                 600                 605

Val Asn Ser Pro Lys Thr Phe Ser Ile Gly Thr Gln Glu Gly Lys Leu
    610                 615                 620

Val Lys Gly Ser Phe Gly Lys Ala Leu Arg Val Ile Phe Thr Lys Cys
625                 630                 635                 640

Leu Met His Tyr Val Phe Gly Asn Ala Gln Leu Glu Gly Phe Ser Ala
            645                 650                 655

Glu Ser Arg Arg Leu Leu Leu Ile Gln Ala Leu Lys Asp Arg Lys
            660                 665                 670

Gly Pro Trp Val Phe Asp Leu Glu Gly Met Tyr Ser Gly Ile Glu Glu
            675                 680                 685

Cys Ile Ser Asn Asn Pro Trp Val Ile Gln Ser Ala Tyr Trp Phe Asn
    690                 695                 700

Glu Trp Leu Gly Phe Glu Lys Glu Gly Ser Lys Val Leu Glu Ser Ile
705                 710                 715                 720

Asp Glu Ile Met Asp Glu
                725

<210> SEQ ID NO 5
<211> LENGTH: 709
<212> TYPE: PRT
<213> ORGANISM: Influenza C virus type: C/JJ/1950

<400> SEQUENCE: 5

Met Ser Lys Thr Phe Ala Glu Ile Ala Glu Thr Phe Leu Glu Pro Glu
1               5                   10                  15

Ala Val Arg Ile Ala Lys Glu Ala Val Glu Glu Tyr Gly Asp His Glu
            20                  25                  30

Arg Lys Ile Ile Gln Ile Gly Ile His Phe Gln Val Cys Cys Met Phe
        35                  40                  45

Cys Asp Glu Tyr Leu Ser Thr Asn Gly Ser Asp Arg Phe Val Leu Ile
    50                  55                  60

Glu Gly Arg Lys Arg Gly Thr Ala Val Ser Leu Gln Asn Glu Leu Cys
65                  70                  75                  80

Lys Ser Tyr Asp Leu Glu Pro Leu Pro Phe Leu Cys Asp Ile Phe Asp
                85                  90                  95

Arg Glu Glu Lys Gln Phe Val Glu Ile Gly Ile Thr Arg Lys Ala Asp
            100                 105                 110

Asp Ser Tyr Phe Gln Ser Lys Phe Gly Lys Leu Gly Asn Ser Cys Lys
        115                 120                 125

Ile Phe Val Phe Ser Tyr Asp Gly Arg Leu Asp Lys Asn Cys Glu Gly
    130                 135                 140
```

```
Pro Met Glu Glu Gln Lys Leu Arg Ile Phe Ser Phe Leu Ala Thr Ala
145                 150                 155                 160

Ala Asp Phe Leu Arg Lys Glu Asn Met Phe Asn Glu Ile Phe Leu Pro
            165                 170                 175

Asp Asn Glu Glu Thr Ile Ile Glu Met Lys Lys Gly Lys Thr Phe Leu
        180                 185                 190

Lys Leu Arg Asp Glu Ser Val Pro Leu Pro Phe Gln Thr Tyr Glu Gln
    195                 200                 205

Met Lys Asp Tyr Cys Glu Lys Phe Lys Gly Asn Pro Arg Glu Leu Ala
210                 215                 220

Ser Lys Val Ser Gln Met Gln Ser Asn Ile Lys Leu Pro Ile Lys His
225                 230                 235                 240

Tyr Glu Gln Asn Lys Phe Arg Gln Ile Arg Leu Pro Lys Gly Pro Met
            245                 250                 255

Ala Pro Tyr Thr His Lys Phe Leu Met Glu Glu Ala Trp Met Phe Thr
        260                 265                 270

Lys Ile Ser Asp Pro Glu Arg Ser Arg Ala Gly Glu Ile Leu Ile Asp
    275                 280                 285

Phe Phe Lys Lys Gly Asn Leu Ser Ala Ile Arg Pro Lys Asp Lys Pro
290                 295                 300

Leu Gln Gly Lys Tyr Pro Ile His Tyr Lys Asn Leu Trp Asn Gln Ile
305                 310                 315                 320

Lys Ala Ala Ile Ala Asp Arg Thr Met Val Ile Ser Glu Asn Asp His
            325                 330                 335

Ser Glu Phe Leu Gly Gly Ile Gly Arg Ala Ser Lys Lys Ile Pro Glu
        340                 345                 350

Val Ser Leu Thr Gln Asp Val Ile Thr Thr Glu Gly Leu Lys Gln Ser
    355                 360                 365

Glu Asn Lys Leu Pro Glu Pro Arg Ser Phe Pro Lys Trp Phe Asn Ala
370                 375                 380

Glu Trp Met Trp Ala Ile Lys Asp Ser Asp Leu Thr Gly Trp Val Pro
385                 390                 395                 400

Met Ala Glu Tyr Pro Pro Ala Asp Asn Glu Leu Glu Asp Tyr Ala Glu
            405                 410                 415

His Leu Asn Lys Thr Met Glu Gly Val Leu Gln Gly Thr Asn Cys Ala
        420                 425                 430

Arg Glu Met Gly Lys Cys Ile Leu Thr Val Gly Ala Leu Met Thr Glu
    435                 440                 445

Cys Arg Leu Phe Pro Gly Lys Ile Lys Val Val Pro Ile Tyr Ala Arg
450                 455                 460

Ser Lys Glu Arg Lys Ser Met Gln Glu Gly Leu Pro Val Pro Ser Glu
465                 470                 475                 480

Met Asp Cys Leu Phe Gly Ile Cys Val Lys Ser Lys Ser His Leu Asn
            485                 490                 495

Lys Asp Asp Gly Met Tyr Thr Ile Ile Thr Phe Glu Phe Ser Ile Arg
        500                 505                 510

Glu Pro Asn Leu Glu Lys His Gln Lys Tyr Thr Val Phe Glu Ala Gly
    515                 520                 525

His Thr Thr Val Arg Met Lys Lys Gly Glu Ser Val Ile Gly Arg Glu
530                 535                 540

Val Pro Leu Tyr Leu Tyr Cys Arg Thr Thr Ala Leu Ser Lys Ile Lys
545                 550                 555                 560

Asn Asp Trp Leu Ser Lys Ala Arg Arg Cys Phe Ile Thr Thr Met Asp
            565                 570                 575
```

```
Thr Val Glu Thr Ile Cys Leu Arg Glu Ser Ala Lys Ala Glu Glu Asn
            580                 585                 590

Leu Val Glu Lys Thr Leu Asn Glu Lys Gln Met Trp Ile Gly Lys Lys
            595                 600                 605

Asn Gly Glu Leu Ile Ala Gln Pro Leu Arg Glu Ala Leu Arg Val Gln
            610                 615                 620

Leu Val Gln Gln Phe Tyr Phe Cys Ile Tyr Asn Asp Ser Gln Leu Glu
625                 630                 635                 640

Gly Phe Cys Asn Glu Gln Lys Lys Ile Leu Met Ala Leu Glu Gly Asp
                645                 650                 655

Lys Lys Asn Lys Ser Ser Phe Gly Phe Asn Pro Glu Gly Leu Leu Glu
            660                 665                 670

Lys Ile Glu Glu Cys Leu Ile Asn Asn Pro Met Cys Leu Phe Met Ala
            675                 680                 685

Gln Arg Leu Asn Glu Leu Val Ile Glu Ala Ser Lys Arg Gly Ala Lys
690                 695                 700

Phe Phe Lys Ile Asp
705

<210> SEQ ID NO 6
<211> LENGTH: 757
<212> TYPE: PRT
<213> ORGANISM: Influenza A virus type: A/Brevig Mission/1/1918

<400> SEQUENCE: 6

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Arg Trp Thr Thr Asn Thr Glu Thr Gly Ala Pro
        50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240
```

```
Ile Ala Thr Pro Gly Met Gln Ile Arg Gly Phe Val Tyr Phe Val Glu
            245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
            275                 280                 285

Met Met Thr Asn Ser Gln Asp Thr Glu Leu Ser Phe Thr Ile Thr Gly
            290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
            355                 360                 365

Pro Ala Glu Met Leu Ala Ser Ile Asp Leu Lys Tyr Phe Asn Asp Ser
            370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
            435                 440                 445

Leu Ile Val Asn Ala Pro Asn His Glu Gly Ile Gln Ala Gly Val Asp
            450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
            515                 520                 525

Val Ile Lys Asn Asn Met Ile Asn Asn Asp Leu Gly Pro Ala Thr Ala
            530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
            595                 600                 605

Val Cys Leu Lys Trp Glu Leu Met Asp Glu Asp Tyr Gln Gly Arg Leu
            610                 615                 620

Cys Asn Pro Leu Asn Pro Phe Val Ser His Lys Glu Ile Glu Ser Val
625                 630                 635                 640

Asn Asn Ala Val Met Met Pro Ala His Gly Pro Ala Lys Asn Met Glu
                645                 650                 655

Tyr Asp Ala Val Ala Thr Thr His Ser Trp Ile Pro Lys Arg Asn Arg
```

-continued

```
                660                 665                 670
Ser Ile Leu Asn Thr Ser Gln Arg Gly Ile Leu Glu Asp Glu Gln Met
            675                 680                 685

Tyr Gln Lys Cys Cys Asn Leu Phe Glu Lys Phe Phe Pro Ser Ser Ser
        690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ala Glu Ile Met Lys Ile Cys Ser Thr Ile Glu Glu
            740                 745                 750

Leu Arg Arg Gln Lys
        755

<210> SEQ ID NO 7
<211> LENGTH: 752
<212> TYPE: PRT
<213> ORGANISM: Influenza B virus type: B/Ann Arbor/1/1966

<400> SEQUENCE: 7

Met Asn Ile Asn Pro Tyr Phe Leu Phe Ile Asp Val Pro Ile Gln Ala
1               5                   10                  15

Ala Ile Ser Thr Thr Phe Pro Tyr Thr Gly Val Pro Pro Tyr Ser His
            20                  25                  30

Gly Thr Gly Thr Gly Tyr Thr Ile Asp Thr Val Ile Arg Thr His Glu
        35                  40                  45

Tyr Ser Asn Lys Gly Lys Gln Tyr Ile Ser Asp Val Thr Gly Cys Ala
    50                  55                  60

Met Val Asp Pro Thr Asn Gly Pro Leu Pro Glu Asp Asn Glu Pro Ser
65                  70                  75                  80

Ala Tyr Ala Gln Leu Asp Cys Val Leu Glu Ala Leu Asp Arg Met Asp
                85                  90                  95

Glu Glu His Pro Gly Leu Phe Gln Ala Ala Ser Gln Asn Ala Met Glu
            100                 105                 110

Ala Leu Met Val Thr Thr Val Asp Lys Leu Thr Gln Gly Arg Gln Thr
        115                 120                 125

Phe Asp Trp Thr Val Cys Arg Asn Gln Pro Ala Ala Thr Ala Leu Asn
    130                 135                 140

Thr Thr Ile Thr Ser Phe Arg Leu Asn Asp Leu Asn Gly Ala Asp Lys
145                 150                 155                 160

Gly Gly Leu Val Pro Phe Cys Gln Asp Ile Ile Asp Ser Leu Asp Lys
                165                 170                 175

Pro Glu Met Thr Phe Phe Ser Val Lys Asn Ile Lys Lys Lys Leu Pro
            180                 185                 190

Ala Lys Asn Arg Lys Gly Phe Leu Ile Lys Arg Ile Pro Met Lys Val
        195                 200                 205

Lys Asp Arg Ile Thr Arg Val Glu Tyr Ile Lys Arg Ala Leu Ser Leu
    210                 215                 220

Asn Thr Met Thr Lys Asp Ala Glu Arg Gly Lys Leu Lys Arg Arg Ala
225                 230                 235                 240

Ile Ala Thr Ala Gly Ile Gln Ile Arg Gly Phe Val Leu Val Val Glu
                245                 250                 255

Asn Leu Ala Lys Asn Ile Cys Glu Asn Leu Glu Gln Ser Gly Leu Pro
            260                 265                 270

Val Gly Gly Asn Glu Lys Lys Ala Lys Leu Ser Asn Ala Val Ala Lys
```

```
                275                 280                 285
Met Leu Ser Asn Cys Pro Pro Gly Gly Ile Ser Met Thr Val Thr Gly
290                 295                 300

Asp Asn Thr Lys Trp Asn Glu Cys Leu Asn Pro Arg Ile Phe Leu Ala
305                 310                 315                 320

Met Thr Glu Arg Ile Thr Arg Asp Ser Pro Ile Trp Phe Arg Asp Phe
            325                 330                 335

Cys Ser Ile Ala Pro Val Leu Phe Ser Asn Lys Ile Ala Arg Leu Gly
            340                 345                 350

Lys Gly Phe Met Ile Thr Ser Lys Thr Lys Arg Leu Lys Ala Gln Ile
            355                 360                 365

Pro Cys Pro Asp Leu Phe Asn Ile Pro Leu Glu Arg Tyr Asn Glu Glu
370                 375                 380

Thr Arg Ala Lys Leu Lys Lys Leu Lys Pro Phe Asn Glu Glu Gly
385                 390                 395                 400

Thr Ala Ser Leu Ser Pro Gly Met Met Met Gly Met Phe Asn Met Leu
                405                 410                 415

Ser Thr Val Leu Gly Val Ala Ala Leu Gly Ile Lys Asn Ile Gly Asn
            420                 425                 430

Arg Glu Tyr Leu Trp Asp Gly Leu Gln Ser Ser Asp Asp Phe Ala Leu
            435                 440                 445

Phe Val Asn Ala Lys Asp Glu Thr Cys Met Glu Gly Ile Asn Asp
450                 455                 460

Phe Tyr Arg Thr Cys Lys Leu Leu Gly Ile Asn Met Ser Lys Lys Lys
465                 470                 475                 480

Ser Tyr Cys Asn Glu Thr Gly Met Phe Glu Phe Thr Ser Met Phe Tyr
                485                 490                 495

Arg Asp Gly Phe Val Ser Asn Phe Ala Met Glu Leu Pro Ser Phe Gly
            500                 505                 510

Val Ala Gly Val Asn Glu Ser Ala Asp Met Ala Ile Gly Met Thr Ile
            515                 520                 525

Ile Lys Asn Asn Met Ile Asn Asn Gly Met Gly Pro Ala Thr Ala Gln
530                 535                 540

Thr Ala Ile Gln Leu Phe Ile Ala Asp Tyr Arg Tyr Thr Tyr Lys Cys
545                 550                 555                 560

His Arg Gly Asp Ser Lys Val Glu Gly Lys Arg Met Lys Ile Ile Lys
                565                 570                 575

Glu Leu Trp Glu Asn Thr Lys Gly Arg Asp Gly Leu Leu Val Ala Asp
            580                 585                 590

Gly Gly Pro Asn Ile Tyr Asn Leu Arg Asn Leu His Ile Pro Glu Ile
            595                 600                 605

Val Leu Lys Tyr Asn Leu Met Asp Pro Glu Tyr Lys Gly Arg Leu Leu
610                 615                 620

His Pro Gln Asn Pro Phe Val Gly His Leu Ser Ile Glu Gly Ile Lys
625                 630                 635                 640

Glu Ala Asp Ile Thr Pro Ala His Gly Pro Ile Lys Lys Met Asp Tyr
                645                 650                 655

Asp Ala Val Ser Gly Thr His Ser Trp Arg Thr Lys Arg Asn Arg Ser
            660                 665                 670

Ile Leu Asn Thr Asp Gln Arg Asn Met Ile Leu Glu Glu Gln Cys Tyr
            675                 680                 685

Ala Lys Cys Cys Asn Leu Phe Glu Ala Cys Phe Asn Ser Ala Ser Tyr
690                 695                 700
```

```
Arg Lys Pro Val Gly Gln His Ser Met Leu Glu Ala Met Ala His Arg
705                 710                 715                 720

Leu Arg Met Asp Ala Arg Leu Asp Tyr Glu Ser Gly Arg Met Ser Lys
            725                 730                 735

Asp Asp Phe Glu Lys Ala Met Ala His Leu Gly Glu Ile Gly His Ile
        740                 745                 750
```

<210> SEQ ID NO 8
<211> LENGTH: 754
<212> TYPE: PRT
<213> ORGANISM: Influenza C virus type: C/JJ/1950

<400> SEQUENCE: 8

```
Met Glu Ile Asn Pro Tyr Leu Met Phe Leu Asn Asn Asp Val Thr Ser
1               5                   10                  15

Leu Ile Ser Thr Thr Tyr Pro Tyr Thr Gly Pro Pro Met Ser His
            20                  25                  30

Gly Ser Ser Thr Lys Tyr Thr Leu Glu Thr Ile Lys Arg Thr Tyr Asp
            35                  40                  45

Tyr Ser Arg Thr Ser Val Glu Lys Thr Ser Lys Val Phe Asn Ile Pro
50                  55                  60

Arg Arg Lys Phe Cys Asn Cys Leu Glu Asp Lys Asp Asp Leu Val Lys
65                  70                  75                  80

Pro Thr Gly Asn Val Asp Ile Ser Ser Leu Gly Leu Ala Glu Met
                85                  90                  95

Met Glu Lys Arg Met Gly Glu Gly Phe Phe Lys His Cys Val Met Glu
                100                 105                 110

Ala Glu Thr Glu Ile Leu Lys Met His Phe Ser Arg Leu Thr Glu Gly
            115                 120                 125

Arg Gln Thr Tyr Asp Trp Thr Ser Glu Arg Asn Met Pro Ala Ala Thr
130                 135                 140

Ala Leu Gln Leu Thr Val Asp Ala Ile Lys Glu Thr Glu Gly Pro Phe
145                 150                 155                 160

Lys Gly Thr Thr Met Leu Glu Tyr Cys Asn Lys Met Ile Glu Met Leu
                165                 170                 175

Asp Trp Lys Glu Val Lys Phe Arg Lys Val Lys Thr Met Val Arg Arg
            180                 185                 190

Glu Lys Asp Lys Arg Ser Gly Lys Glu Ile Lys Thr Lys Val Pro Val
            195                 200                 205

Met Gly Ile Asp Ser Ile Lys His Asp Glu Phe Leu Ile Arg Ala Leu
210                 215                 220

Thr Ile Asn Thr Met Ala Lys Asp Gly Glu Arg Gly Lys Leu Gln Arg
225                 230                 235                 240

Arg Ala Ile Ala Thr Pro Gly Met Ile Val Arg Pro Phe Ser Lys Ile
                245                 250                 255

Val Glu Thr Val Ala Gln Lys Ile Cys Glu Lys Leu Lys Glu Ser Gly
            260                 265                 270

Leu Pro Val Gly Gly Asn Glu Lys Lys Ala Lys Leu Lys Thr Thr Val
            275                 280                 285

Thr Ser Leu Asn Ala Arg Met Asn Ser Asp Gln Phe Ala Val Asn Ile
290                 295                 300

Thr Gly Asp Asn Ser Lys Trp Asn Glu Cys Gln Gln Pro Glu Ala Tyr
305                 310                 315                 320

Leu Ala Leu Leu Ala Tyr Ile Thr Lys Asp Ser Ser Asp Leu Met Lys
                325                 330                 335
```

-continued

```
Asp Leu Cys Ser Val Ala Pro Val Leu Phe Cys Asn Lys Phe Val Lys
            340                 345                 350
Leu Gly Gln Gly Ile Arg Leu Ser Asn Lys Arg Lys Thr Lys Glu Val
            355                 360                 365
Ile Ile Lys Ala Glu Lys Met Gly Lys Tyr Lys Asn Leu Met Arg Glu
            370                 375                 380
Glu Tyr Lys Asn Leu Phe Glu Pro Leu Glu Lys Tyr Ile Gln Lys Asp
385                 390                 395                 400
Val Cys Phe Leu Pro Gly Gly Met Leu Met Gly Met Phe Asn Met Leu
                    405                 410                 415
Ser Thr Val Leu Gly Val Ser Thr Leu Cys Tyr Met Asp Glu Glu Leu
                420                 425                 430
Lys Ala Lys Gly Cys Phe Trp Thr Gly Leu Gln Ser Ser Asp Asp Phe
            435                 440                 445
Val Leu Phe Ala Val Ala Ser Asn Trp Ser Asn Ile His Trp Thr Ile
            450                 455                 460
Arg Arg Phe Asn Ala Val Cys Lys Leu Ile Gly Ile Asn Met Ser Leu
465                 470                 475                 480
Glu Lys Ser Tyr Gly Ser Leu Pro Glu Leu Phe Glu Phe Thr Ser Met
                    485                 490                 495
Phe Phe Asp Gly Glu Phe Val Ser Asn Leu Ala Met Glu Leu Pro Ala
                500                 505                 510
Phe Thr Thr Ala Gly Val Asn Glu Gly Val Asp Phe Thr Ala Ala Met
            515                 520                 525
Ser Ile Ile Lys Thr Asn Met Ile Asn Asn Ser Leu Ser Pro Ser Thr
            530                 535                 540
Ala Leu Met Ala Leu Arg Ile Cys Leu Gln Glu Phe Arg Ala Thr Tyr
545                 550                 555                 560
Arg Val His Pro Trp Asp Ser Lys Val Lys Gly Gly Arg Met Lys Ile
                    565                 570                 575
Ile Asn Glu Phe Ile Lys Thr Ile Glu Ser Lys Asp Gly Leu Leu Ile
                580                 585                 590
Ala Asp Gly Gly Lys Leu Met Asn Asn Ile Ser Thr Leu His Ile Pro
            595                 600                 605
Glu Glu Val Leu Lys Phe Glu Lys Met Asp Glu Gln Tyr Arg Asn Arg
            610                 615                 620
Val Phe Asn Pro Lys Asn Pro Phe Thr Asn Phe Asp Lys Thr Ile Asp
625                 630                 635                 640
Ile Phe Arg Ala His Gly Pro Ile Arg Val Glu Glu Asn Glu Ala Val
                    645                 650                 655
Val Ser Thr His Ser Phe Arg Thr Arg Ala Asn Arg Thr Leu Leu Asn
                660                 665                 670
Thr Asp Met Arg Ala Met Met Ala Glu Glu Lys Arg Tyr Gln Met Val
            675                 680                 685
Cys Asp Ile Phe Lys Ser Val Phe Glu Ser Ala Asp Ile Asn Pro Pro
            690                 695                 700
Ile Gly Ala Met Ser Ile Gly Glu Ala Ile Glu Glu Lys Leu Leu Glu
705                 710                 715                 720
Arg Ala Lys Met Lys Arg Asp Ile Gly Ala Ile Glu Asp Ser Glu Tyr
                    725                 730                 735
Glu Glu Ile Lys Asp Ile Ile Arg Asp Ala Lys Lys Ala Arg Ile Glu
                740                 745                 750
Ser Arg
```